(12) United States Patent
Jang

(10) Patent No.: US 9,445,926 B2
(45) Date of Patent: Sep. 20, 2016

(54) INTRAVASCULAR STENT

(75) Inventor: G. David Jang, Redmonds, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 2204 days.

(21) Appl. No.: 12/192,782

(22) Filed: Aug. 15, 2008

(65) Prior Publication Data

US 2008/0300674 A1 Dec. 4, 2008

Related U.S. Application Data

(63) Continuation of application No. 10/374,774, filed on Feb. 25, 2003, now abandoned, which is a continuation-in-part of application No. 10/206,432, filed on Jul. 25, 2002, now Pat. No. 8,021,414, which (Continued)

(51) Int. Cl.

| A61F 2/06 | (2013.01) |
|---|---|
| A61F 2/915 | (2013.01) |
| A61F 2/91 | (2013.01) |
| A61F 2/958 | (2013.01) |

(52) U.S. Cl.
CPC ............... *A61F 2/915* (2013.01); *A61F 2/91* (2013.01); *A61F 2/958* (2013.01); *A61F 2002/91525* (2013.01); *A61F 2002/91533* (2013.01); *A61F 2002/91558* (2013.01); *A61F 2002/91583* (2013.01); *A61F 2230/0013* (2013.01); *A61F 2250/0018* (2013.01); *A61F 2250/0067* (2013.01)

(58) Field of Classification Search
CPC .......... A61F 2/915; A61F 2/91; A61F 2/958; A61F 2002/91525; A61F 2002/91533; A61F 2002/91558; A61F 2002/91583; A61F 2250/0018; A61F 2250/0067; A61F 2230/0013
USPC ...................... 623/1.15, 1.16, 23.7
See application file for complete search history.

(56) References Cited

U.S. PATENT DOCUMENTS

| 2,836,181 A | 5/1958 | Tapp |
|---|---|---|
| 3,015,492 A | 10/1963 | Jeckel |
| 3,272,204 A | 9/1966 | Artandi et al. |
| 3,490,975 A | 1/1970 | Lightwood et al. |

(Continued)

FOREIGN PATENT DOCUMENTS

| CA | 2421830 | 9/2001 |
|---|---|---|
| DE | 43 03 181 A1 | 8/1994 |

(Continued)

OTHER PUBLICATIONS

Manufacturing Processes for Engineering Materials, by Serope Kalpakjian, Illinois Institute of Technology, Addison-Wesley Publishing Company, pp. 340, Jun. 1991.

(Continued)

*Primary Examiner* — Paul Prebilic

(57) ABSTRACT

A stent comprises a first expansion strut column of first expansion strut pairs and a second expansion strut column of second expansion strut pairs. Each first expansion strut pair is connected to a second expansion strut pair by a connecting strut. Each connecting strut comprises at least one wrap portion, the at least one wrap portion being at least partially wrapped about at least one of the first joining portions of at least one of the first expansion strut column and the second expansion strut column.

18 Claims, 84 Drawing Sheets

Related U.S. Application Data is a continuation of application No. 09/574,077, filed on May 18, 2000, now Pat. No. 6,770,088, which is a continuation of application No. 08/845,734, filed on Apr. 25, 1997, now abandoned, which is a continuation-in-part of application No. 08/824,142, filed on Mar. 25, 1997, now Pat. No. 6,241,760, and a continuation-in-part of application No. 08/824,866, filed on Mar. 26, 1997, now Pat. No. 5,954,743, and a continuation-in-part of application No. 08/824,865, filed on Mar. 26, 1997, now Pat. No. 6,152,957, and a continuation-in-part of application No. 08/845,657, filed on Apr. 25, 1997, now Pat. No. 5,922,021, said application No. 10/374,774 is a continuation-in-part of application No. 10/123,883, filed on Apr. 15, 2002, now abandoned, which is a continuation of application No. 09/839,442, filed on Apr. 20, 2001, now Pat. No. 6,409,761, which is a continuation of application No. 08/824,142, said application No. 10/123,883 is a continuation of application No. 09/839,287, filed on Apr. 20, 2001, now abandoned, which is a continuation of application No. 09/237,537, filed on Jan. 26, 1999, now Pat. No. 6,235,053, said application No. 10/374,774 is a continuation-in-part of application No. 10/321,005, filed on Dec. 17, 2002, now Pat. No. 8,562,665, which is a continuation of application No. 09/839,287, which is a continuation of application No. 09/237,537, said application No. 10/374,774 is a continuation-in-part of application No. 09/960,861, filed on Sep. 21, 2001, now abandoned, said application No. 10/374,774 is a continuation-in-part of application No. 09/874,349, filed on Jun. 4, 2001, now Pat. No. 6,783,543, said application No. 10/374,774 is a continuation-in-part of application No. 10/297,372, filed as application No. PCT/US01/18419 on Jun. 5, 2001, now abandoned, said application No. 10/374,774 is a continuation-in-part of application No. 09/942,077, filed on Aug. 28, 2001, now abandoned.

(60) Provisional application No. 60/017,484, filed on Apr. 26, 1996, provisional application No. 60/073,412, filed on Feb. 2, 1998, provisional application No. 60/234,614, filed on Sep. 22, 2000, provisional application No. 60/209,255, filed on Jun. 5, 2000, provisional application No. 60/235,164, filed on Sep. 23, 2000.

(56) References Cited

U.S. PATENT DOCUMENTS

| | | | |
|---|---|---|---|
| 3,509,883 | A | 5/1970 | Dibelius et al. |
| 3,526,228 | A | 9/1970 | Lyng |
| 3,562,820 | A | 2/1971 | Braun et al. |
| 3,635,215 | A | 1/1972 | Shea et al. |
| 3,771,526 | A | 11/1973 | Rudle |
| 3,868,956 | A | 3/1975 | Alfidi et al. |
| 3,993,078 | A | 11/1976 | Bergentz et al. |
| 4,078,167 | A | 3/1978 | Banas et al. |
| 4,127,761 | A | 11/1978 | Pauley et al. |
| 4,130,904 | A | 12/1978 | Whalen |
| 4,140,126 | A | 2/1979 | Choudhury |
| 4,141,364 | A | 2/1979 | Schultze |
| 4,164,045 | A | 8/1979 | Bokros et al. |
| 4,214,587 | A | 7/1980 | Sakura, Jr. |
| 4,300,244 | A | 11/1981 | Bokros |
| 4,313,231 | A | 2/1982 | Koyamada |
| 4,319,363 | A | 3/1982 | Ketharanathan |
| 4,425,908 | A | 1/1984 | Simon |
| 4,441,215 | A | 4/1984 | Kaster |
| 4,470,407 | A | 9/1984 | Hussein |
| 4,501,264 | A | 2/1985 | Rockey |
| 4,503,569 | A | 3/1985 | Dotter |
| 4,512,338 | A | 4/1985 | Balko et al. |
| 4,535,770 | A | 8/1985 | Lemole |
| 4,550,447 | A | 11/1985 | Seiler, Jr. et al. |
| 4,553,545 | A | 11/1985 | Maass et al. |
| 4,560,374 | A | 12/1985 | Hammerslag |
| 4,580,568 | A | 4/1986 | Gianturco |
| 4,597,389 | A | 7/1986 | Ibrahim et al. |
| 4,647,416 | A | 3/1987 | Seiler, Jr. et al. |
| 4,649,922 | A | 3/1987 | Wiktor |
| 4,655,771 | A | 4/1987 | Wallsten |
| 4,655,776 | A | 4/1987 | Lesinski |
| 4,665,918 | A | 5/1987 | Garza et al. |
| 4,681,110 | A | 7/1987 | Wiktor |
| 4,693,721 | A | 9/1987 | Ducheyne |
| 4,733,665 | A | 3/1988 | Palmaz |
| 4,739,762 | A | 4/1988 | Palmaz |
| 4,740,207 | A | 4/1988 | Kreamer |
| 4,760,849 | A | 8/1988 | Kropf |
| 4,762,128 | A | 8/1988 | Rosenbluth |
| 4,768,507 | A | 9/1988 | Fischell |
| 4,769,029 | A | 9/1988 | Patel |
| 4,771,773 | A | 9/1988 | Kropf |
| 4,776,337 | A | 10/1988 | Palmaz |
| 4,787,899 | A | 11/1988 | Lazarus |
| 4,795,458 | A | 1/1989 | Regan |
| 4,795,465 | A | 1/1989 | Marten |
| 4,800,882 | A | 1/1989 | Gianturco |
| 4,820,298 | A | 4/1989 | Laveen et al. |
| 4,830,003 | A | 5/1989 | Wolff et al. |
| 4,842,575 | A | 6/1989 | Hoffman, Jr. et al. |
| 4,848,343 | A | 7/1989 | Wallsten et al. |
| 4,851,009 | A | 7/1989 | Pinchuk |
| 4,856,516 | A | 8/1989 | Hillstead |
| 4,872,874 | A | 10/1989 | Taheri |
| 4,877,030 | A | 10/1989 | Beck et al. |
| 4,878,906 | A | 11/1989 | Lindemann et al. |
| 4,886,062 | A | 12/1989 | Wiktor |
| 4,913,141 | A | 4/1990 | Hillstead |
| 4,922,905 | A | 5/1990 | Strecker |
| 4,950,227 | A | 8/1990 | Savin et al. |
| 4,950,258 | A | 8/1990 | Kawai et al. |
| 4,994,071 | A | 2/1991 | MacGregor |
| 5,015,253 | A | 5/1991 | MacGregor |
| 5,019,090 | A | 5/1991 | Pinchuk |
| 5,035,706 | A | 7/1991 | Giantureo et al. |
| 5,037,392 | A | 8/1991 | Hillstead |
| 5,059,211 | A | 10/1991 | Stack et al. |
| 5,064,435 | A | 11/1991 | Porter |
| 5,092,877 | A | 3/1992 | Pinchuk |
| 5,102,417 | A | 4/1992 | Palmaz |
| 5,104,399 | A | 4/1992 | Lazarus |
| 5,104,404 | A | 4/1992 | Wolff |
| 5,108,417 | A | 4/1992 | Sawyer |
| 5,122,154 | A | 6/1992 | Rhodes |
| 5,133,732 | A | 7/1992 | Wiktor |
| 5,135,536 | A | 8/1992 | Hillstead |
| 5,139,480 | A | 8/1992 | Kickle et al. |
| 5,147,385 | A | 9/1992 | Beck et al. |
| 5,147,400 | A | 9/1992 | Kaplan et al. |
| 5,158,548 | A | 10/1992 | Lau et al. |
| 5,163,952 | A | 11/1992 | Froix |
| 5,195,984 | A | 3/1993 | Schatz |
| 5,197,978 | A | 3/1993 | Hess |
| 5,217,483 | A | 6/1993 | Tower |
| 5,226,913 | A | 7/1993 | Pinchuk |
| 5,282,823 | A | 2/1994 | Schwartz et al. |
| 5,282,824 | A | 2/1994 | Gianturco |
| 5,292,331 | A | 3/1994 | Boneau |
| 5,304,200 | A | 4/1994 | Spaulding |
| 5,312,430 | A | 5/1994 | Rosenbluth et al. |
| 5,314,472 | A | 5/1994 | Fontaine |
| 5,344,425 | A | 9/1994 | Sawyer |
| 5,354,308 | A | 10/1994 | Simon et al. |
| 5,383,892 | A | 1/1995 | Cardon et al. |

(56) References Cited

U.S. PATENT DOCUMENTS

| | | |
|---|---|---|
| 5,389,106 A | 2/1995 | Tower |
| 5,405,377 A | 4/1995 | Cragg |
| 5,449,373 A | 9/1995 | Pinchasik et al. |
| 5,507,767 A | 4/1996 | Maeda et al. |
| 5,527,354 A | 6/1996 | Fontaine et al. |
| 5,545,210 A | 8/1996 | Hess et al. |
| 5,549,663 A | 8/1996 | Cottone, Jr. |
| 5,591,197 A | 1/1997 | Orth et al. |
| 5,593,442 A | 1/1997 | Klein |
| 5,607,442 A | 3/1997 | Fischell et al. |
| 5,613,981 A | 3/1997 | Boyle et al. |
| 5,653,727 A | 8/1997 | Wiktor |
| 5,669,924 A | 9/1997 | Shaknovich |
| 5,676,671 A | 10/1997 | Inoue |
| 5,695,516 A | 12/1997 | Fischell et al. |
| 5,697,971 A | 12/1997 | Fischell et al. |
| 5,707,386 A | 1/1998 | Schnepp-Pesch et al. |
| 5,713,949 A | 2/1998 | Jayaraman |
| 5,716,393 A * | 2/1998 | Lindenberg et al. .......... 623/1.2 |
| 5,718,713 A | 2/1998 | Frantzen |
| 5,733,301 A | 3/1998 | Forman |
| 5,733,303 A | 3/1998 | Israel et al. |
| 5,735,871 A | 4/1998 | Sgro |
| 5,735,893 A | 4/1998 | Lau et al. |
| 5,741,327 A | 4/1998 | Frantzen |
| 5,755,776 A | 5/1998 | Al-Saadon |
| 5,755,781 A | 5/1998 | Jayaraman |
| 5,759,192 A | 6/1998 | Saunders |
| 5,772,864 A | 6/1998 | Moller et al. |
| 5,776,161 A | 7/1998 | Globerman |
| 5,776,181 A | 7/1998 | Lee et al. |
| 5,776,183 A | 7/1998 | Kanesaka et al. |
| 5,807,404 A | 9/1998 | Richter |
| 5,810,767 A | 9/1998 | Klein |
| 5,810,872 A | 9/1998 | Kanesaka et al. |
| 5,824,043 A | 10/1998 | Cottone, Jr. |
| 5,824,059 A | 10/1998 | Wijay |
| 5,827,321 A | 10/1998 | Roubin et al. |
| 5,836,951 A | 11/1998 | Rosenbluth et al. |
| 5,836,964 A | 11/1998 | Richter et al. |
| 5,843,172 A | 12/1998 | Yan |
| 5,861,027 A | 1/1999 | Trapp |
| 5,876,449 A | 3/1999 | Starck et al. |
| 5,879,370 A | 3/1999 | Fischell et al. |
| 5,895,406 A | 4/1999 | Gray et al. |
| 5,897,588 A | 4/1999 | Hull et al. |
| 5,902,317 A | 5/1999 | Kleshinski et al. |
| 5,902,332 A | 5/1999 | Schatz |
| 5,911,754 A | 6/1999 | Kanesaka et al. |
| 5,913,895 A | 6/1999 | Burpee et al. |
| 5,922,019 A | 7/1999 | Hankh et al. |
| 5,922,020 A | 7/1999 | Klein et al. |
| 5,922,021 A | 7/1999 | Jang |
| 5,925,061 A * | 7/1999 | Ogi et al. .................... 623/1.2 |
| 5,938,682 A | 8/1999 | Hojeibane et al. |
| 5,939,227 A | 8/1999 | Smith |
| 5,948,016 A | 9/1999 | Jang |
| 5,953,743 A | 9/1999 | Jeddeloh |
| 5,954,743 A | 9/1999 | Jang |
| 5,964,798 A | 10/1999 | Imran |
| 5,968,093 A | 10/1999 | Kranz |
| 5,972,027 A | 10/1999 | Johnson |
| 5,980,553 A | 11/1999 | Gray et al. |
| 6,033,433 A | 3/2000 | Ehr et al. |
| 6,039,756 A | 3/2000 | Jang |
| 6,042,606 A | 3/2000 | Frantzen |
| 6,053,940 A | 4/2000 | Wijay |
| 6,066,169 A | 5/2000 | McGuinness |
| 6,106,548 A | 8/2000 | Roubin et al. |
| 6,113,627 A | 9/2000 | Jang |
| 6,117,165 A | 9/2000 | Becker |
| 6,123,721 A | 9/2000 | Jang |
| 6,129,755 A | 10/2000 | Mathis et al. |
| 6,152,957 A | 11/2000 | Jang |
| 6,156,052 A | 12/2000 | Richter et al. |
| 6,162,243 A | 12/2000 | Gray et al. |
| 6,168,621 B1 * | 1/2001 | Vrba .............................. 623/1.2 |
| 6,179,868 B1 | 1/2001 | Burpee et al. |
| 6,183,506 B1 | 2/2001 | Penn et al. |
| 6,190,403 B1 | 2/2001 | Fischell et al. |
| 6,190,404 B1 | 2/2001 | Palmaz et al. |
| 6,190,406 B1 | 2/2001 | Duerig et al. |
| 6,193,744 B1 | 2/2001 | Ehr et al. |
| 6,193,747 B1 | 2/2001 | Von Oepen |
| 6,200,334 B1 | 3/2001 | Jang |
| 6,200,337 B1 | 3/2001 | Moriuchi et al. |
| 6,203,569 B1 | 3/2001 | Wijay |
| 6,206,911 B1 | 3/2001 | Milo |
| 6,206,915 B1 | 3/2001 | Fagan et al. |
| 6,206,916 B1 | 3/2001 | Furst |
| 6,217,608 B1 | 4/2001 | Penn et al. |
| 6,231,598 B1 | 5/2001 | Berry et al. |
| 6,235,053 B1 | 5/2001 | Jang |
| 6,241,760 B1 | 6/2001 | Jang |
| 6,251,134 B1 | 6/2001 | Alt et al. |
| 6,254,632 B1 | 7/2001 | Wu et al. |
| 6,258,121 B1 | 7/2001 | Yang et al. |
| 6,261,319 B1 | 7/2001 | Kveen et al. |
| 6,261,320 B1 | 7/2001 | Tam et al. |
| 6,270,524 B1 | 8/2001 | Kim |
| 6,273,908 B1 | 8/2001 | Ndondo-Lay |
| 6,273,911 B1 | 8/2001 | Cox et al. |
| 6,273,913 B1 | 8/2001 | Wright et al. |
| 6,280,413 B1 | 8/2001 | Clark et al. |
| 6,331,189 B1 | 12/2001 | Wolinsky et al. |
| 6,342,067 B1 | 1/2002 | Mathis et al. |
| 6,348,065 B1 | 2/2002 | Brown et al. |
| 6,355,059 B1 | 3/2002 | Richter et al. |
| 6,379,381 B1 | 4/2002 | Hossainy et al. |
| 6,409,761 B1 | 6/2002 | Jang |
| 6,416,538 B1 | 7/2002 | Ley et al. |
| 6,423,090 B1 | 7/2002 | Hancock |
| 6,432,133 B1 | 8/2002 | Lau et al. |
| 6,443,982 B1 | 9/2002 | Israel et al. |
| 6,451,049 B2 | 9/2002 | Vallana et al. |
| 6,461,380 B1 | 10/2002 | Cox |
| 6,461,381 B2 | 10/2002 | Israel et al. |
| 6,464,720 B2 | 10/2002 | Boatman et al. |
| 6,464,722 B2 | 10/2002 | Israel et al. |
| 6,468,302 B2 | 10/2002 | Cox et al. |
| 6,471,720 B1 | 10/2002 | Ehr et al. |
| 6,475,236 B1 | 11/2002 | Roubin et al. |
| 6,478,816 B1 | 11/2002 | Kveen et al. |
| 6,485,508 B1 | 11/2002 | McGuinness |
| 6,770,088 B1 | 8/2004 | Jang |
| 6,945,993 B2 | 9/2005 | Kveen et al. |
| 6,955,686 B2 | 10/2005 | Majercak et al. |
| 7,179,286 B2 * | 2/2007 | Lenz ............................ 623/1.15 |
| 7,731,746 B2 * | 6/2010 | Kveen et al. ................ 623/1.15 |
| 7,780,719 B2 * | 8/2010 | Killion et al. ............... 623/1.15 |
| 7,905,912 B2 * | 3/2011 | Ehr et al. ..................... 623/1.11 |
| 2001/0010013 A1 | 7/2001 | Cox et al. |
| 2001/0020183 A1 | 9/2001 | Jang |
| 2001/0035783 A1 | 11/2001 | Kanba |
| 2002/0038145 A1 | 3/2002 | Jang |
| 2002/0042647 A1 | 4/2002 | Jang |
| 2002/0045933 A1 | 4/2002 | Jang |
| 2002/0045934 A1 | 4/2002 | Jang |
| 2002/0045935 A1 | 4/2002 | Jang |
| 2002/0049493 A1 | 4/2002 | Jang |
| 2002/0058990 A1 | 5/2002 | Jang |
| 2002/0161429 A1 | 10/2002 | Jang |
| 2002/0193870 A1 | 12/2002 | Jang |
| 2003/0028242 A1 | 2/2003 | Vallana et al. |
| 2003/0144729 A1 * | 7/2003 | Bicek et al. ................. 623/1.16 |

FOREIGN PATENT DOCUMENTS

| | | | |
|---|---|---|---|
| DE | 296 08 037 U1 | 8/1996 | |
| DE | 29702671 U1 * | 2/1997 | ............... A61F 2/04 |
| DE | 297 01 758 U1 | 5/1997 | |
| DE | 297 02 671 U1 | 5/1997 | |
| DE | 297 08 689 U1 | 8/1997 | |
| DE | 297 08 879 U1 | 9/1997 | |

(56) References Cited

FOREIGN PATENT DOCUMENTS

| EP | 0 183 372 A1 | 6/1986 |
|---|---|---|
| EP | 0 364 787 A1 | 4/1990 |
| EP | 0 364 787 B1 | 4/1990 |
| EP | 0 335 341 B1 | 4/1992 |
| EP | 0 540 290 A2 | 5/1993 |
| EP | 0 606 165 A1 | 1/1994 |
| EP | 0 587 197 A1 | 3/1994 |
| EP | 0 679 372 A2 | 11/1995 |
| EP | 0 709 067 A2 | 1/1996 |
| EP | 0 734 698 A2 | 2/1996 |
| EP | 0 821 920 A1 | 2/1998 |
| EP | 0 875 215 A1 | 11/1998 |
| EP | 0 950 386 A2 | 10/1999 |
| EP | 0 980 694 A2 | 2/2000 |
| FR | 2 785 174 A1 | 5/2000 |
| WO | 94/17754 A1 | 8/1994 |
| WO | 96/03029 A1 | 2/1996 |
| WO | 96/03092 A1 | 2/1996 |
| WO | 96/26689 A1 | 9/1996 |
| WO | 97/14375 A1 | 4/1997 |
| WO | 97/25937 A1 | 7/1997 |
| WO | 97/26840 A1 | 7/1997 |
| WO | 97/32543 A1 | 9/1997 |
| WO | 97/32544 A1 | 9/1997 |
| WO | 97/33534 A1 | 9/1997 |
| WO | 97/40780 A1 | 11/1997 |
| WO | 97/40781 A1 | 11/1997 |
| WO | 97/40782 A1 | 11/1997 |
| WO | 97/40783 A2 | 11/1997 |
| WO | 97/40784 A1 | 11/1997 |
| WO | 98/20810 A1 | 5/1998 |
| WO | 98/23228 A1 | 6/1998 |
| WO | 98/36784 A1 | 8/1998 |
| WO | 98/40035 A1 | 9/1998 |
| WO | 98/42278 A1 | 10/1998 |
| WO | 99/01088 A1 | 1/1999 |
| WO | 99/15107 A1 | 4/1999 |
| WO | 99/15108 A2 | 4/1999 |
| WO | 99/23977 A1 | 5/1999 |
| WO | 99/38457 A1 | 8/1999 |
| WO | 99/40876 A2 | 8/1999 |
| WO | 99/40876 A3 | 8/1999 |
| WO | 99/55253 A1 | 11/1999 |
| WO | 00/03661 A1 | 1/2000 |
| WO | 00/06051 | 2/2000 |
| WO | 00/13611 A1 | 3/2000 |
| WO | 00/30563 A1 | 6/2000 |
| WO | 00/62710 A1 | 10/2000 |
| WO | 01/26584 A1 | 4/2001 |
| WO | 01/66036 A2 | 9/2001 |
| WO | 01/91918 A1 | 12/2001 |
| WO | 01/93781 A2 | 12/2001 |
| WO | 02/24112 A2 | 3/2002 |

OTHER PUBLICATIONS

A View of Vascular Stents, by Richard A. Schatz, MD, From the Arizona Heart Institute Foundation, Phoenix, Arizona, Circulation, vol. 79 No. 2, Feb. 1989, pp. 445-457.
Improved Dilation Catheter Balloons, by Stanley B. Levy, Ph.D. Journal of Clinical Engineering, vol. 11, No. 4, Jul.-Aug. 1988, pp. 291-296.
Technical Note Entitled Modifications of Gianturco Expandable Wire Stents, by Barry T. Uchida et al., AJR vol. 150, May 1988, pp. 1185-1187.
Expandable Biliary Endoprosthesis: An Experimental Study, by Carrasco et al., AJR, vol. 145, Dec. 1985, pp. 1279-1282.
Tracheobronchial Tree: Expandable Metallic Stents Used in Experimental and Clinical Applications, Work in Progress, by Wallace et al., Radiology, Feb. 1986, pp. 309-312.
Japanese Infringement Search on Articulated Expandable Stents, Dated Jul. 12, 1995.
Beyer et al., "The BeStent: The Parallel-Serial Jang Stents", Handbook of Coronary Stents, Second Edition, pp. 158-171 & pp. 229-234 (1998).
Beyer et al., "Newer Stents: Materials and Designs", IAGS Proceedings, 9 (5): 363-371 (Jun. 1977).
Roguin et al., "Acute and 30-Day Results of the Serpentine Balloon Expandable Stent Implantation in Simple and Complex Coronary Arterial Narrowings", The American Journal of Cardiology, 80:1155-1162 (Nov. 1997).
Roguin et al., "Be-Stent the Serpentine Balloon Expandable Stent: Review of Mechanical Properties and Clinical Experience", Artif Organs, 22(3): 243-249 (Mar. 1998).
Redacted Public Version: Opening Brief in Support of Cordis' Motion for Summary Judgment of Noninfringement of Claim 36 of the Jang '021 Patent, dated Mar. 31, 2005 (Case No. 03-027-SLR).
Opening Brief in Support of Cordis' Motion for Summary Judgment of Noninfringement of Claim 36 of the Jang '021 Patent, dated Mar. 24, 2005 (Case No. 03-027-SLR).
Reply Brief in Support of Cordis' Motion for Summary Judgment of Noninfringement of Claim 36 of the Jang '021 Patent, dated Apr. 21, 2005 (Case No. 03-027-SLR).
Order, dated Jun. 3, 2005 (Case No. 03-027-SLR).
Jury Verdict, dated Jul. 1, 2005 (Case No. 03-027-SLR and Case No. 03-283-SLR).
Jury Trial—vol. H, BSC v. Cordis & J&J, CA #03-27 & 03-283 (SLR), dated Friday, Jul. 1, 2005, pp. 1816-1857 and Index pp. 1-7.
Jury Trial—vol. A, BSC v. Cordis & J&J, CA #03-27 & 03-283 (SLR), dated Tuesday, Jun. 21, 2005, pp. 1-107 and Index pp. 1-12.
Jury Trial—vol. B, BSC v. Cordis & J&J, CA #03-27 & 03-283 (SLR), dated Wednesday, Jun. 22, 2005, pp. 108-407 and Index pp. 1-32.
Jury Trial—vol. C, BSC v. Cordis & J&J, CA #03-27 & 03-283 (SLR), dated Thursday, Jun. 23, 2005, pp. 408-691 and Index pp. 1-29.
Jury Trial—vol. D, BSC v. Cordis & J&J, CA #03-27 & 03-283 (SLR), dated Friday, Jun. 24, 2005, pp. 693-930 and Index pp. 1-23.
Jury Trial—vol. E, BSC v. Cordis & J&J, CA #03-27 & 03-283 (SLR), dated Jun. 28, 2005, pp. 931-1223.
Under Seal—vol. EE, BSC v. Cordis & J&J, CA #03-27 & 03-283 (SLR), dated Tuesday, Jun. 28, 2005, pp. 1-61 and Index pp. 1-8.
Jury Trial—vol. F, BSC v. Cordis & J&J, CA #03-27 & 03-283 (SLR), dated Wednesday, Jun. 29, 2005, pp. 1224-1537 and Index pp. 1-32.
Jury Trial—vol. G, BSC v. Cordis & J&J, CA #03-27 & 03-283 (SLR), dated Thursday, Jun. 30, 2005, pp. 1538-1815 and Index pp. 1-30.
U.S. Appl. No. 09/999,279, filed Nov. 30, 2001; Inventor: Jansen et al.
U.S. Appl. No. 10/297,372, filed on Dec. 5, 2002; Inventor: Jang.
U.S. Appl. No. 10/321,005, filed Dec. 17, 2002; Inventor: Jang.
U.S. Appl. No. 60/073,412, filed Feb. 2, 1998; Inventor: Jang.
U.S. Appl. No. 60/073,509, filed Feb. 3, 1998; Inventor: Jang.
U.S. Appl. No. 60/234,614, filed Sep. 22, 2000; Inventor: Jang.
U.S. Appl. No. 60/235,115, filed Sep. 25, 2000; Inventor: Jang.
U.S. Appl. No. 60/235,164, filed Sep. 23, 2000; Inventor: Jang.
U.S. Appl. No. 60/017,484, filed Apr. 26, 1996; Inventor: Jang.
U.S. Appl. No. 60/235,167, filed Sep. 23, 2000; Inventor: Jang.
U.S. Appl. No. 60/235,180, filed Sep. 25, 2000; Inventor: Jang.
U.S. Appl. No. 08/845,734, filed Apr. 25, 1997; Inventor: Jang.
Continued videotaped deposition of James E. Moore, Jr., Ph.D., held at the offices of Kirkland & Ellis, LLP, 153 East 53rd Street, New York, New York, pursuant to adjournment, before Cary N. Bigelow, RPR, a Notary Public of the State of New York, dated Mar. 18, 2005, 8:33 a.m. (Case No. 03-027-SLR).
Videotaped deposition of James E. Moore, Jr., Ph.D., held at the offices of Kirkland & Ellis, LLP, 153 East 53rd Street, New York, New York, pursuant to notice, before Cary N. Bigelow, RPR, a Notary Public of the State of New York, dated Mar. 17, 2005, 9:32 a.m. (Case No. 03-027-SLR).
Corrected Rebuttal Expert Report of Professor James E. Moore Jr., Ph.D., dated Mar. 14, 2005 (Case No. 03-027-SLR).
Corrected Expert Report of Professor James E. Moore Jr., Ph.D., dated Feb. 11, 2005 (Case No. 03-027-SLR).

(56) References Cited

OTHER PUBLICATIONS

Opening Expert Report of Nigel Buller, B.SC., M.B., F.R.C.P. regarding Validity of the Jang Patent (Case No. 03-027-SLR), 2005.
Deposition of Nigel Buller, held at the offices of Patterson, Belknap, Webb & Tyler, 1133 Avenue of the Americas, New York, New York, before Laurie A. Collins, a Registered Professional Reporter and Notary Public of the State of New York, dated Mar. 2, 2005, 9:32 a.m. (Case No. 03-027-SLR).
Continued deposition of Nigel Buller, held at the offices of Patterson, Belknap, Webb & Tyler, 1133 Avenue of the Americas, New York, New York, before Laurie A. Collins, a Registered Professional Reporter and Notary Public of the State of New York, dated Mar. 3, 2005, 8:45 a.m. (Case No. 03-027-SLR).
Rebuttal Expert Report of Nigel Buller, B.SC., M.B., F.R.C.P., dated Feb. 25, 2005 (Case No. 03-027-SLR).
Videotaped deposition of the David Morre Parks, Ph.D., a witness called on behalf of the Defendants, pursuant to the Federal Rules of Civil Procedure, before Judith McGovern Williams, Certified Shorthand Reporter No. 130993, Registered Professional Reporter, Certified Realtime Reporter, and Notary Public in and for the Commonwealth of Massachusetts, at the Hyatt Regency, 575 Memorial Drive, Cambridge, Massachusetts, on Monday, Mar. 21, 2005, commencing at 9:32 a.m. (Case No. 03-027-SLR).
Opening Expert Report of David M. Parks, Ph.D. Regarding Validity of the Jang Patent, dated Jan. 28, 2005 (Case No. 03-027-SLR).
Rebuttal Expert Report of David M. Parks, Ph.D., dated Feb. 25, 2005 (Case No. 03-027-SLR).
BSC's Opposition to Cordis' Motion for Summary Judgment of Noninfringement of Claim 36 of the Jang '021 Patent, dated Apr. 14, 2005 (Case No. 03-027-SLR).
Redacted Version—Publicly Filed BSC's Opposition to Cordis' Motion for Summary Judgment of Noninfringement of Claim 36 of the Jang '021 Patent, dated Apr. 14, 2005 (Case No. 03-027-SLR).

* cited by examiner

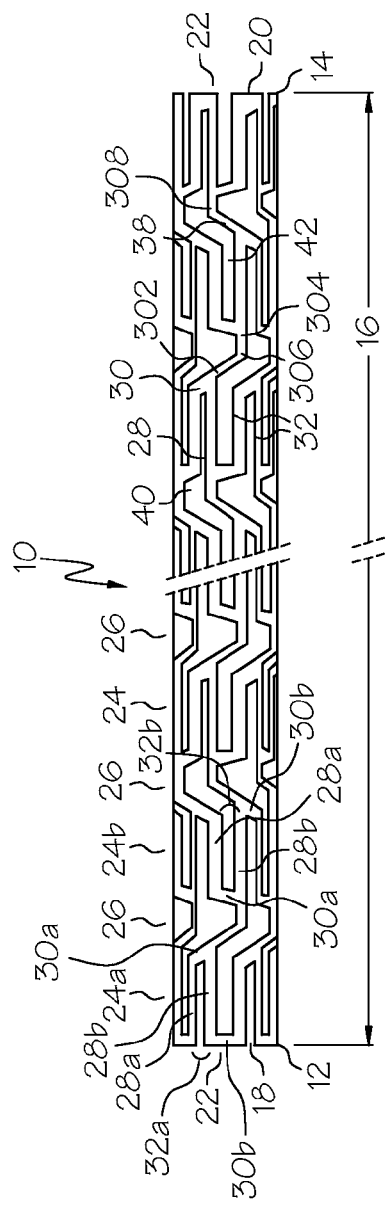
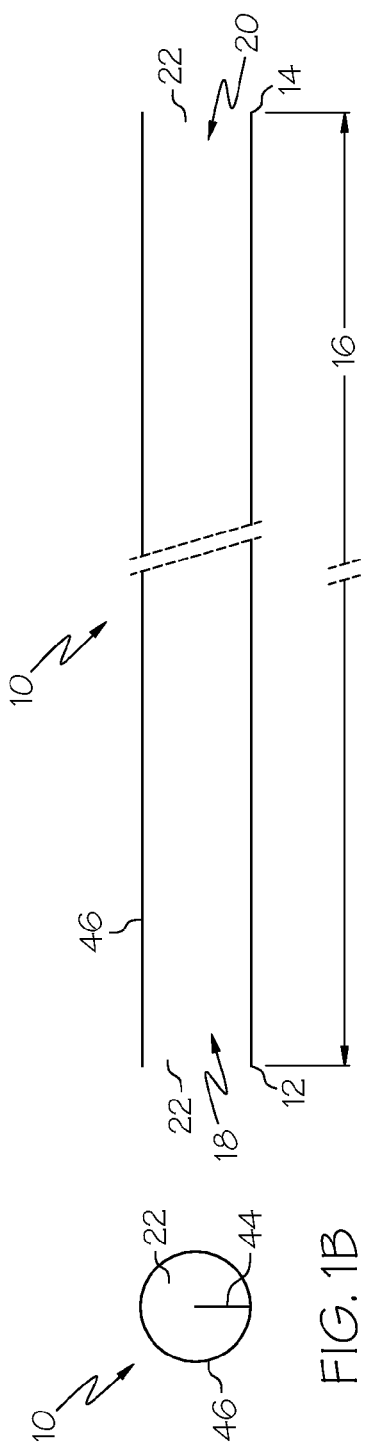

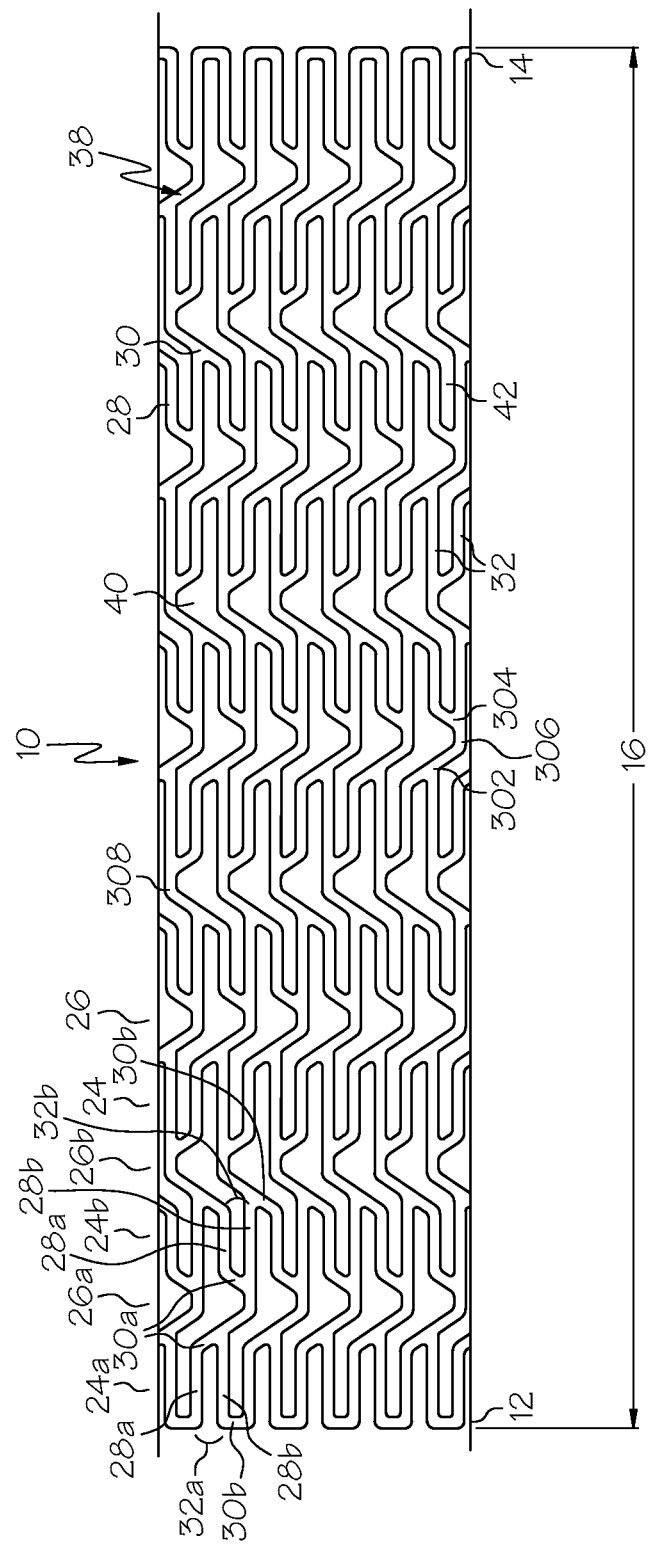

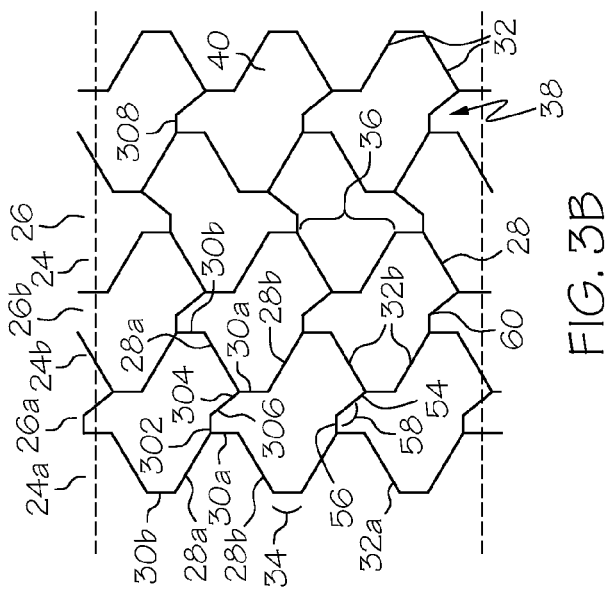
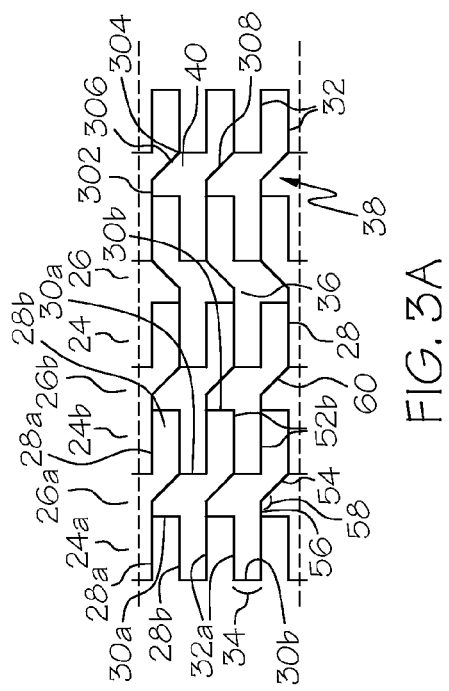

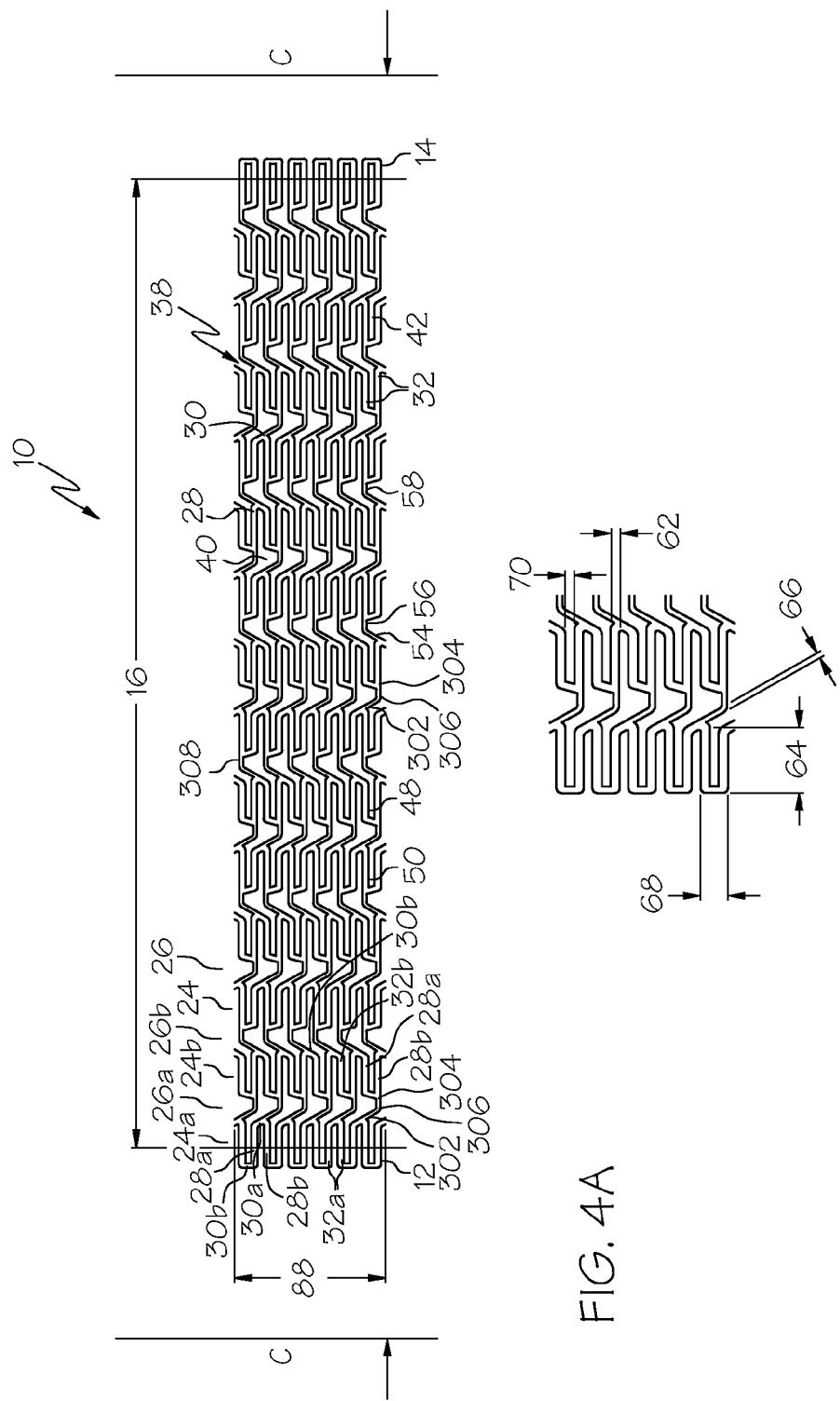

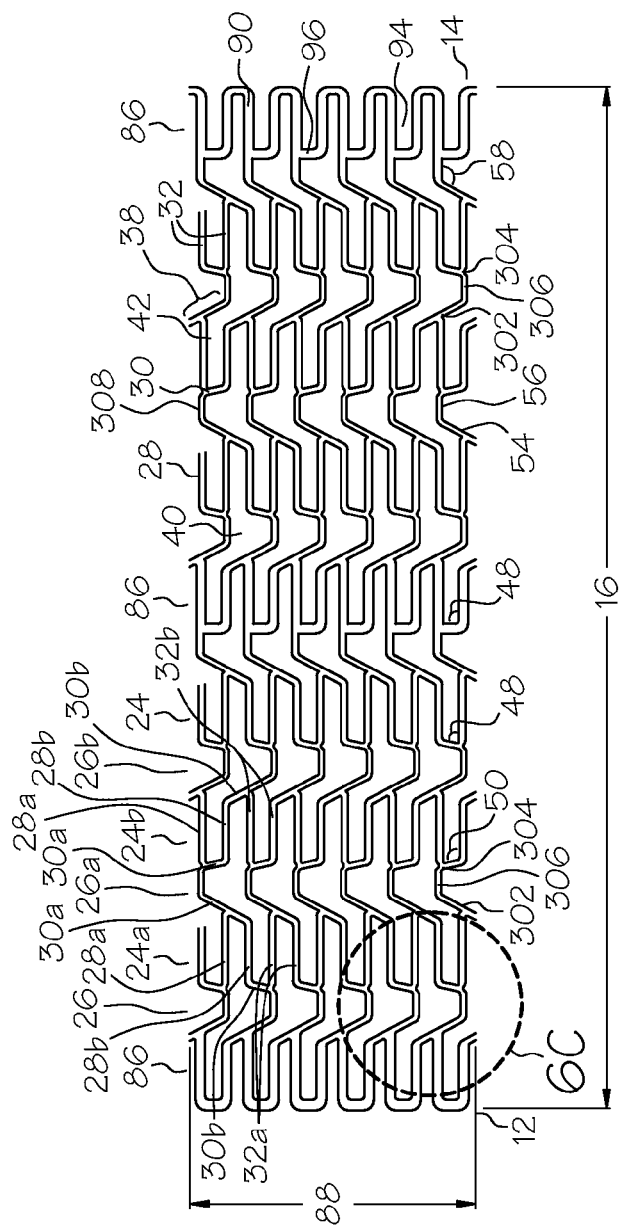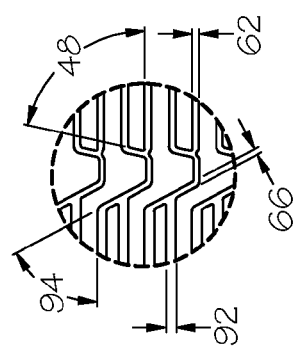
FIG. 6A
FIG. 6C

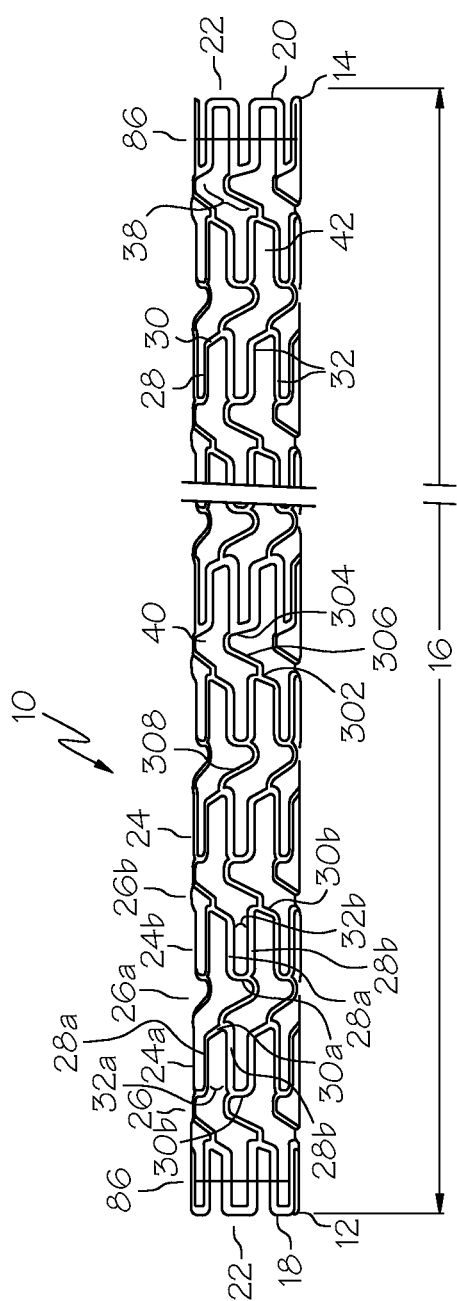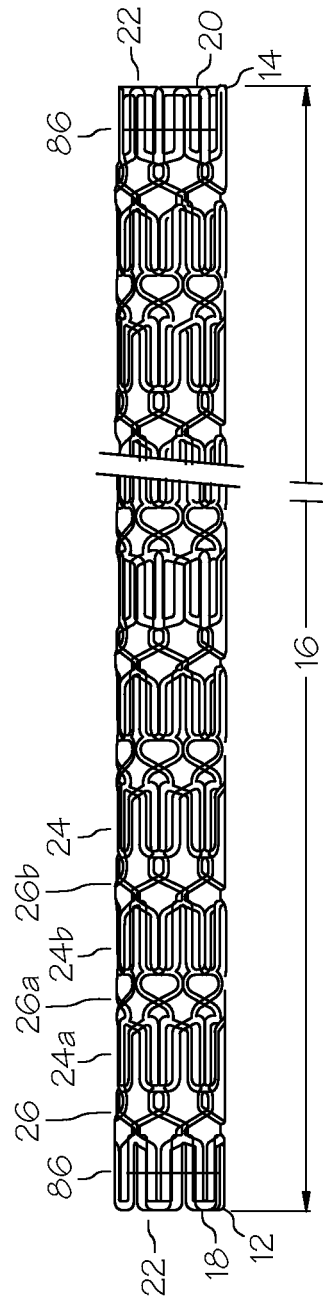
FIG. 8A
FIG. 8B

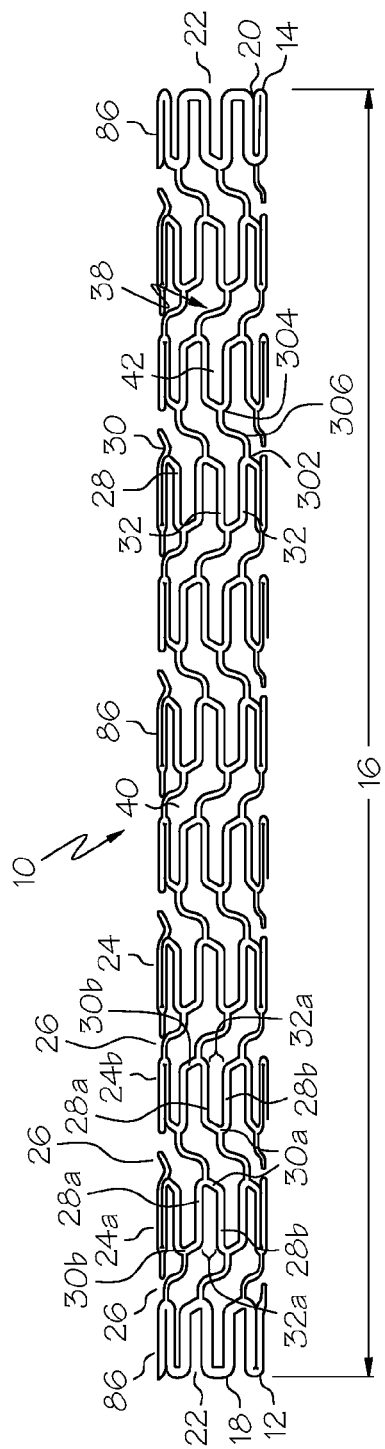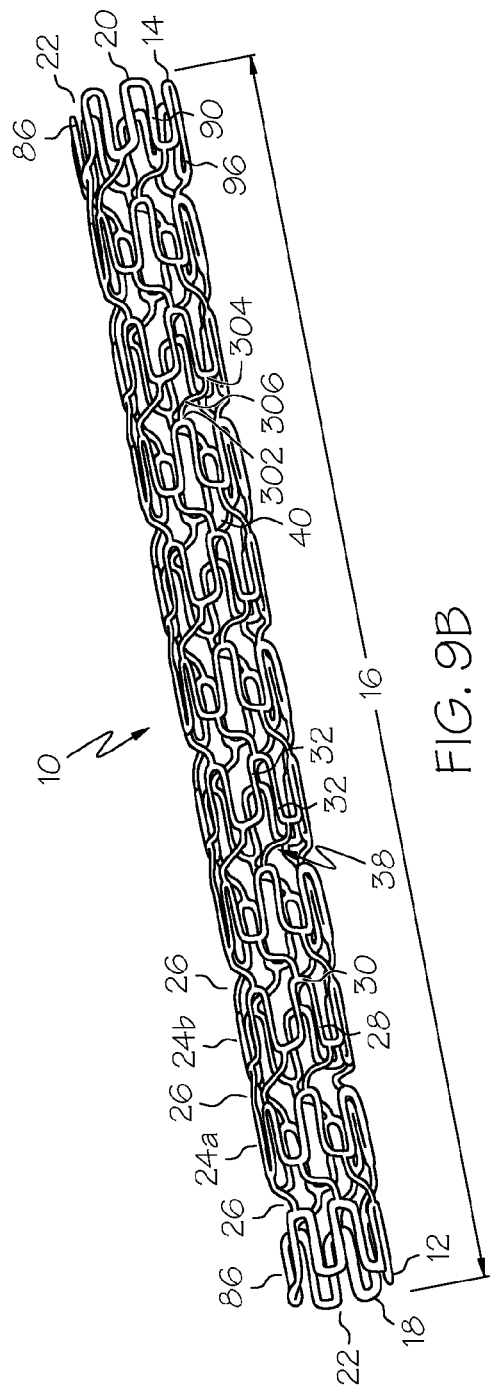

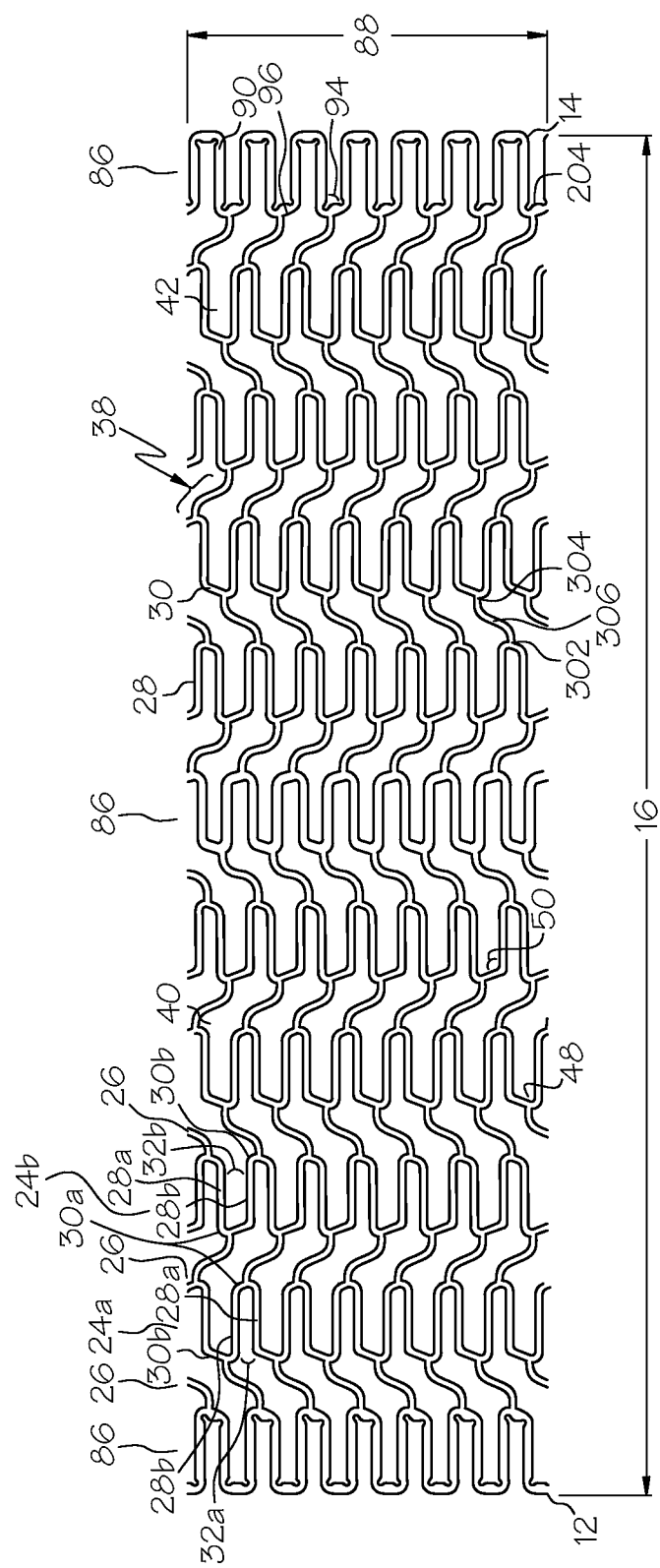

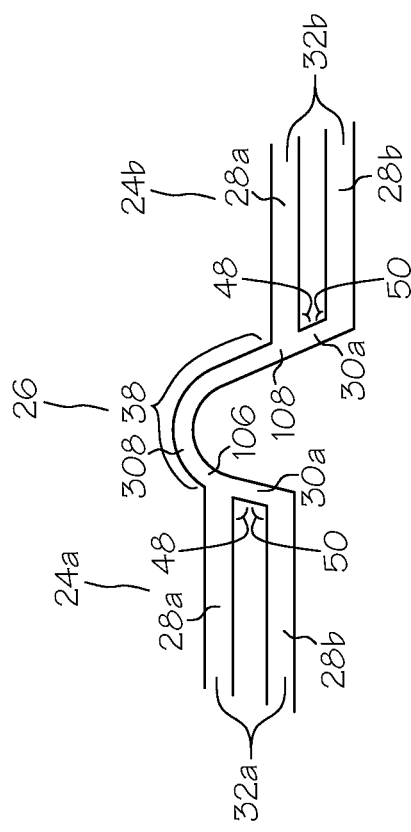
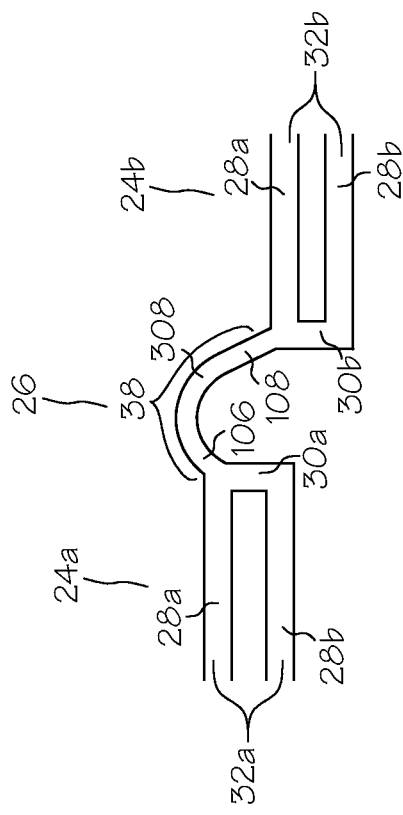

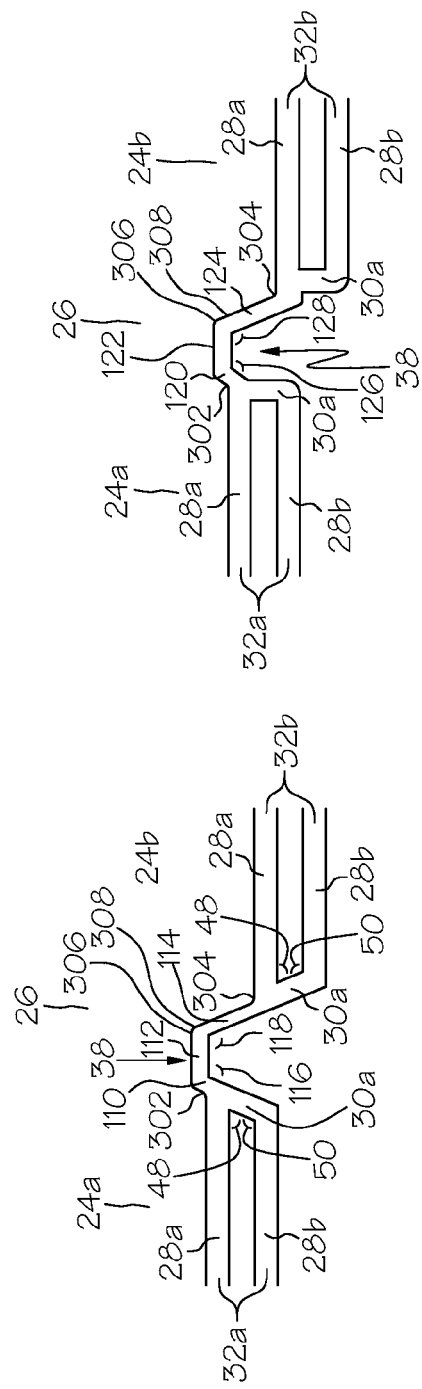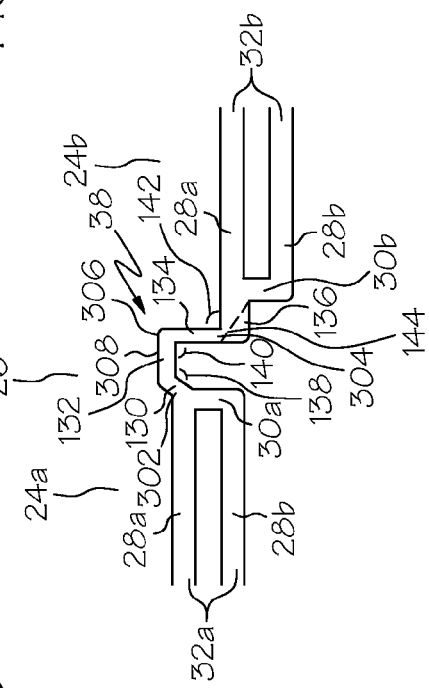
FIG. 10C
FIG. 10D
FIG. 10E

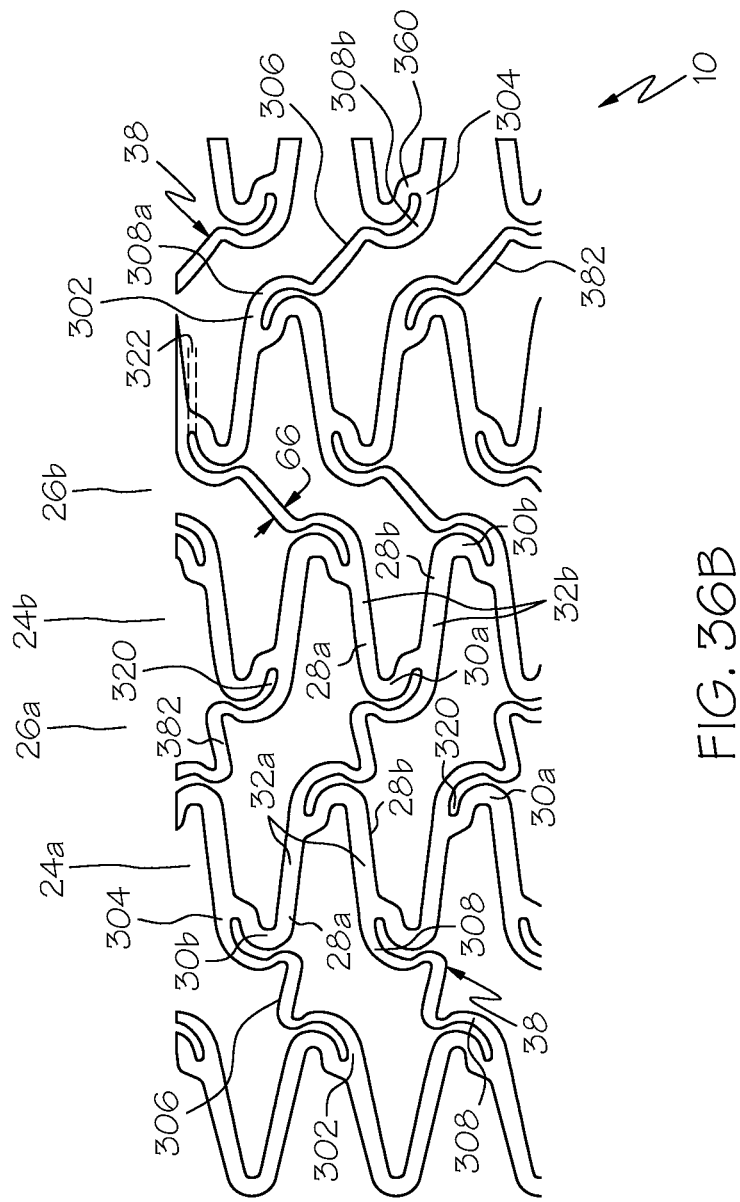

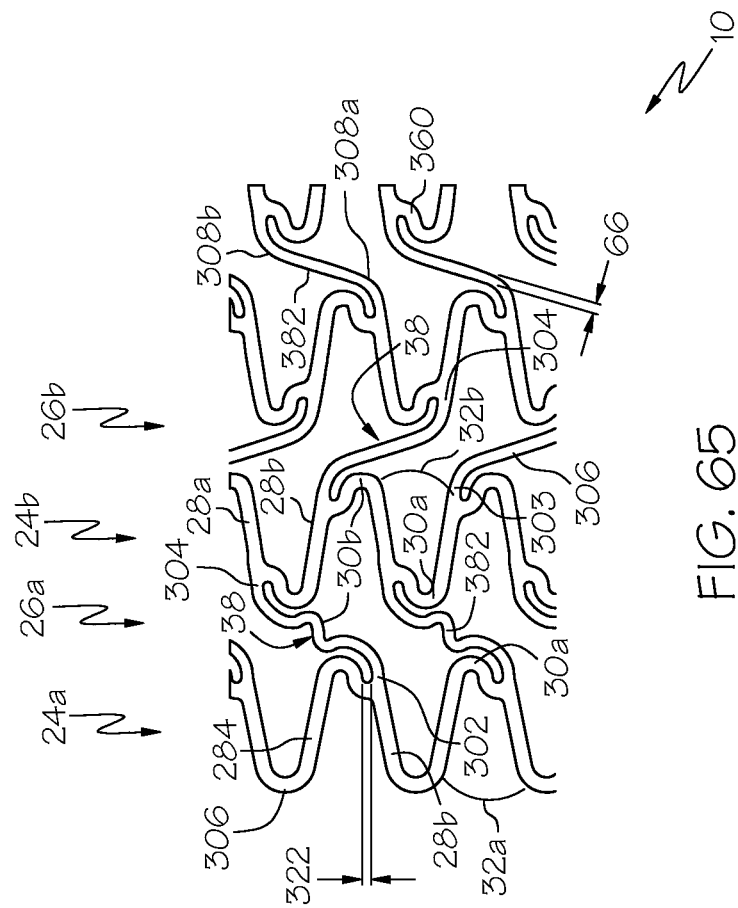

INTRAVASCULAR STENT

CROSS-REFERENCE TO RELATED APPLICATIONS

This application is a continuation of U.S. application Ser. No. 10/374,744, filed Feb. 24, 2003, now abandoned, which is a continuation-in-part of U.S. application Ser. No. 10/206,432 filed Jul. 25, 2002, issued as U.S. Pat. No. 8,021,414, which is a continuation of U.S. application Ser. No. 09/574,077 filed May 18, 2000, issued as U.S. Pat. No. 6,770,088 which is a continuation of U.S. application Ser. No. 08/845,734 filed Apr. 25, 1997, now abandoned which is a continuation-in-part of U.S. application Ser. No. 08/824,142 filed Mar. 25, 1997, issued as U.S. Pat. No. 6,241,760 and which is a continuation-in-part of U.S. application Ser. No. 08/824,866 filed Mar. 26, 1997, issued as U.S. Pat. No. 5,954,743 and which is a continuation-in-part of U.S. application Ser. No. 08/824,865 filed Mar. 26, 1997, issued as U.S. Pat. No. 6,152,957 and which is a continuation-in-part of U.S. application Ser. No. 08/845,657 filed Apr. 25, 1997, issued as U.S. Pat. No. 5,922,021 and which claims benefit of U.S. Provisional Application No. 60/017,484 filed Apr. 26, 1996.

U.S. application Ser. No. 10/374,744, filed Feb. 24, 2003 is also a continuation-in-part of U.S. application Ser. No. 10/123,883 filed Apr. 15, 2002 which is a continuation of U.S. application Ser. No. 09/839,442 filed Apr. 20, 2001, issued as U.S. Pat. No. 6,409,761 which is a continuation of U.S. application Ser. No. 08/824,142 filed Mar. 25, 1997, issued as U.S. Pat. No. 6,241,760 which also claims the benefit of U.S. Provisional Application No. 60/017,484 filed Apr. 26, 1996. U.S. application Ser. No. 10/123,883, from which the present application is a continuation-in-part, is also a continuation of U.S. application Ser. No. 09/839,287 filed Apr. 20, 2001, now abandoned which is a continuation of U.S. application Ser. No. 09/237,537 filed Jan. 26, 1999, issued as U.S. Pat. No. 6,235,053 which claims benefit of U.S. Provisional Application No. 60/073,412 filed Feb. 2, 1998.

U.S. application Ser. No. 10/374,744, filed Feb. 24, 2003 is also continuation-in-part of U.S. application Ser. No. 10/321,005 filed Dec. 17, 2002 which is a continuation of U.S. application Ser. No. 09/839,287 filed Apr. 20, 2001, now abandoned which is a continuation of U.S. application Ser. No. 09/237,537 filed Jan. 26, 1999, issued as U.S. Pat. No. 6,235,053 which claims benefit of U.S. Provisional Application No. 60/073,412 filed Feb. 2, 1998.

U.S. application Ser. No. 10/374,744, filed Feb. 24, 2003 is also a continuation-in-part of U.S. application Ser. No. 09/960,861 filed Sep. 21, 2001, now abandoned which claims benefit of U.S. Provisional Application No. 60/234,614 filed Sep. 22, 2000.

U.S. application Ser. No. 10/374,744, filed Feb. 24, 2003 is also a continuation-in-part of U.S. application Ser. No. 09/874,349 filed Jun. 4, 2001, issued as U.S. Pat. No. 6,783,543 which claims priority to U.S. Provisional Application No. 60/209,255 filed Jun. 5, 2000. U.S. application Ser. No. 10/374,744, filed Feb. 24, 2003 is also a continuation-in-part of U.S. application Ser. No. 10/297,372 filed Dec. 5, 2002, which is a national stage application from International Application No. PCT/US01/18419 filed Jun. 5, 2001, which claims priority to U.S. Provisional Application No. 60/209,255 filed Jun. 5, 2000.

U.S. application Ser. No. 10/374,744, filed Feb. 24, 2003 is also a continuation-in-part of U.S. application Ser. No. 09/942,077 filed Aug. 28, 2001, now abandoned which claims benefit of U.S. Provisional Application No. 60/235,164 filed Sep. 23, 2000.

The contents of all U.S. patents and applications cited above are incorporated herein by reference in their entirety.

STATEMENT REGARDING FEDERALLY SPONSORED RESEARCH

Not Applicable

BACKGROUND OF THE INVENTION

Stents, grafts, stent-grafts, vena cava filters and similar implantable medical devices, collectively referred to hereinafter as stents, are radially expandable endoprostheses which are typically intravascular implants capable of being implanted transluminally and enlarged radially after being introduced percutaneously. Stents may be implanted in a variety of body lumens or vessels such as within the vascular system, urinary tracts, bile ducts, etc. Stents may be used to reinforce body vessels and to prevent restenosis following angioplasty in the vascular system. They may be self-expanding, mechanically expandable or hybrid expandable.

Stents are generally tubular devices for insertion into body lumens. However, it should be noted that stents may be provided in a wide variety of sizes and shapes. Balloon expandable stents require mounting over a balloon, positioning, and inflation of the balloon to expand the stent radially outward. Self-expanding stents expand into place when unconstrained, without requiring assistance from a balloon. A self-expanding stent is biased so as to expand upon release from the delivery catheter. Some stents may be characterized as hybrid stents which have some characteristics of both self-expandable and balloon expandable stents.

Due to the branching nature of the human vasculature it is not uncommon for stenoses to form at any of a wide variety of vessel bifurcations. A bifurcation is an area of the vasculature or other portion of the body where a first (or parent) vessel is bifurcated into two or more branch vessels. In some cases it may be necessary to implant multiple stents at the bifurcation in order to address a stenosis located thereon. Alternatively, a stent may be provided with multiple sections or branches that may be deployed within the branching vessels of the bifurcation.

Stents may be constructed from a variety of materials such as stainless steel, Elgiloy, nickel, titanium, nitinol, shape memory polymers, etc. Stents may also be formed in a variety of manners as well. For example a stent may be formed by etching or cutting the stent pattern from a tube or section of stent material; a sheet of stent material may be cut or etched according to a desired stent pattern whereupon the sheet may be rolled or otherwise formed into the desired substantially tubular, bifurcated or other shape of the stent; one or more wires or ribbons of stent material may be woven, braided or otherwise formed into a desired shape and pattern.

Typically, a stent is implanted in a blood vessel or other body lumen at the site of a stenosis or aneurysm by so-called "minimally invasive techniques" in which the stent is compressed radially inwards and is delivered by a catheter to the site where it is required through the patient's skin or by a "cut down" technique in which the blood vessel concerned is exposed by minor surgical means. When the stent is positioned at the correct location, the catheter is withdrawn and the stent is caused or allowed to expand to a predetermined diameter in the vessel.

Despite the wide variety of stents presently available, there remains a desire to provide stents and stent designs which provide a more optimized combination of improved flexibility and good vessel coverage.

All US patents and applications and all other published documents mentioned anywhere in this application are incorporated herein by reference in their entirety.

Without limiting the scope of the invention a brief summary of some of the claimed embodiments of the invention is set forth below. Additional details of the summarized embodiments of the invention and/or additional embodiments of the invention may be found in the Detailed Description of the Invention below.

A brief abstract of the technical disclosure in the specification is provided as well only for the purposes of complying with 37 C.F.R. 1.72. The abstract is not intended to be used for interpreting the scope of the claims.

BRIEF SUMMARY OF THE INVENTION

In light of the above the present invention is directed to a variety of embodiments. In at least one embodiment a stent is provided that provides a more optimized combination of flexibility and vessel coverage. In some embodiments the stent is balloon expandable. In some embodiments the stent is self-expandable. In some embodiments the stent is hybrid expandable.

In at least one embodiment the stent is provided with a smooth surface modulation that minimizes tulips.

In at least one embodiment at least a portion of the stent is radiopaque.

In at least one embodiment the stent is at least partially constructed from a shape memory alloy, polymer and/or other shape memory material.

In at least one embodiment the stent is at least partially constructed from nitinol, stainless steel, or other metal.

In at least one embodiment the stent is at least partially constructed from a polymer material and/or is at least partially coated with one or more polymer materials.

In at least one embodiment the stent is provided with a biocompatible coating.

In at least one embodiment of the invention the stent is provided with one or more of a variety of patterns or configurations of interconnected struts, connectors and/or stent members.

In some embodiments the stent is provided with a desired stent pattern by cutting, ablating, shaping or otherwise modifying a substantially tubular member.

In some embodiments the stent is provided with a desired stent pattern by cutting, ablating, shaping or otherwise modifying a sheet of suitable material. The sheet may then be rolled upon it itself and the edges of the rolled sheet may be engaged to one another in an abutting or overlapping configuration.

In some embodiments the stent is formed from one or more moulds.

In at least one embodiment the invention is directed to a stent comprising a first expansion strut column. The first expansion strut column is comprised of a plurality of adjacent first expansion strut pairs, wherein each first expansion strut pair has a first expansion strut and a second expansion strut. The first expansion strut column has a plurality of first joining portions. The first expansion strut is in communication with the second expansion strut at a first joining portion. The first expansion strut column has a plurality of second joining portions, wherein each first expansion strut pair is in communication with an adjacent first expansion strut pair at each second joining portion.

The stent further comprises a second expansion strut column. The second expansion strut column is comprised of a plurality of adjacent second expansion strut pairs, wherein each second expansion strut pair has a first expansion strut and a second expansion strut. The second expansion strut column has a plurality of first joining portions. The first expansion strut is in communication with the second expansion strut at a first joining portion. The second expansion strut column has a plurality of second joining portions, wherein each second expansion strut pair is in communication with an adjacent second expansion strut pair at each second joining portion.

The stent further comprises a first connecting strut column. The first connecting strut column comprises at least one connecting strut, wherein the at least one connecting strut is comprised of a first end region, a second end region and an intermediate region therebetween. The first end region is engaged to a portion of one of the first expansion strut pairs at a location in closer proximity to the first expansion strut than to the second expansion strut. The intermediate region comprises a plurality of bend portions. At least a portion of the at least one connecting strut comprises at least one wrap portion, wherein the at least one wrap portion is at least partially wrapped about at least one of the first joining portions of at least one of the first expansion strut column and the second expansion strut column.

In some embodiments the second end region of the at least one connecting strut is engaged to a portion of one of the second expansion strut pairs at a location in closer proximity to the first expansion strut than to the second expansion strut.

In some embodiments the second end region is engaged to a portion of one of the second expansion strut pairs at a location substantially equal in proximity to the first expansion strut than to the second expansion strut.

In some embodiments the stent of claim further comprises a third expansion strut column and a second connecting strut column. The third expansion strut column is comprised of a plurality of adjacent third expansion strut pairs. Each third expansion strut pair has a first expansion strut and a second expansion strut. The third expansion strut column has a plurality of first joining portions. The first expansion strut is in communication with the second expansion strut at a first joining portion. The second expansion strut column has a plurality of second joining portions. Each third expansion strut pair is in communication with an adjacent third expansion strut pair at each second joining portion. The second connecting strut column comprises at least one connecting strut. The at least one connecting strut comprises a first end region, a second end region and an intermediate region therebetween. The first end region is engaged to a portion of one of the second expansion strut pairs at a location in closer proximity to the first expansion strut than to the second expansion strut. The intermediate region comprises a plurality of bend portions. At least a portion of the at least one connecting strut comprises at least one wrap portion. The at least one wrap portion is at least partially wrapped about at least one of the second joining portions of the second expansion strut column and the first joining portions of the third expansion strut column.

In some embodiments the second end region of the at least one connecting strut of the second connecting strut column is engaged to a portion of one of the third expansion strut pairs at a location in closer proximity to the first expansion strut than to the second expansion strut.

In some embodiments the second end region of the at least one connecting strut of the second connecting strut column is engaged to a portion of one of the second expansion strut pairs at a location substantially equal in proximity to the first expansion strut than to the second expansion strut.

In some embodiments the intermediate region of the at least one connecting strut of the first connecting strut column further comprises at least one substantially linear portion to at least six substantially linear portions.

In some embodiments the intermediate region of the at least one connecting strut of the second connecting strut column further comprises at least one substantially linear portion to at least six substantially linear portions.

In some embodiments each substantially liner portion intersects an adjacent substantially linear portion at one of the bend portions.

In some embodiments the at least one connecting strut comprises a single wrap portion, wherein the wrap portion is at least partially wrapped about at least one of the first joining portions of the first expansion strut column or one of the first joining portions of the second expansion strut column.

In some embodiments the at least one connecting strut comprises a first wrap portion and a second wrap portion, the first wrap portion being at least partially wrapped about at least one of the first joining portions of the first expansion strut column, the second wrap portion is at least partially wrapped about at least one of the first joining portions of the second expansion strut column.

In some embodiments the at least one wrap portion and the at least one first joining portion define a slot region, the slot region having a slot region width, the at least one connecting strut having a connecting strut width, the slot region width is less than the connecting strut width.

In some embodiments the slot region width is about 0.0025 inch and the connecting strut width is about 0.0030 inch.

In some embodiments the slot region width is about 0.0015 inches and the connecting strut width is 0.002 inch or greater In some embodiments the at least one wrap portion is substantially parallel to the first joining portion about which the at least one wrap portion is wrapped.

In some embodiments the at least one wrap portion is an extension of at least one of the first expansion strut and the second expansion strut of the first expansion strut pair and/or the second expansion strut pair.

In some embodiments the at least one connecting strut of the first connecting strut column and the at least one connecting strut of the second connecting strut column has a different shape from one another.

In some embodiments the at least one connecting strut of the first connecting strut column and the at least one connecting strut of the second connecting strut column has a different length from one another.

In some embodiments the at least one connecting strut of the first connecting strut column and the at least one connecting strut of the second connecting strut column has substantially the same length.

In some embodiments the at least one connecting strut of the first connecting strut column has a first connecting strut width and the at least one connecting strut of the second connecting strut column has a second connecting strut width, the first connecting strut width and the second connecting strut width are different from one another.

In some embodiments the at least one connecting strut of the first connecting strut column has a first connecting strut width and the at least one connecting strut of the second connecting strut column has a second connecting strut width, the first connecting strut width and the second connecting strut width are substantially the same.

In some embodiments the intermediate region of the at least one connecting strut comprises at least two to at least six bend portions.

In some embodiments the first end region of the at least one connecting strut is engaged to a first expansion strut pair at an intersection of the first expansion strut and the first joining portion of the first expansion strut pair.

In some embodiments the first end region of the at least one connecting strut is engaged to a first expansion strut pair at an intersection of the second expansion strut and the first joining portion of the first expansion strut pair.

In some embodiments the first end region of the at least one connecting strut is engaged to the first expansion strut pair at a location adjacent to an intersection of the first expansion strut and the first joining portion of the first expansion strut pair.

In some embodiments the first end region of the at least one connecting strut is engaged to the first expansion strut pair at a location adjacent to an intersection of the second expansion strut and the first joining portion of the first expansion strut pair.

In some embodiments at least a portion of the at least one connecting strut is substantially parallel to the first expansion strut of the first expansion strut pair to which the at least one connecting strut is engaged.

In some embodiments at least a portion of the at least one connecting strut is substantially parallel to the first joining portion of the first expansion strut pair to which the at least one connecting strut is engaged.

In some embodiments at least a portion of the at least one connecting strut is substantially parallel to the second expansion strut of the first expansion strut pair to which the at least one connecting strut is engaged.

In some embodiments the second end region of the at least one connecting strut is engaged to a second expansion strut pair at an intersection of the first expansion strut and the first joining portion of the second expansion strut pair.

In some embodiments the second end region of the at least one connecting strut is engaged to a second expansion strut pair at an intersection of the second expansion strut and the first joining portion of the first expansion strut pair.

In some embodiments the second end region of the at least one connecting strut is engaged to a second expansion strut pair at a location adjacent to an intersection of the first expansion strut and the first joining portion of the second expansion strut pair.

In some embodiments the second end region of the at least one connecting strut is engaged to a second expansion strut pair at a location adjacent to an intersection of the second expansion strut and the first joining portion of the second expansion strut pair.

In some embodiments at least a portion of the at least one connecting strut is substantially parallel to the first expansion strut of the second expansion strut pair to which the at least one connecting strut is engaged.

In some embodiments at least a portion of the at least one connecting strut is substantially parallel to the first joining portion of the second expansion strut pair to which the at least one connecting strut is engaged.

In some embodiments at least a portion of the at least one connecting strut is substantially parallel to the second expansion strut of the second expansion strut pair to which the at least one connecting strut is engaged.

In some embodiments the at least one wrap portion of the at least one connecting strut extends longitudinally and circumferentially away from the first expansion strut pair to which the at least one connecting strut is engaged.

In some embodiments the at least one wrap portion of the at least one connecting strut extends longitudinally and circumferentially away from the second expansion strut pair to which the at least one connecting strut is engaged.

In some embodiments at least a portion of the first expansion strut and at least a portion of the second expansion strut of each first expansion strut pair are substantially parallel.

In some embodiments at least a portion of the first expansion strut and the at least a portion of the second expansion strut are not parallel to a longitudinal axis of the stent.

In some embodiments at least a portion of the first expansion strut and at least a portion of the second expansion strut of each second expansion strut pair are substantially parallel.

In some embodiments at least a portion of at least one of the first expansion strut and the second expansion strut of each first expansion strut pair and/or second expansion strut pair are substantially parallel to a longitudinal axis of the stent.

In some embodiments at least one of the first expansion strut and the second expansion strut of a first expansion strut pair and/or second expansion strut pair comprise at least one stepped notch.

In some embodiments the first end region and/or the second end region of the at least one connecting strut is engaged to the at least one stepped notch.

In some embodiments the first end region and the second end region of the at least one connecting strut have an ipsilateral orientation relative to one another.

In some embodiments the first end region and the second end region of the at least one connecting strut have a contra-lateral orientation relative to one another.

In some embodiments at least two connecting struts of the first connecting strut column and a first expansion strut pair and a second expansion strut pair respectively engaged each thereto form an asymmetrical cell space.

In some embodiments at least two connecting struts of the first connecting strut column and a first expansion strut pair and a second expansion strut pair respectively engaged each thereto define a cell perimeter about the asymmetrical cell space. In at least one embodiment the cell perimeter is at least 5 mm in length. In at least one embodiment the cell perimeter is at least 7 mm in length. In some embodiments the cell perimeter is about 8 mm or more.

In some embodiments the stent comprises at least one radiopaque marker.

In some embodiments at least one of the first connecting strut pairs is configured to retain the at least one radiopaque marker.

In some embodiments at least one of the second connecting strut pairs is configured to retain the at least one radiopaque marker.

In some embodiments the at least one radiopaque marker is selected from at least one member of the group consisting of: at least one radiopaque rivet, at least one radiopaque band, at least one radiopaque coating and any combinations thereof.

In some embodiments at least one of the first expansion strut and second expansion strut of a first expansion strut pair having at least one expansion strut bend.

In some embodiments at least one of the first expansion strut and second expansion strut of a second expansion strut pair having at least one expansion strut bend.

In some embodiments the first end region and/or the second end region of the at least one connecting strut is engaged to the at least one expansion strut bend.

In some embodiments each first expansion strut pair of the first expansion strut column is both circumferentially and longitudinally offset relative to the second expansion strut pair of the second expansion strut column to which the first expansion strut pair is connected.

In some embodiments each first expansion strut pair of the first expansion strut column is only longitudinally offset relative to the second expansion strut pair of the second expansion strut column to which the first expansion strut pair is connected.

In some embodiments the at least one wrap portion of the at least one connecting strut has at least one substantially linear section.

In some embodiments the at least one substantially linear section of the wrap portion is engaged to a stepped notch of one of the first expansion strut and second expansion strut.

In some embodiments the at least one substantially linear section of the wrap portion and the first expansion strut or second expansion strut to which it is engaged are substantially parallel.

In some embodiments the at least one substantially linear section of the wrap portion and the first expansion strut or second expansion strut to which it is engaged define an angle of about 180 to about 135 degrees. In at least one embodiment the angle is about 170 degrees or more.

In some embodiments the at least one substantially linear section of the at least one wrap portion extends laterally away from the stepped notch.

In some embodiments the at least one wrap portion of the at least one connecting strut comprises a first substantially linear section of the at least one connecting strut, the first substantially linear section extends longitudinally away from the first expansion strut pair to which it is engaged. A second substantially linear section of the at least one connecting strut extends from the first substantially linear section in a direction toward the first joining portion of the first expansion strut pair. In at least one embodiment a third section extends from the second substantially linear section in a direction toward the second expansion strut pair to which the at least one connecting strut is engaged. In at least on embodiment the first substantially linear section is engaged to a stepped notch of one of the first expansion strut and second expansion strut of the first expansion strut pair. In at least one embodiment the third substantially linear section is engaged to a stepped notch of one of the first expansion strut and second expansion strut of the second expansion strut pair.

In some embodiments the intermediate portion of the at least one connecting strut is further comprised of at least two substantially linear sections, the at least two substantially linear sections intersecting at an intersection, the intersection of the at least two substantially linear portions defines a slant angle. In at least one embodiment the slant angle is obtuse.

In some embodiments the intermediate portion of the at least one connecting strut is further comprised of at least two substantially linear sections, the at least two substantially linear sections intersecting at an intersection, the intersection of the at least two substantially linear portions defines a radius of curvature.

In some embodiments the stent is configured to deliver at least one therapeutic agent. In at least one embodiment the at least one therapeutic agent is one or more coatings. In at least one embodiment the at least one therapeutic agent is a non-genetic agent, a genetic agent, cellular material, one or more polymer coatings, and or any combinations thereof.

In some embodiments the stent is provided with a plurality of cavities. In at least on embodiment at least one of the plurality of cavities extend through at least one of the first expansion strut, the second expansion strut, the first joining portion, the second joining portion, and the at least one connecting strut. In at least one embodiment at least one of the plurality of cavities extends only partially through at least one of the first expansion strut, the second expansion strut, the first joining portion, the second joining portion, and the at least one connecting strut.

In some embodiments the invention is directed to a stent delivery system comprising a stent delivery catheter for delivering the stent. In at least one embodiment the catheter comprises a balloon.

In some embodiments the stent comprises a plurality of substantially serpentine bands including a first substantially serpentine band and a second substantially serpentine band. The first substantially serpentine band and the second substantially serpentine band are connected by at least one connection member. The first substantially serpentine band has a plurality of first end portions and a plurality of second end portions. The second substantially serpentine band has a plurality of first end portions and a plurality of second end portions. The at least one connection member comprising at least one wrap portion, wherein the at least one wrap portion extends away from one of the plurality first end potions and wraps around at least a portion of the first end portion from which it extends. The at least one connection member having a plurality of bends.

These and other embodiments which characterize the invention are pointed out with particularity in the claims annexed hereto and forming a part hereof. However, for a better understanding of the invention, its advantages and objectives obtained by its use, reference should be made to the drawings which form a further part hereof and the accompanying descriptive matter, in which there is illustrated and described a embodiments of the invention.

BRIEF DESCRIPTION OF THE SEVERAL
VIEWS OF THE DRAWING(S)

A detailed description of the invention is hereafter described with specific reference being made to the drawings.

FIG. 1A is a side elevation view of the pre-expansion mode of an embodiment of the stent of the present invention.

FIG. 1B is a cross sectional view of an embodiment of the stent of the present invention.

FIG. 1C is a longitudinal cross sectional view of an embodiment of the stent of the present invention.

FIG. 2A is a scale drawing of the strut pattern of an embodiment of the stent of the present invention.

FIG. 3A is a schematic illustration of a pre-expansion mode of an embodiment of the stent of the present invention.

FIG. 3B is a schematic illustration of the post-expansion mode of an embodiment of the stent of the present invention.

FIG. 4A is a scale drawing including dimensions of an embodiment of the stent of the present invention.

FIG. 4B is an enlarged section of the scale drawing of FIG. 4A.

FIG. 6A is a scale drawing of an embodiment of the stent of the present invention with reinforcement expansion columns.

FIG. 6C is an enlarged region of the embodiment of FIG. 6A.

FIG. 8A is a side elevation view of an embodiment of the stent of the present invention.

FIG. 8B is a side elevation view of an embodiment of the stent of the present invention, shown as if the stent struts and space there between were transparent.

FIG. 9A is a side elevation view of an embodiment of the stent of the present invention.

FIG. 9B is a perspective view of the embodiment of FIG. 9A.

FIG. 9C is a scale drawing of the embodiment of FIG. 9A.

FIG. 10A is a drawing of an alternate geometry of connecting struts and joining struts in accord with the present invention.

FIG. 10B is a drawing of an alternate geometry of connecting struts and joining struts in accord with the present invention.

FIG. 10C is a drawing of an alternate geometry of connecting struts and joining struts in accord with the present invention.

FIG. 10D is a drawing of an alternate geometry of connecting struts and joining struts in accord with the present invention.

FIG. 10E is a drawing of an alternate geometry of connecting struts and joining struts in accord with the present invention.

Figure 19:
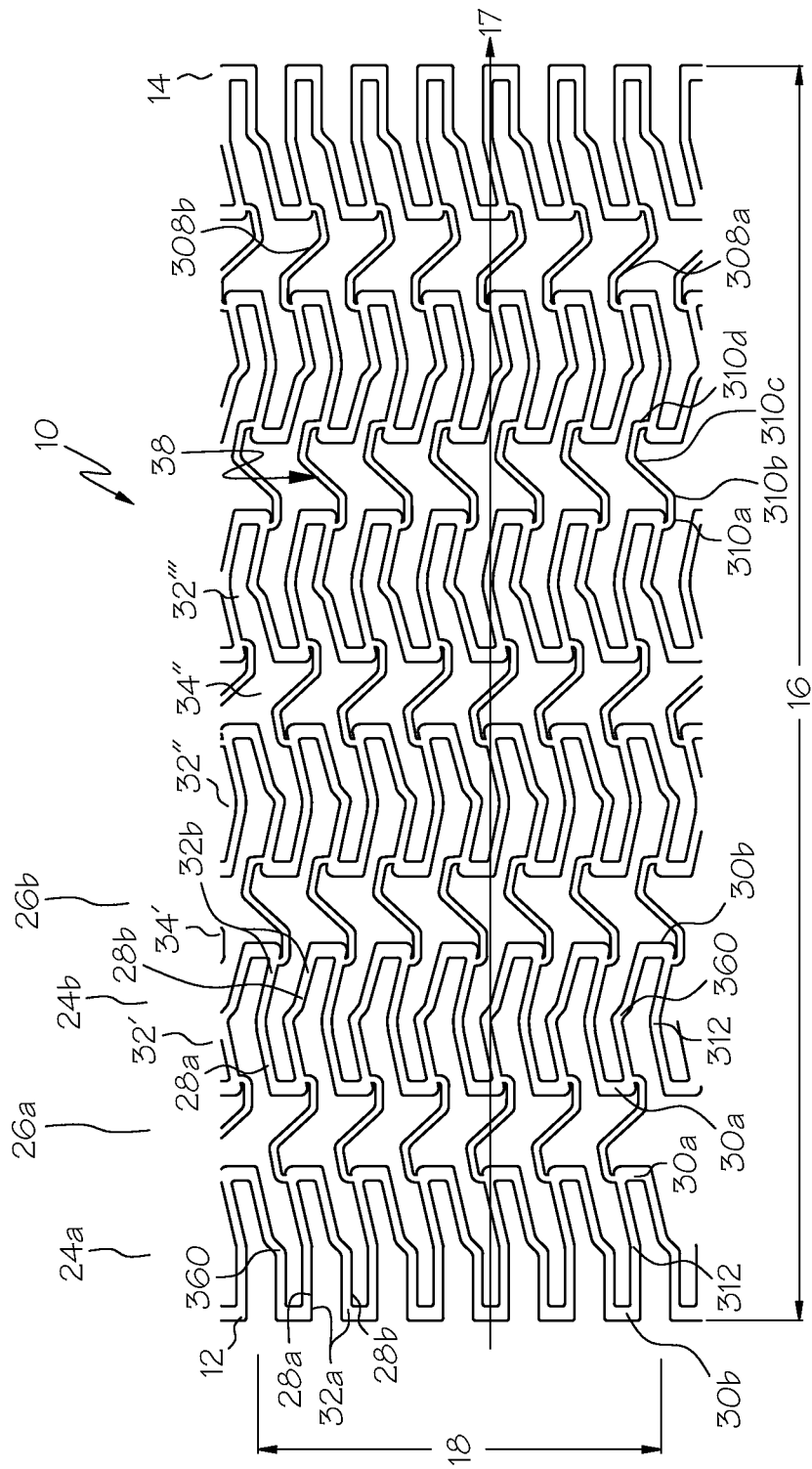
Figure 20:
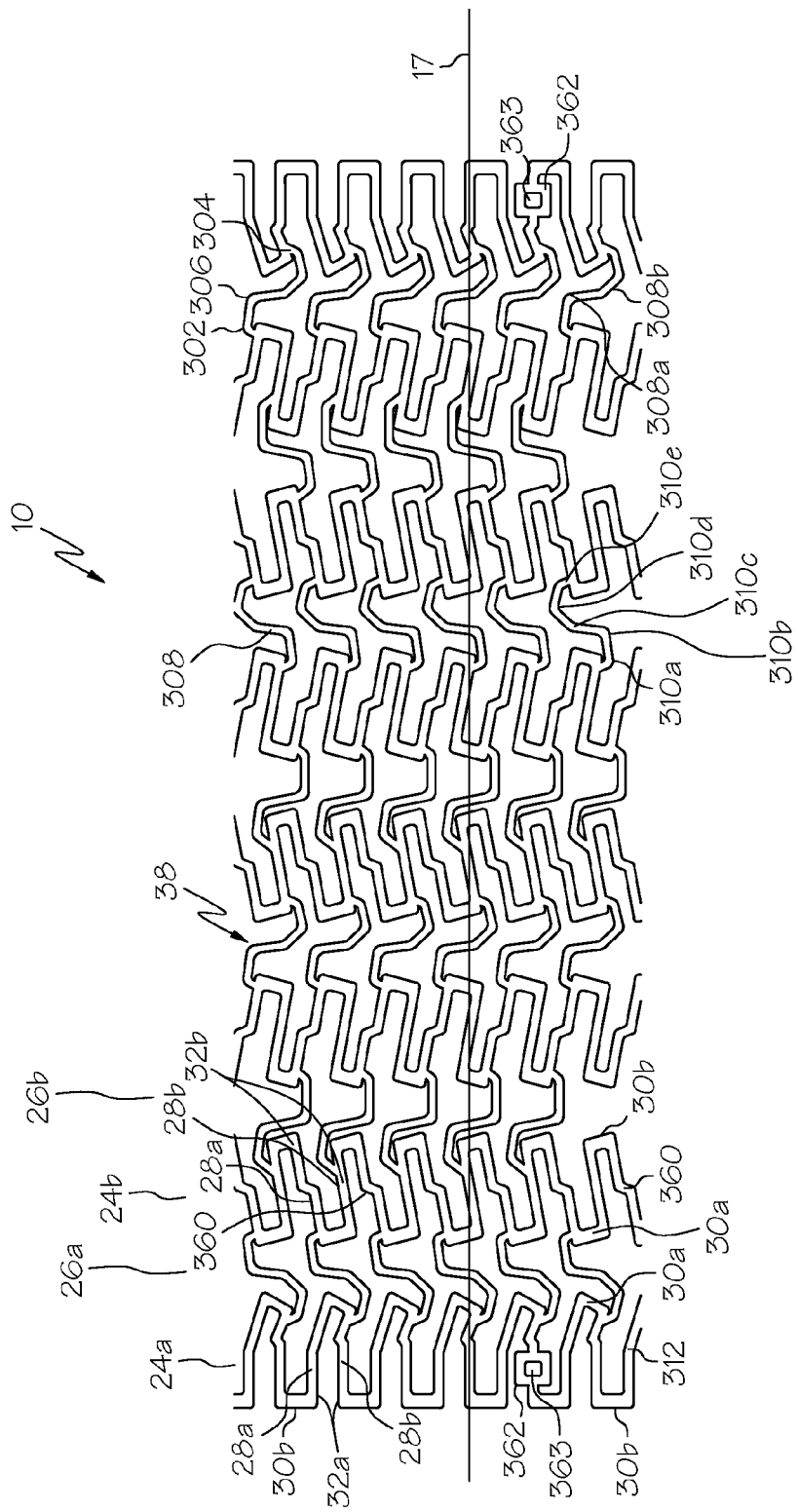
Figure 21:
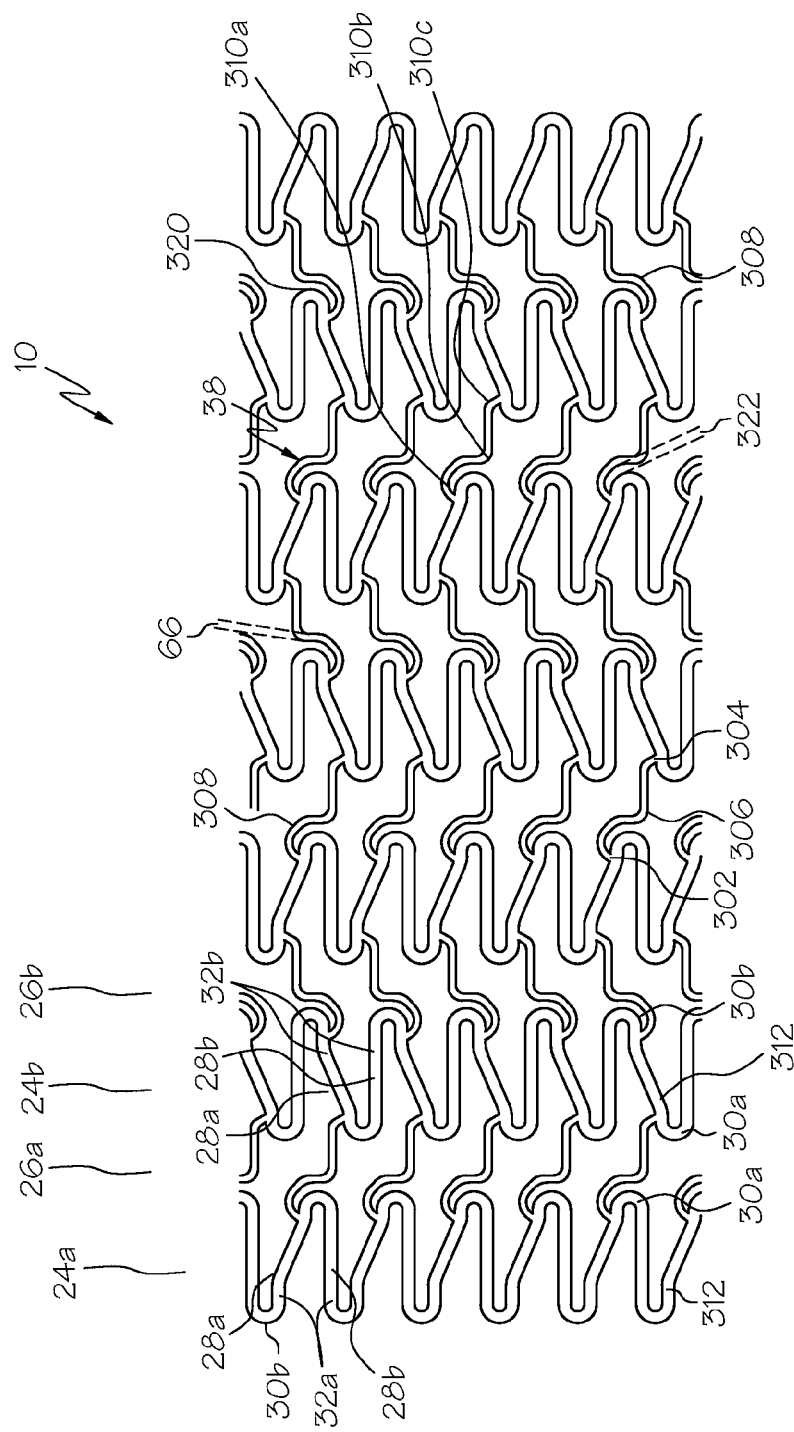
Figure 22:
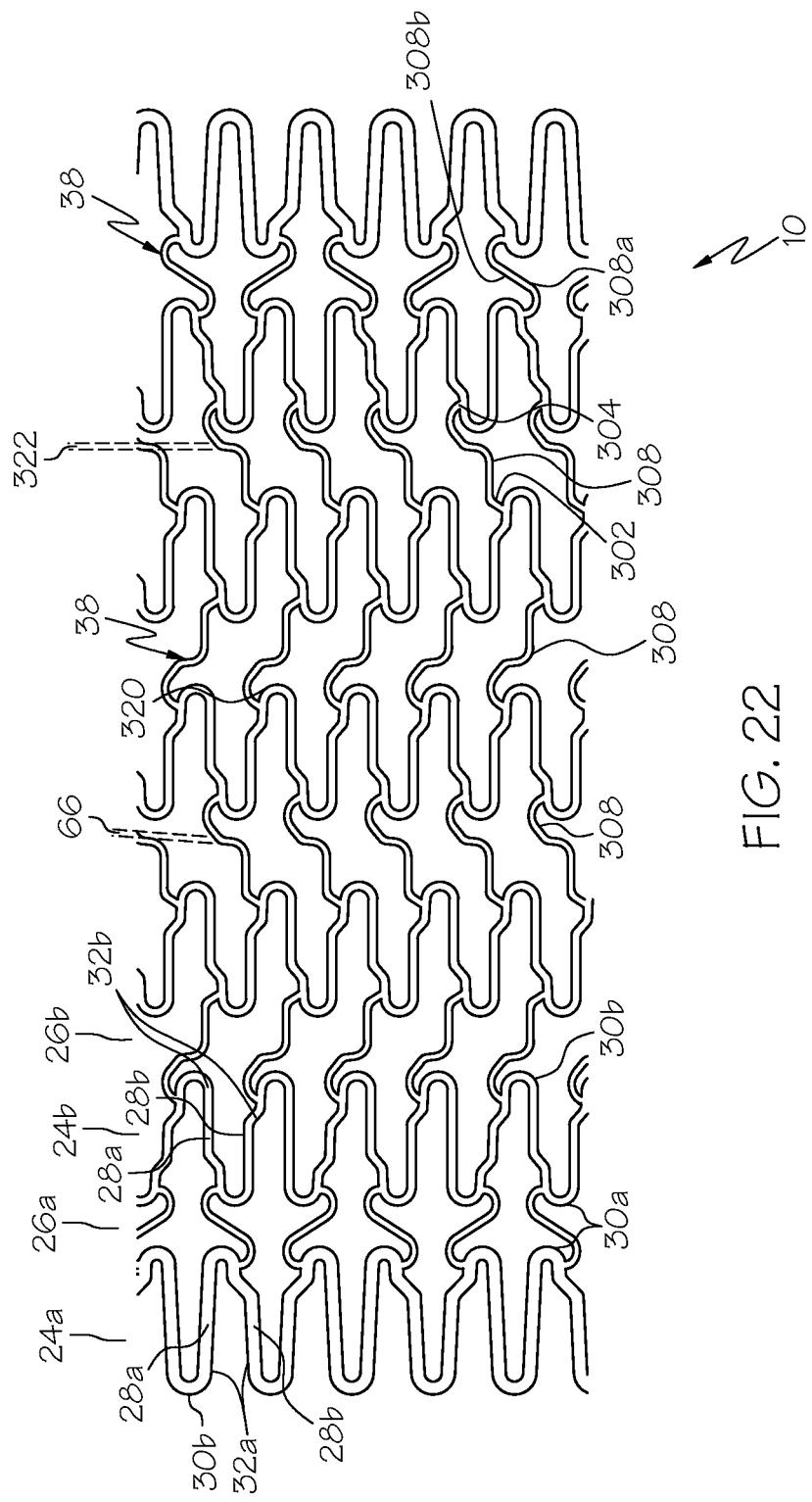
Figure 23:
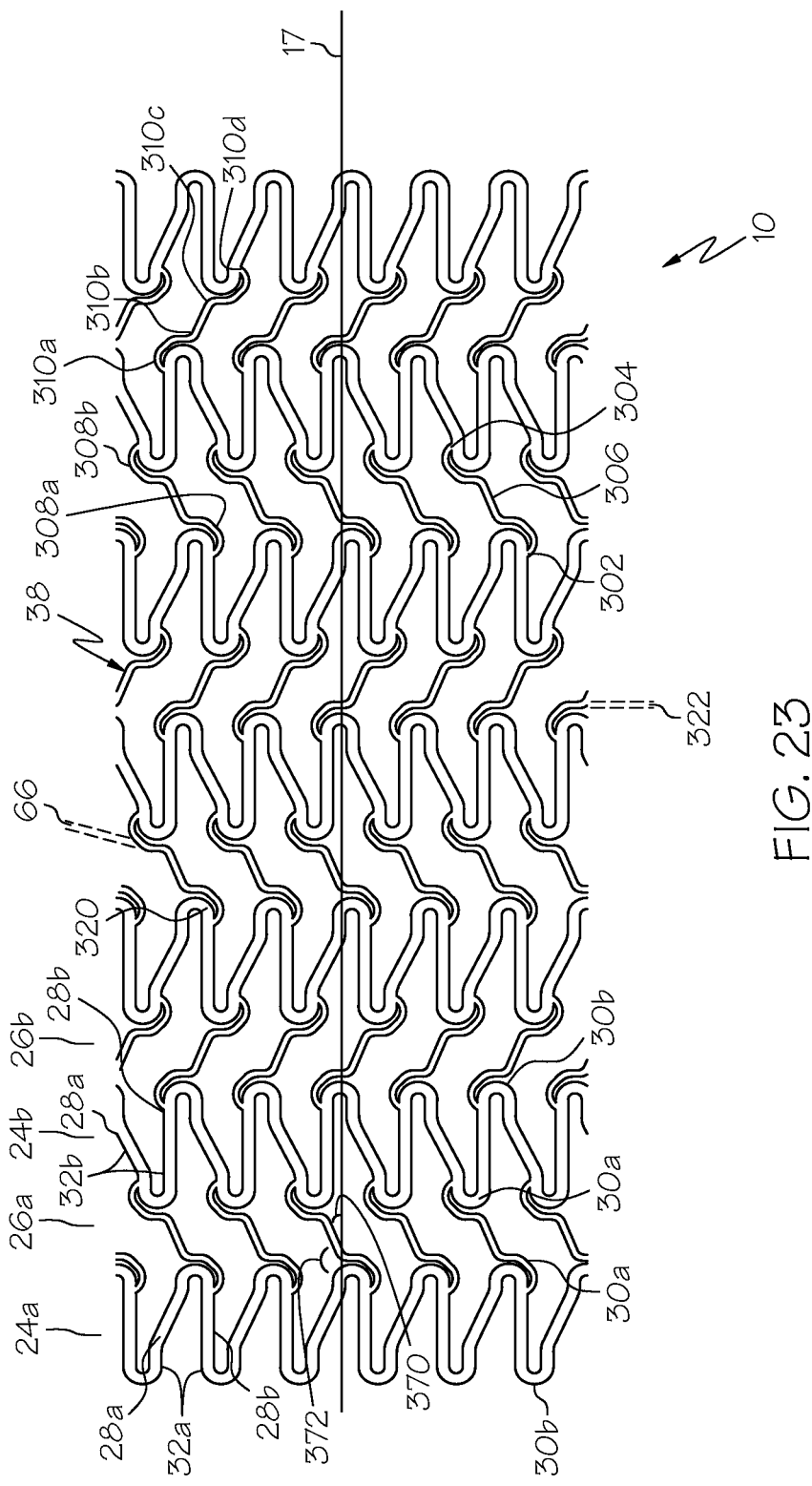
Figure 24:
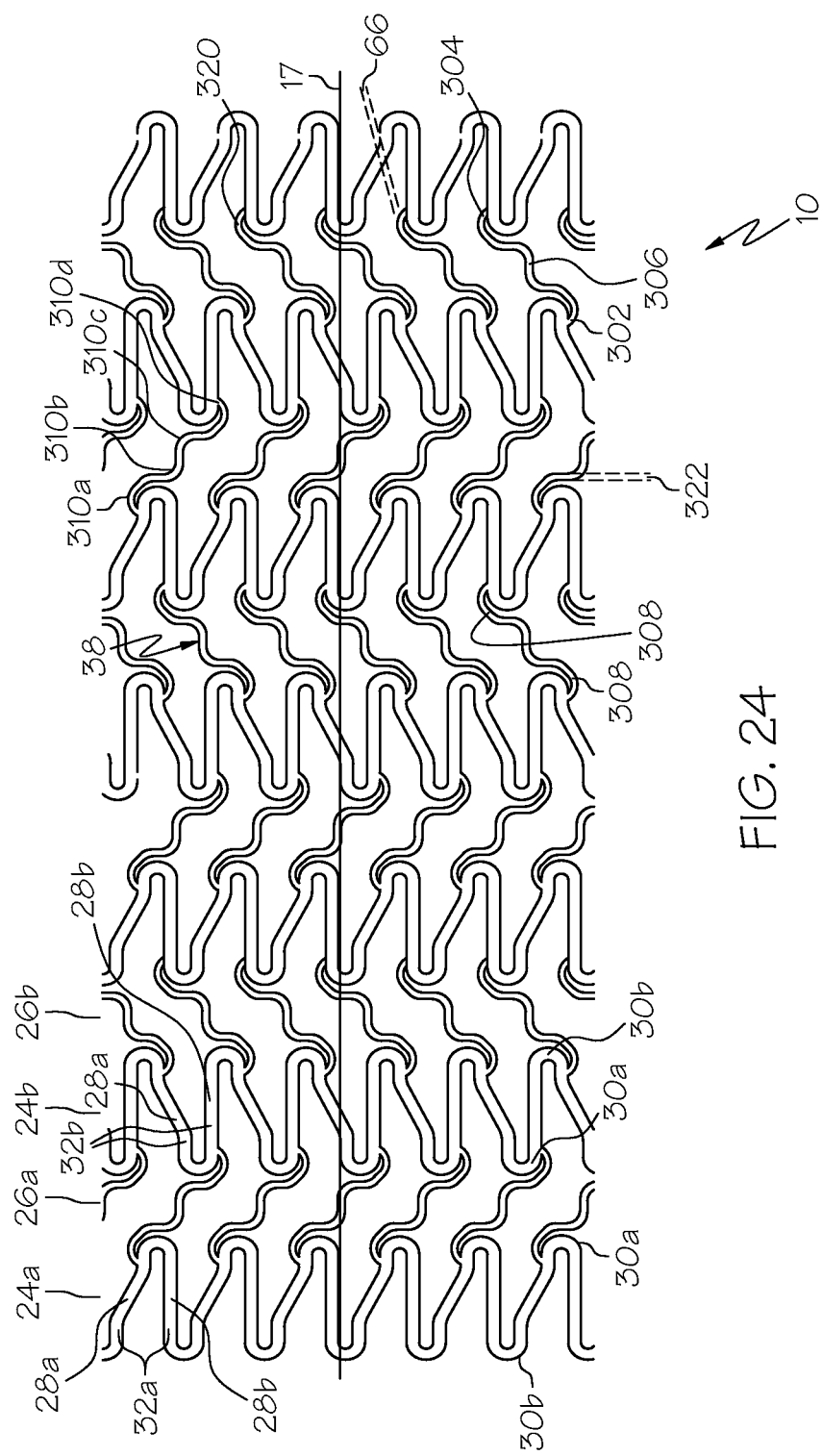
Figure 25:
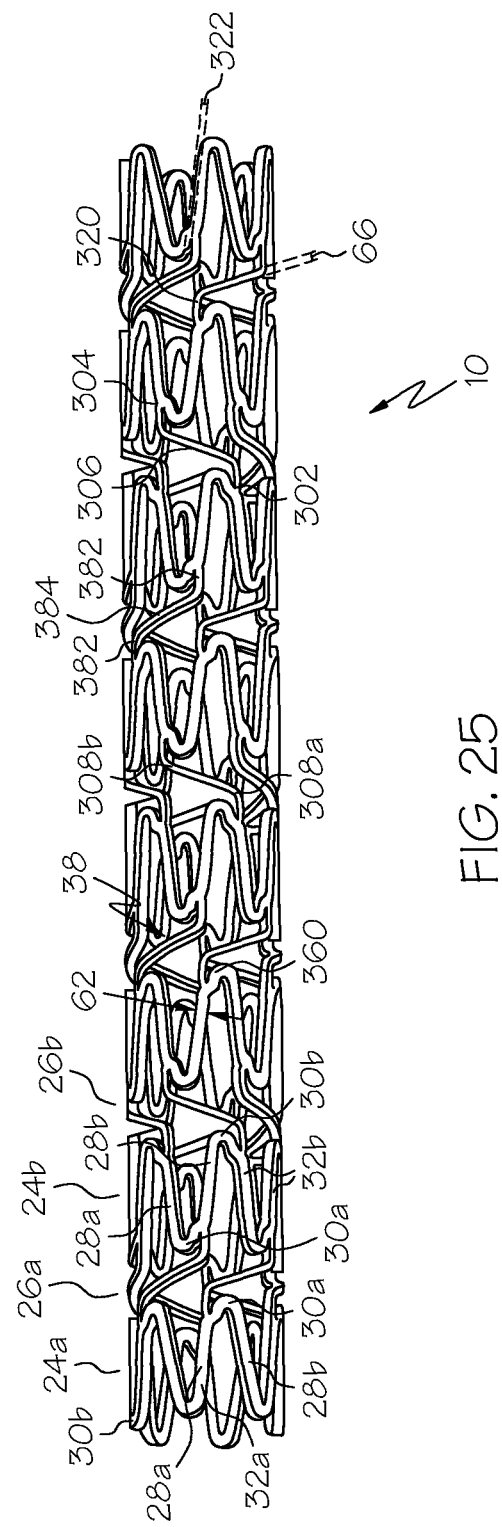
Figure 26:
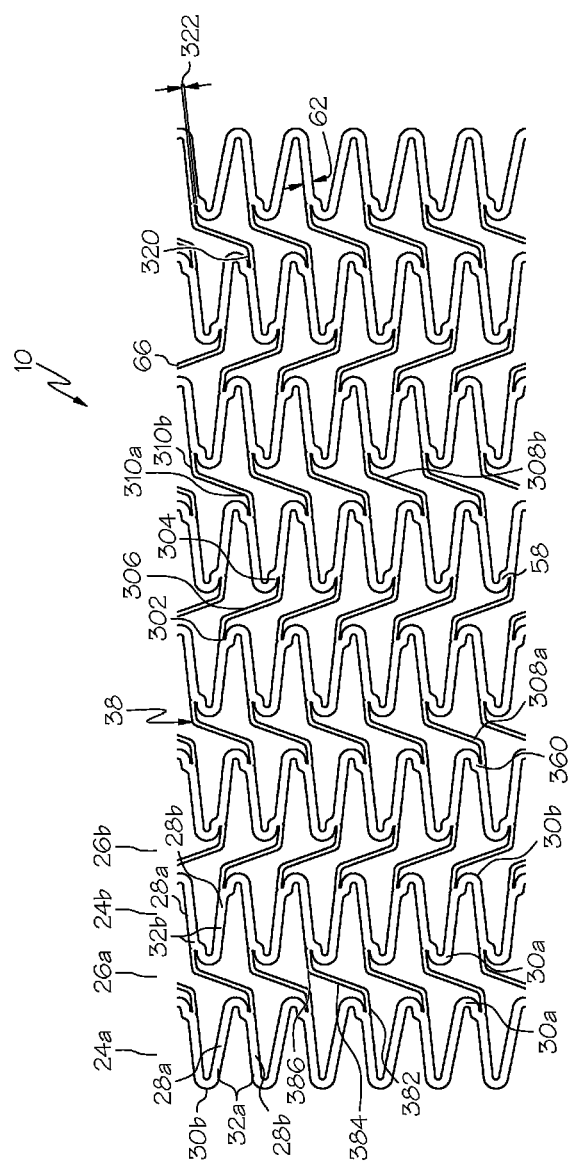
Figure 27:
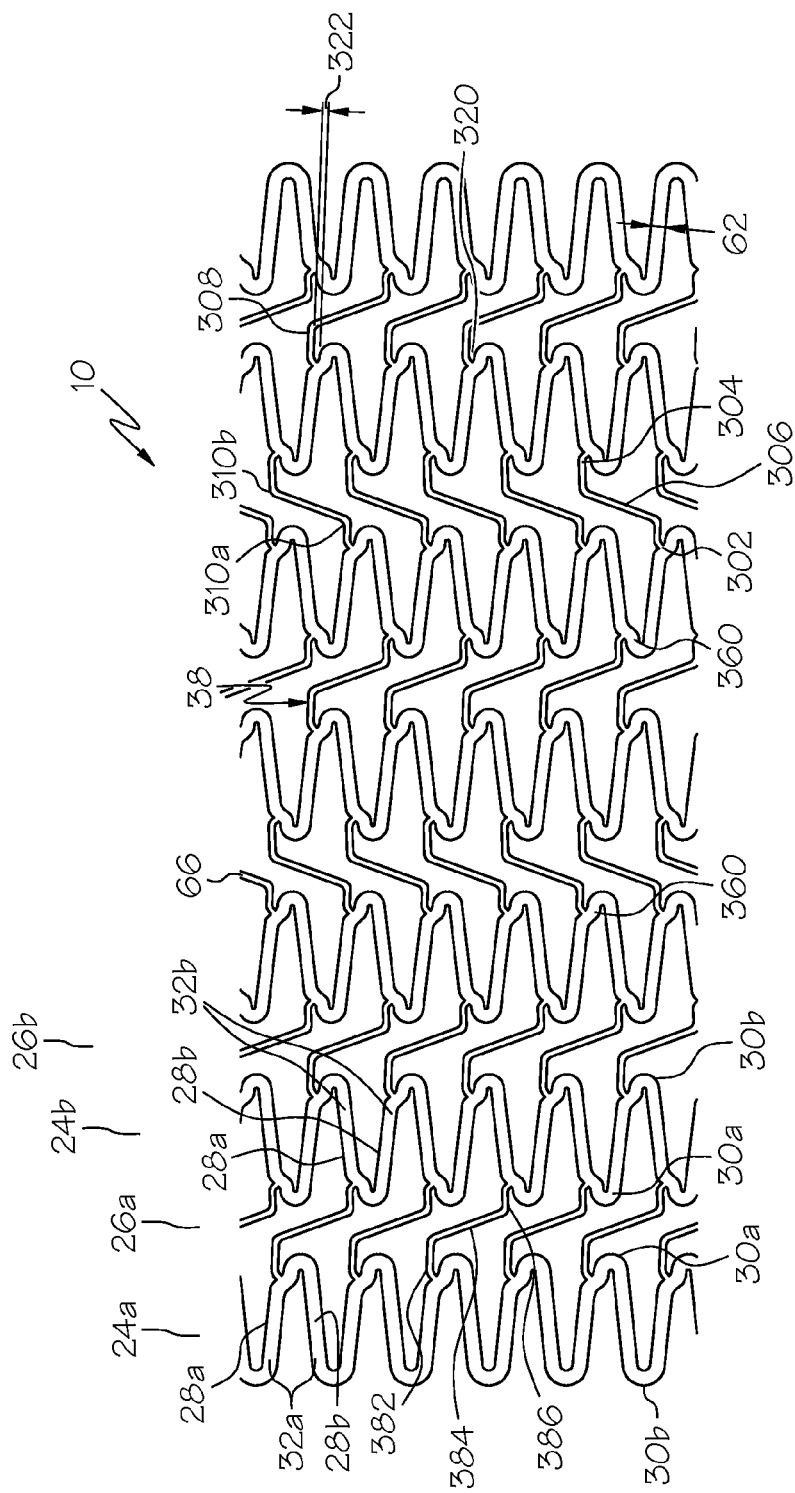
Figure 28:
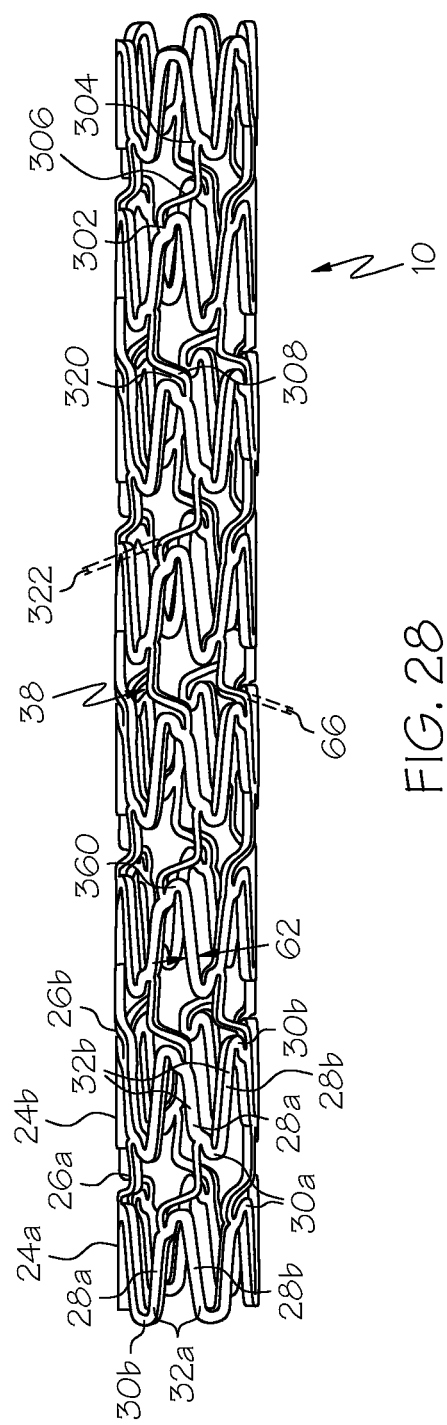
Figure 29:
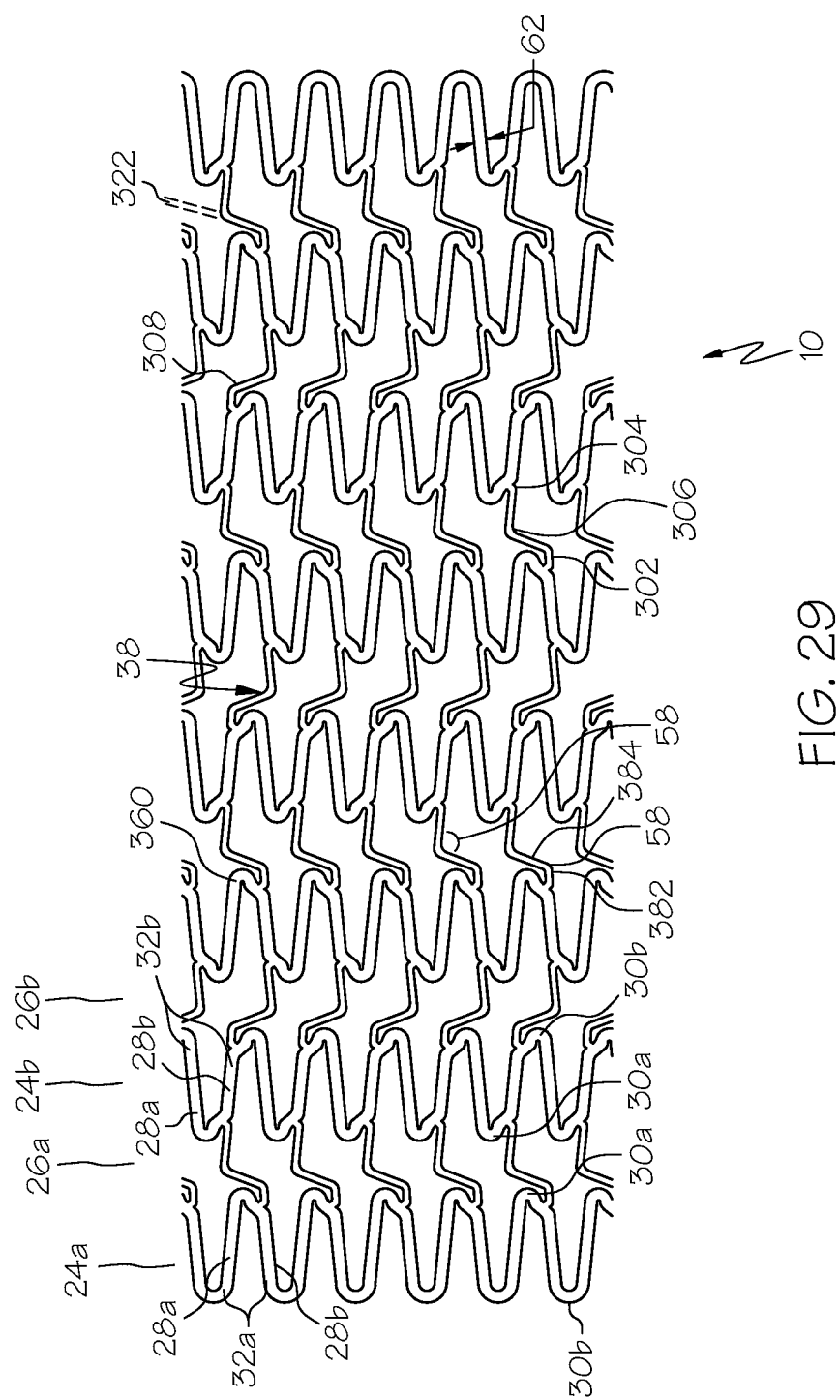
Figure 30:
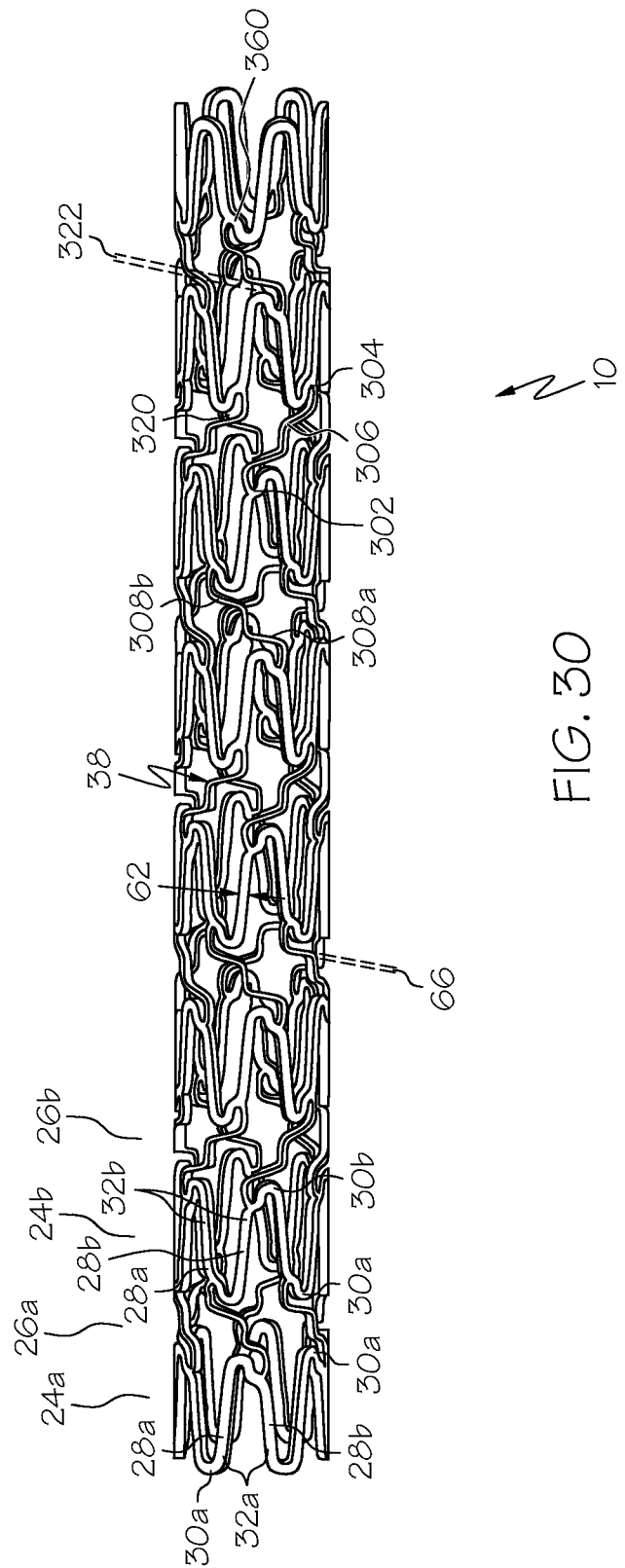
Figure 31:
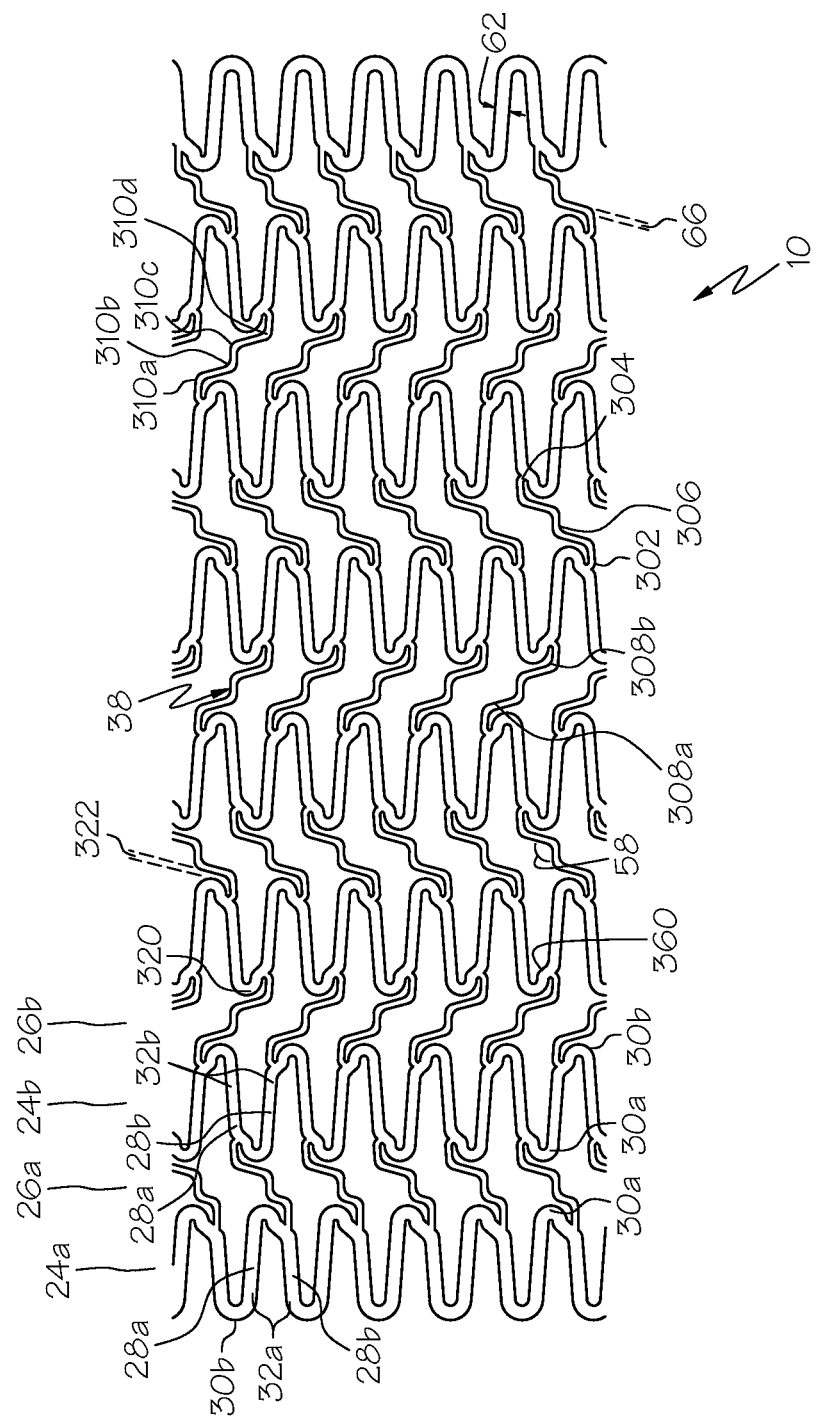
Figure 32:
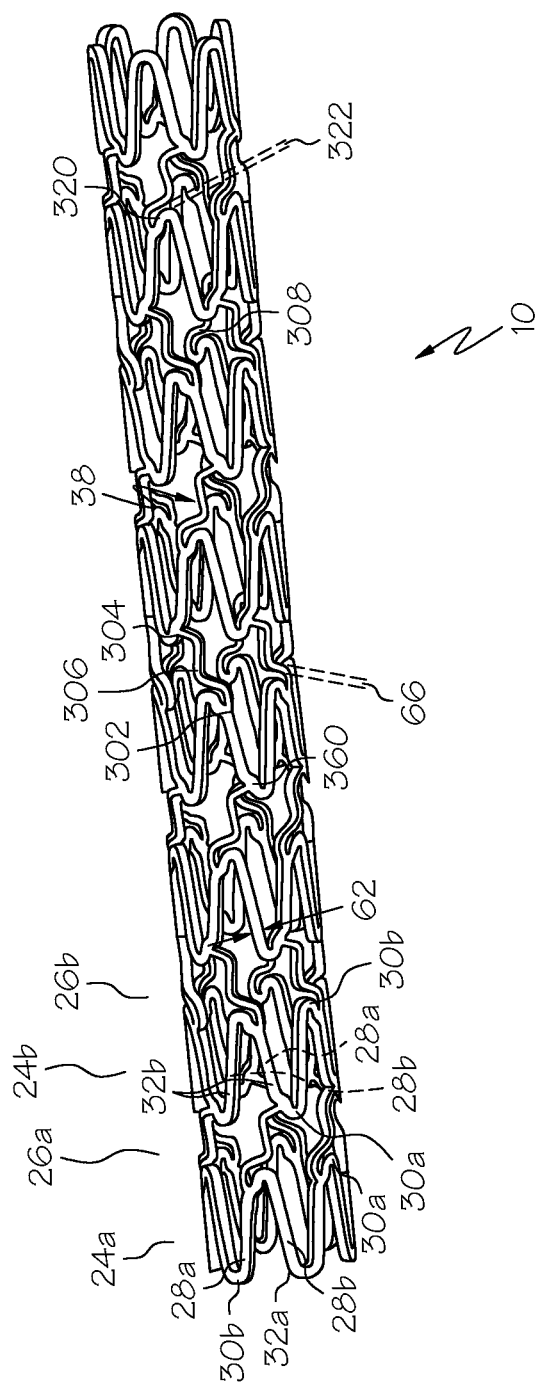
Figure 33:
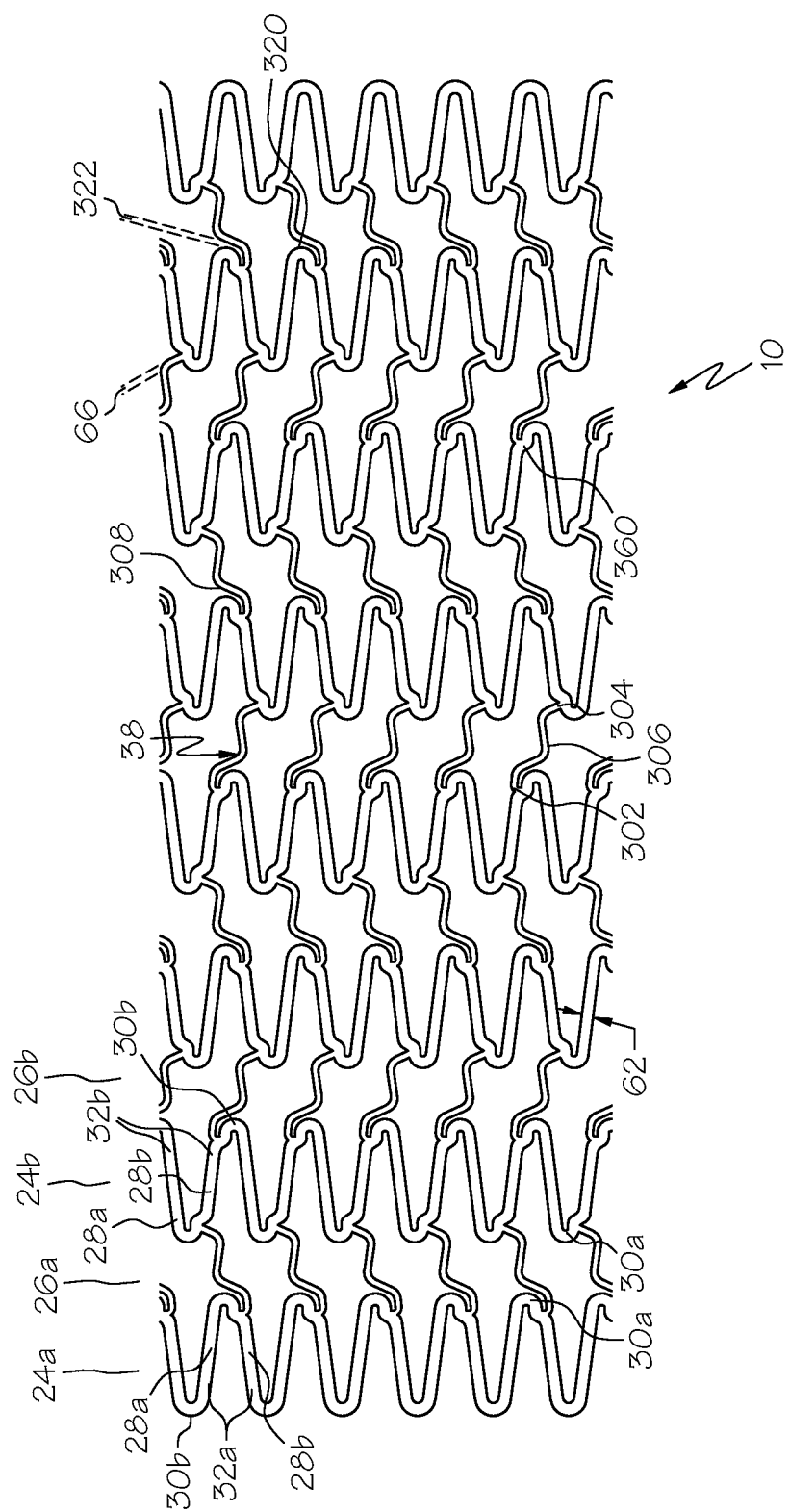
Figure 34:
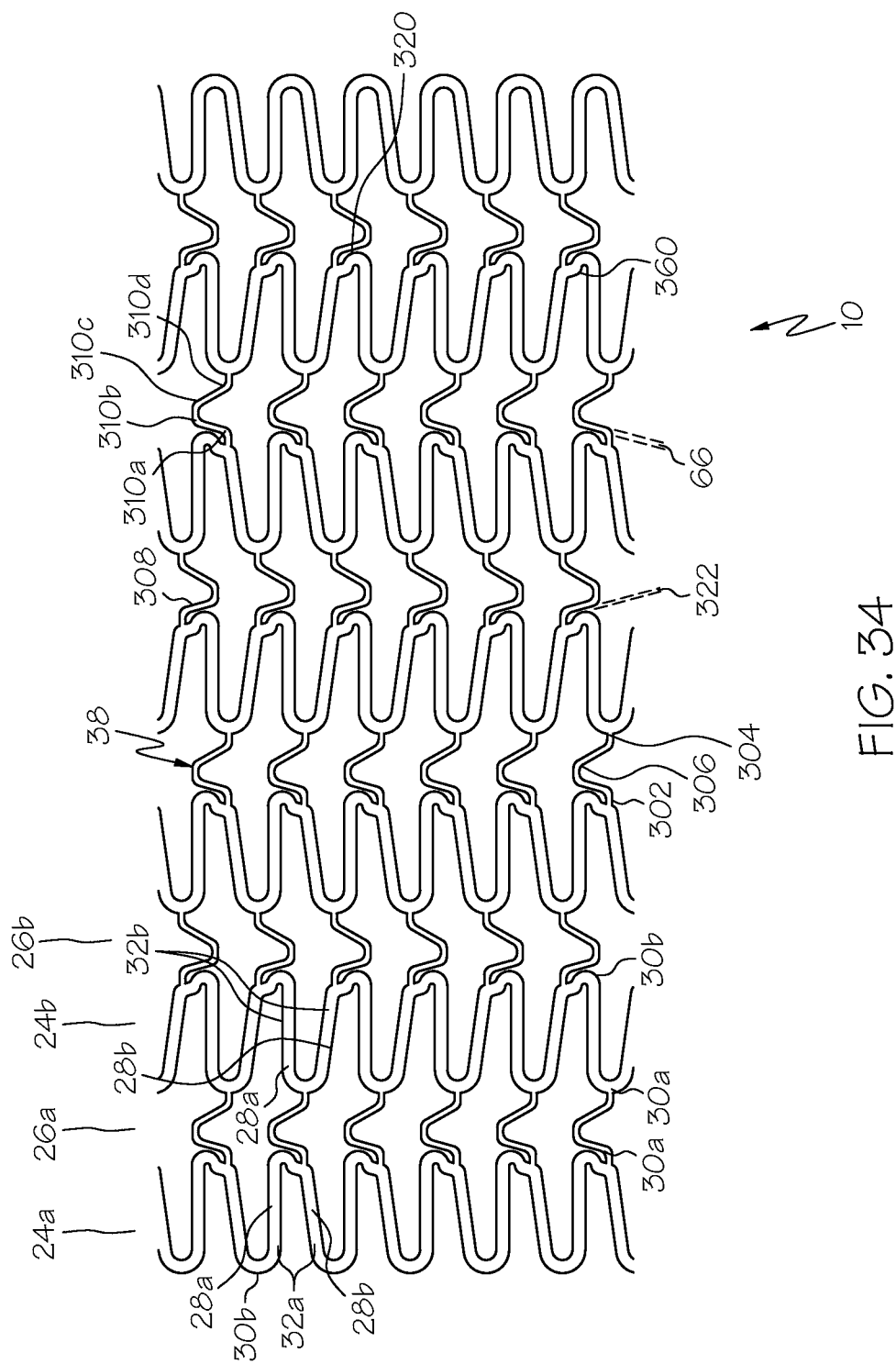
Figure 35A:
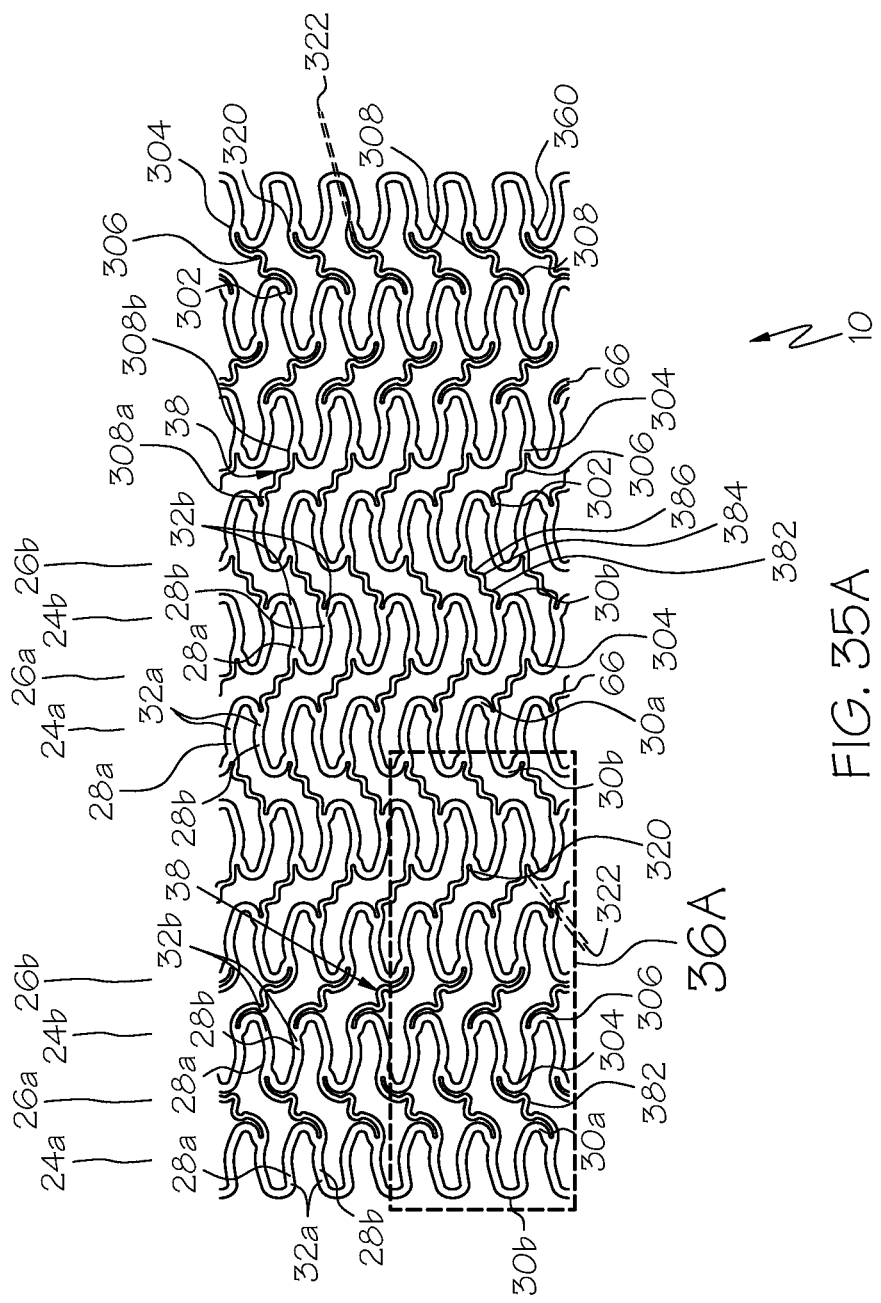
Figure 35B:
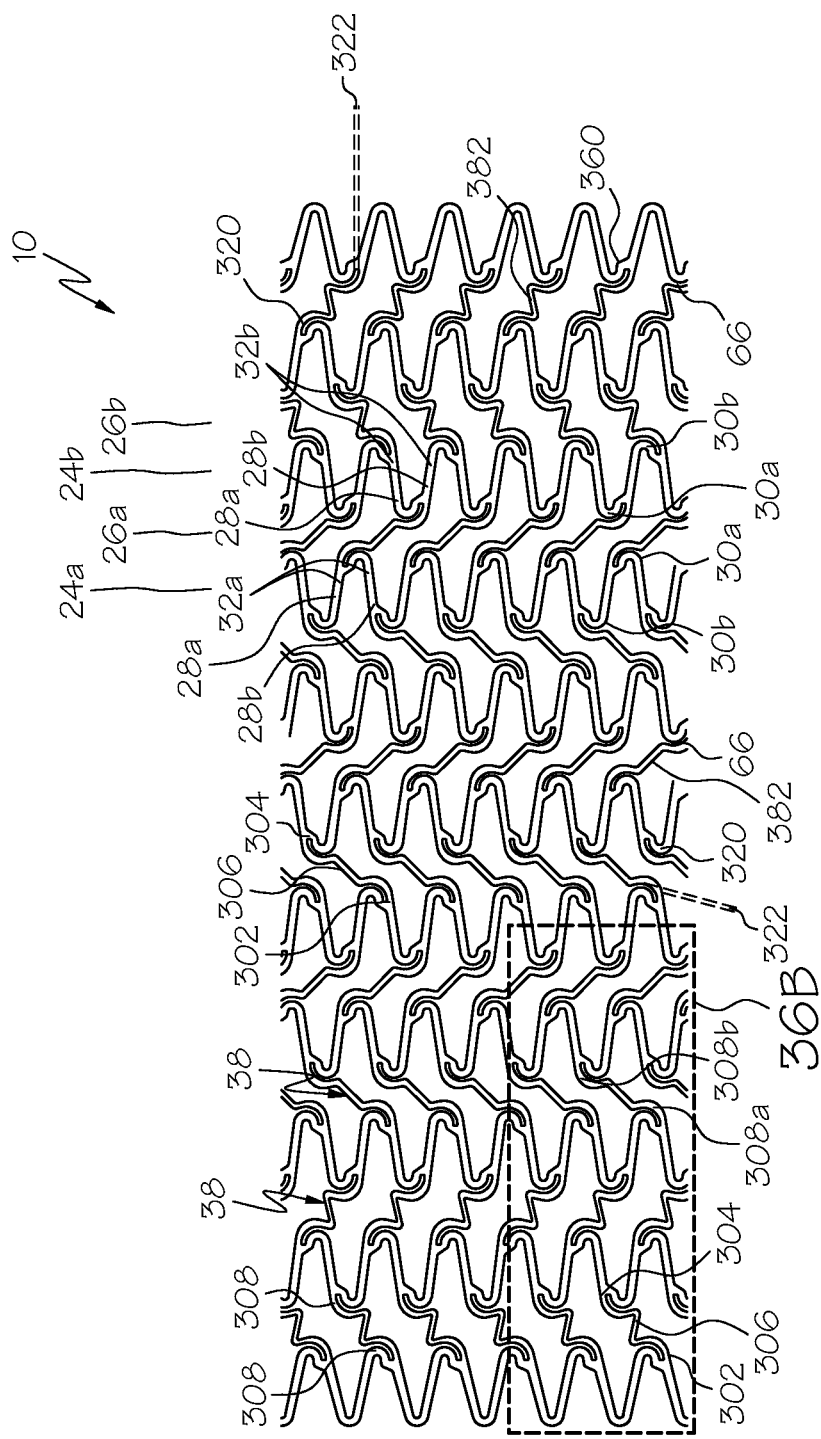
Figure 36A:
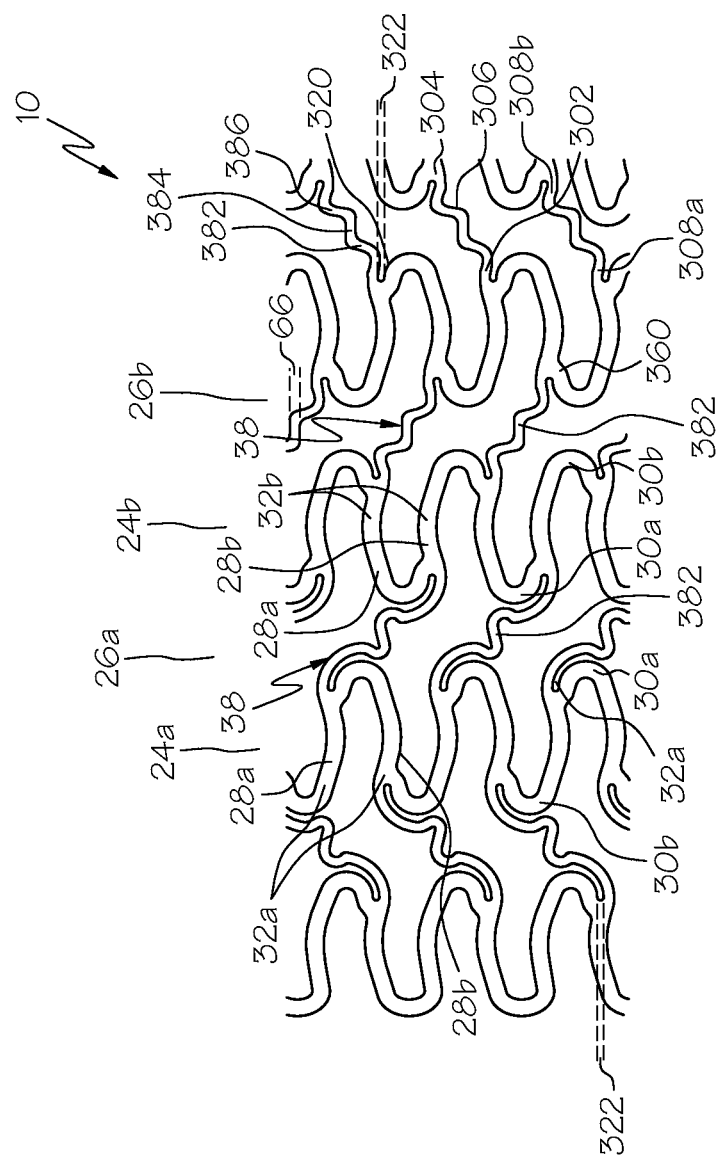
Figure 37:
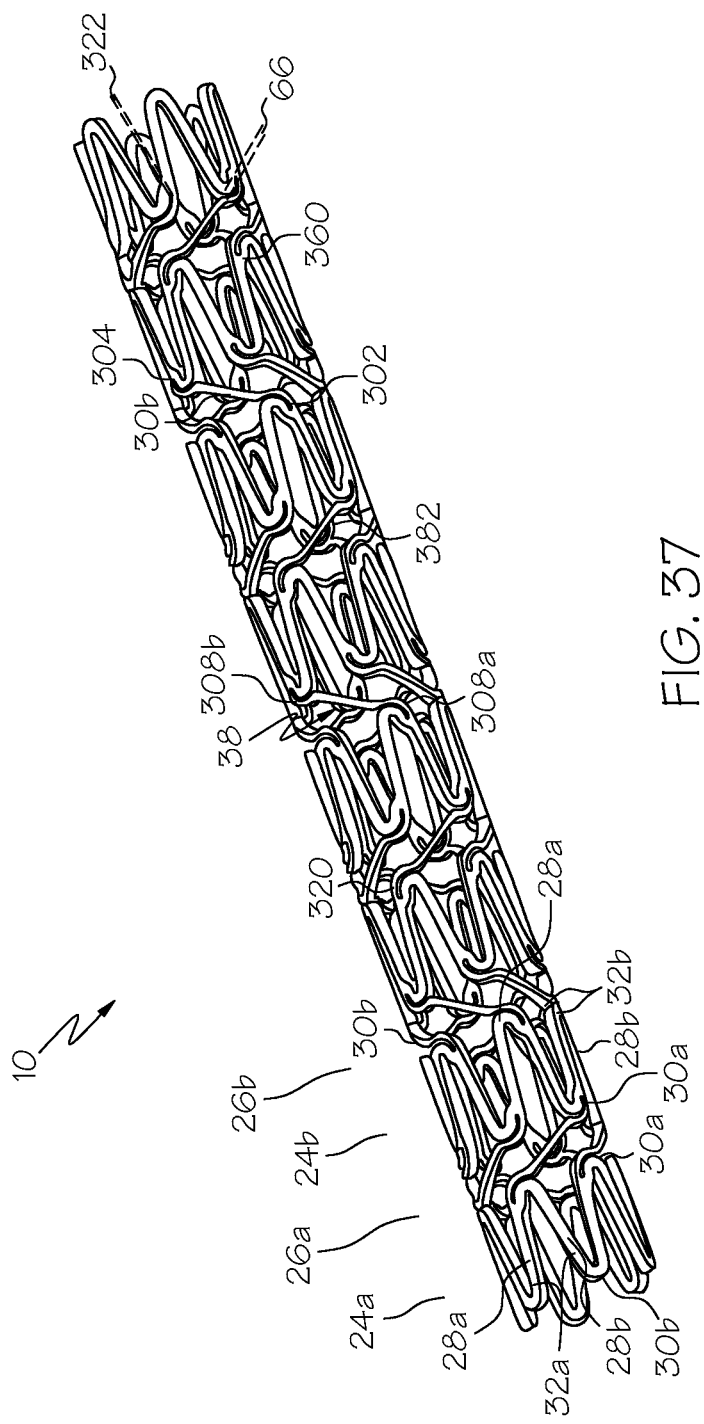
Figure 38:
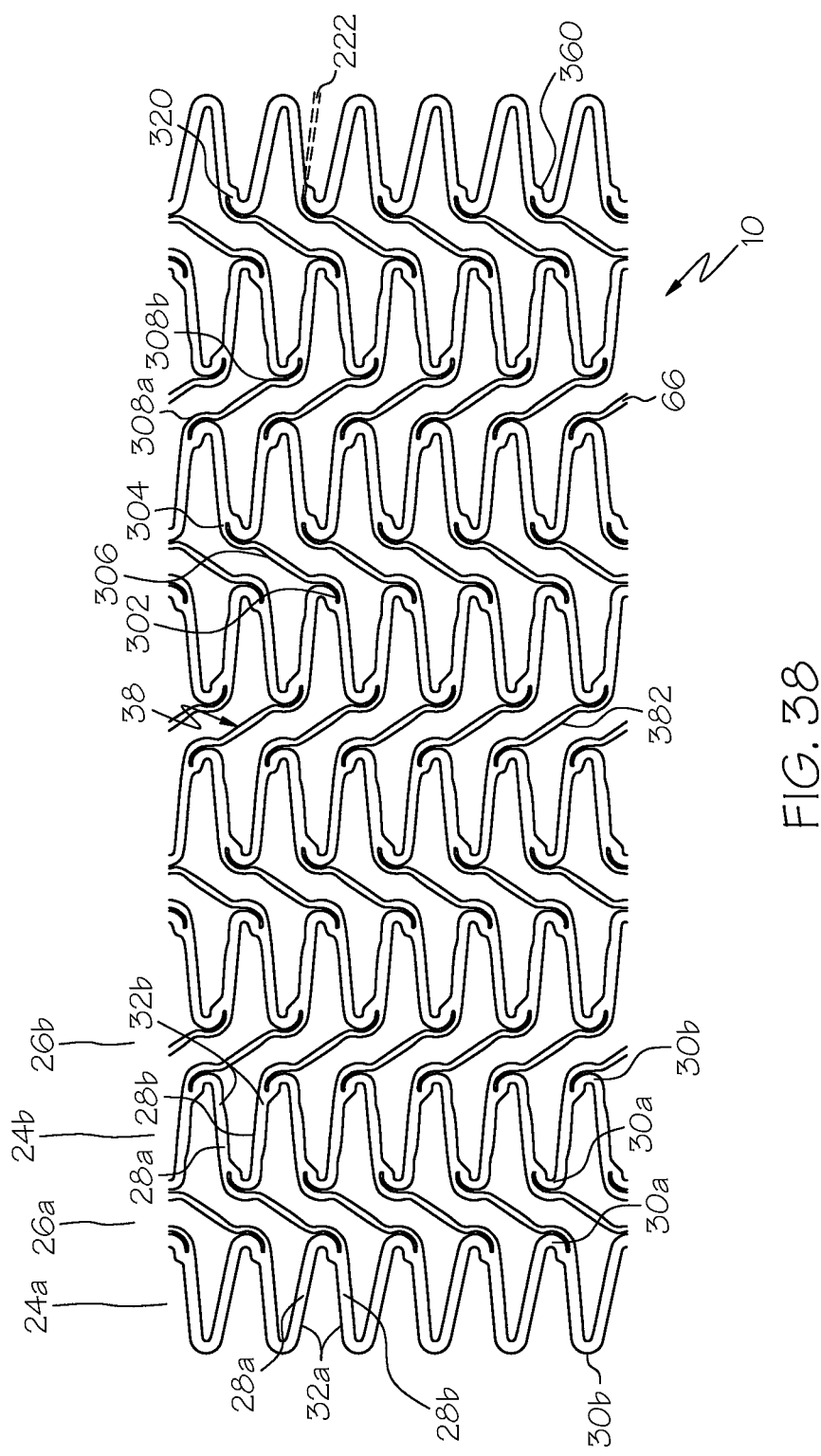
Figure 39:
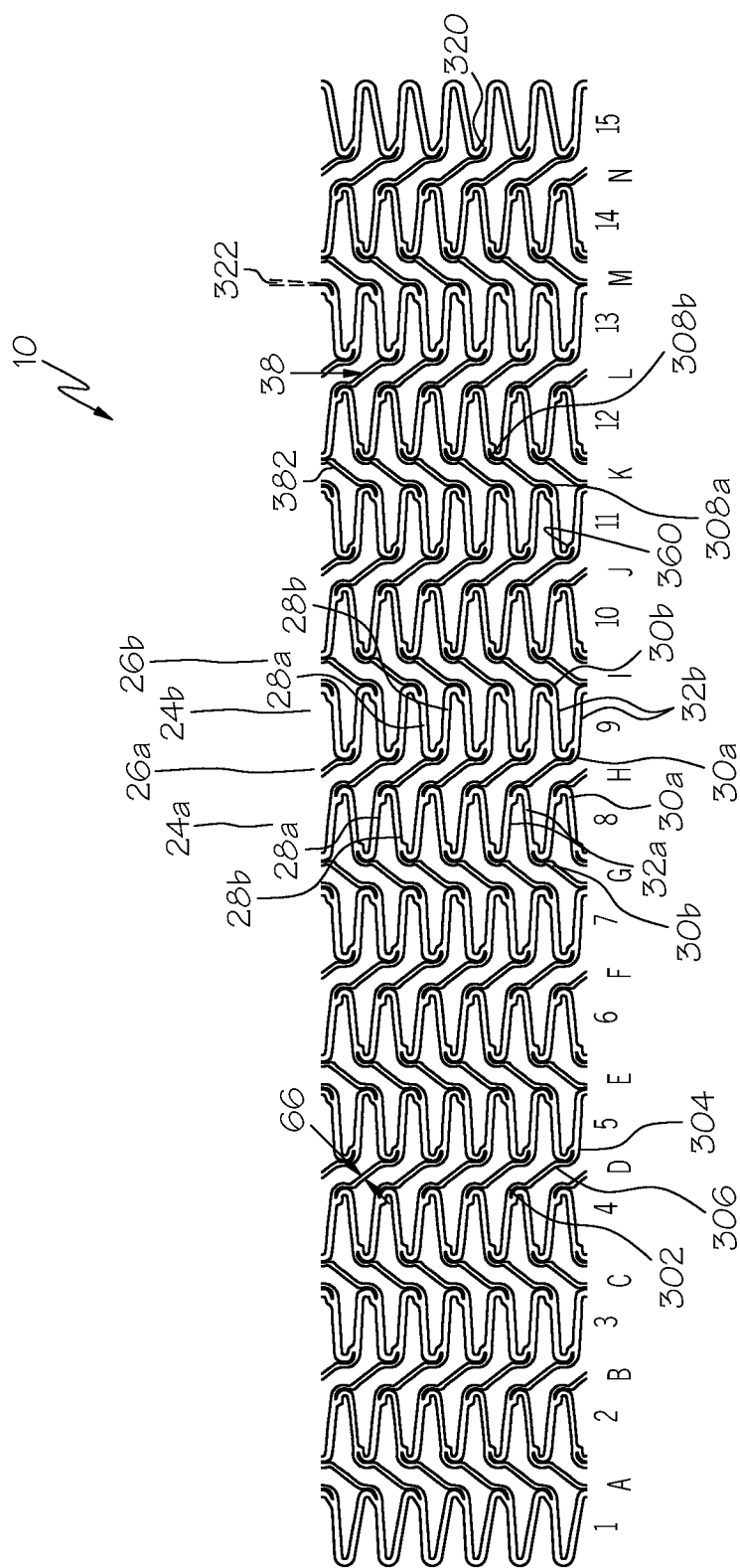
Figure 40:
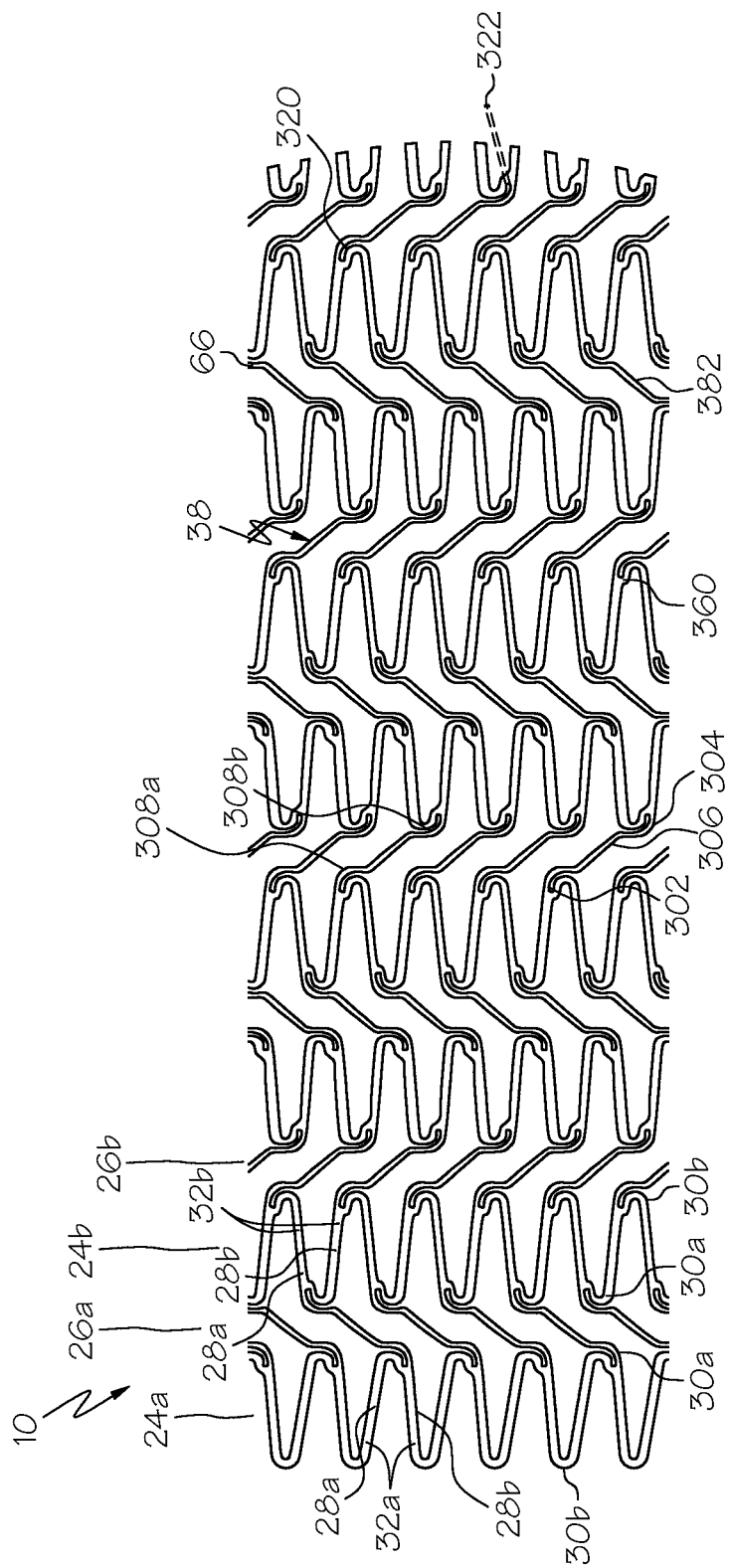
Figure 41:
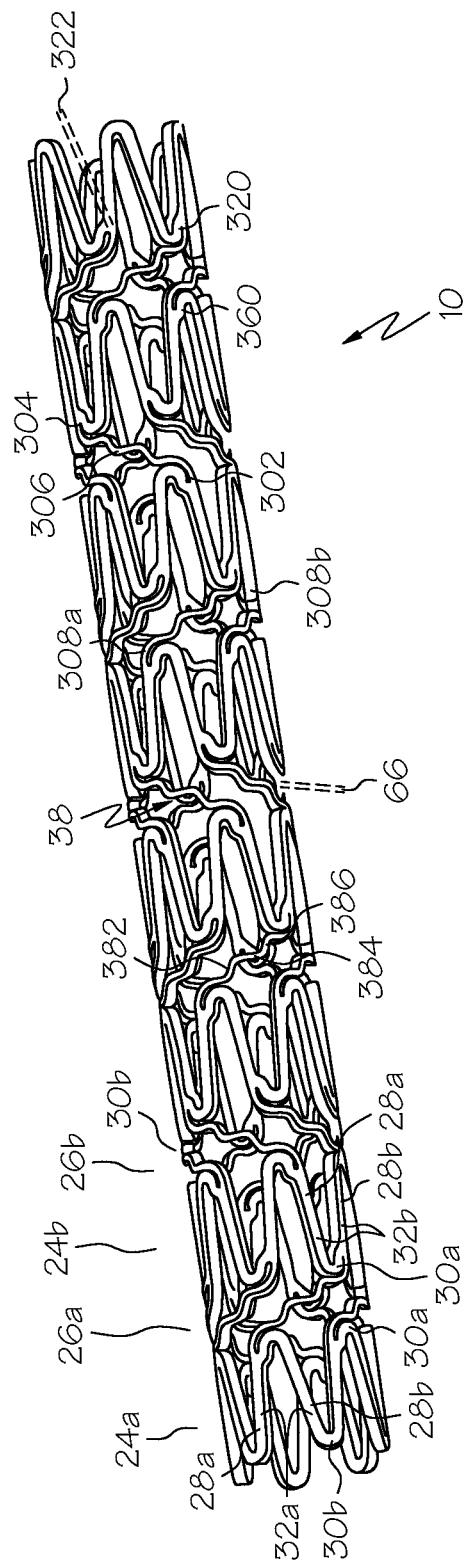
Figure 42:
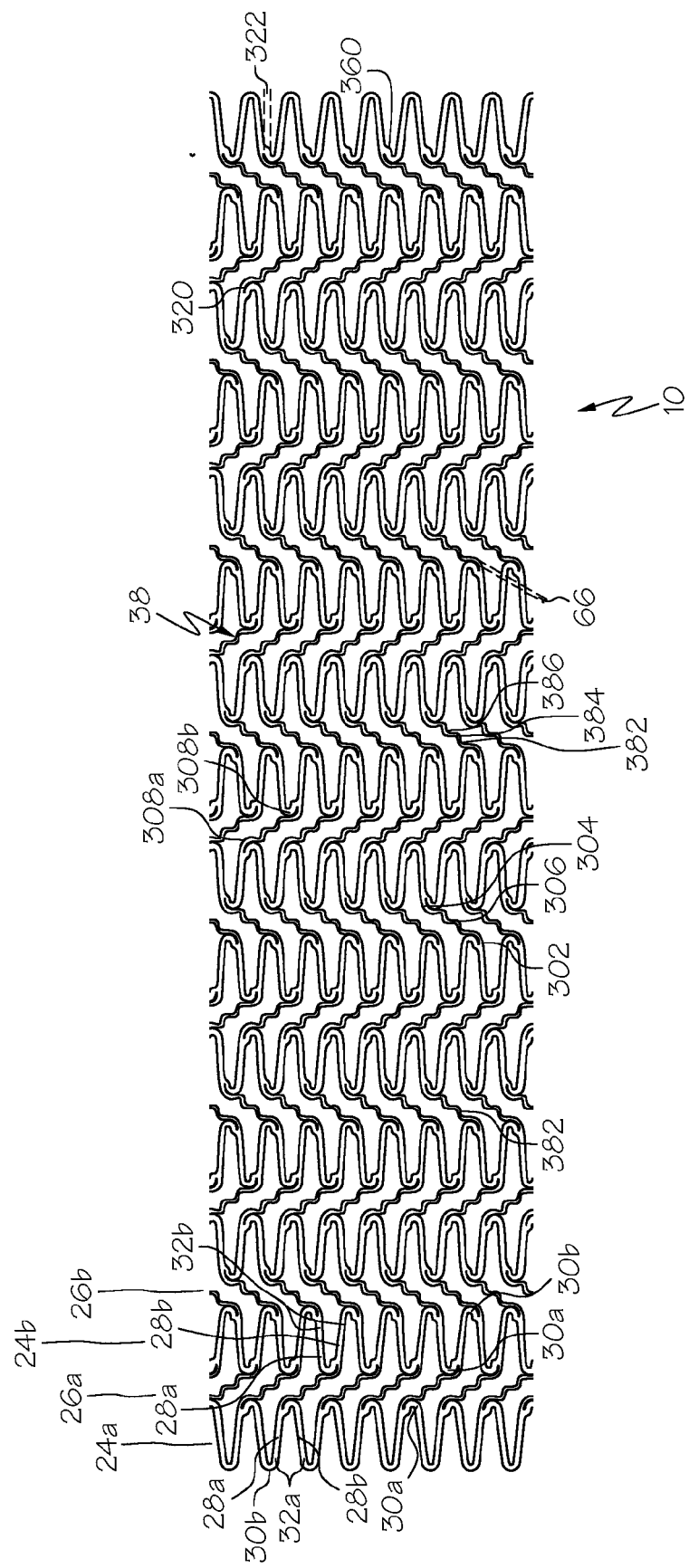
Figure 43:
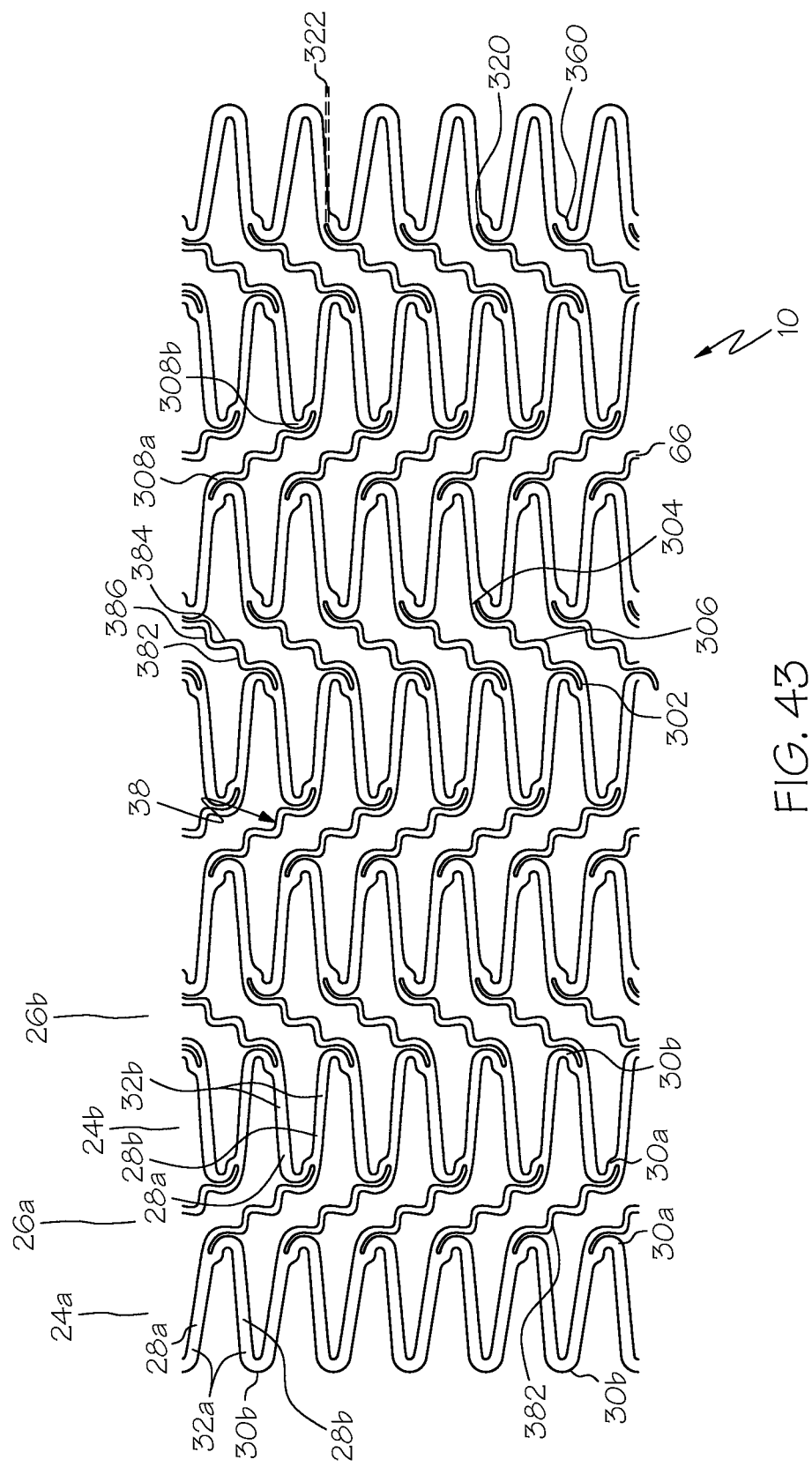
Figure 44:
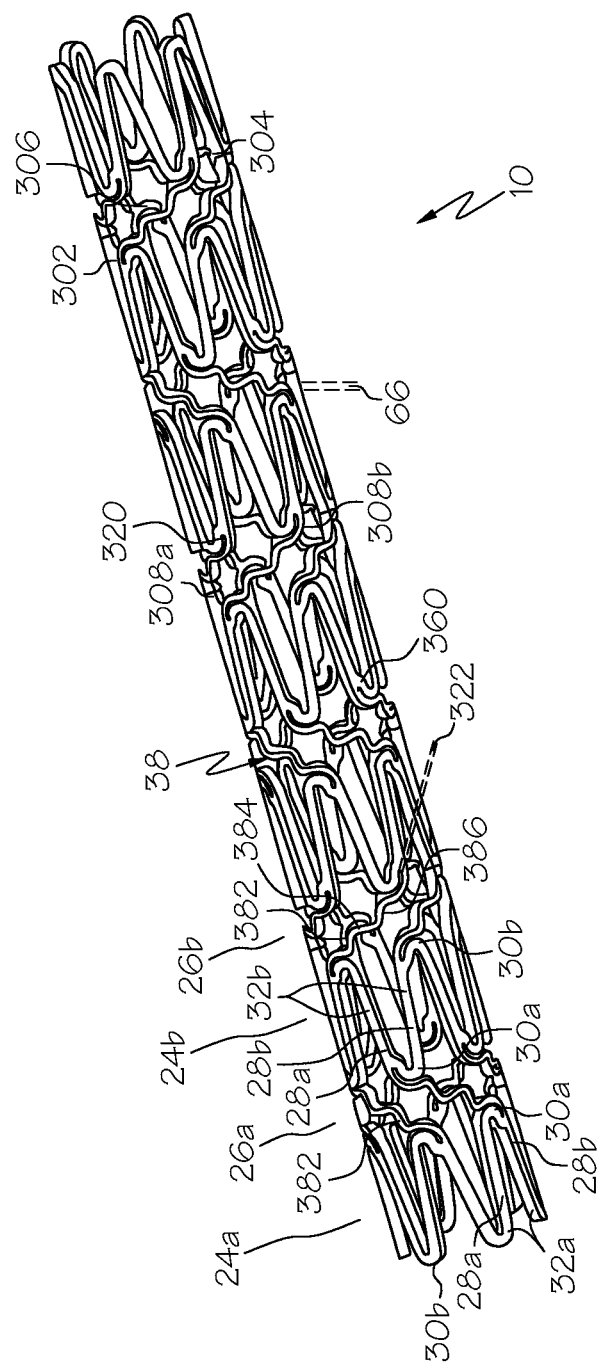
Figure 45:
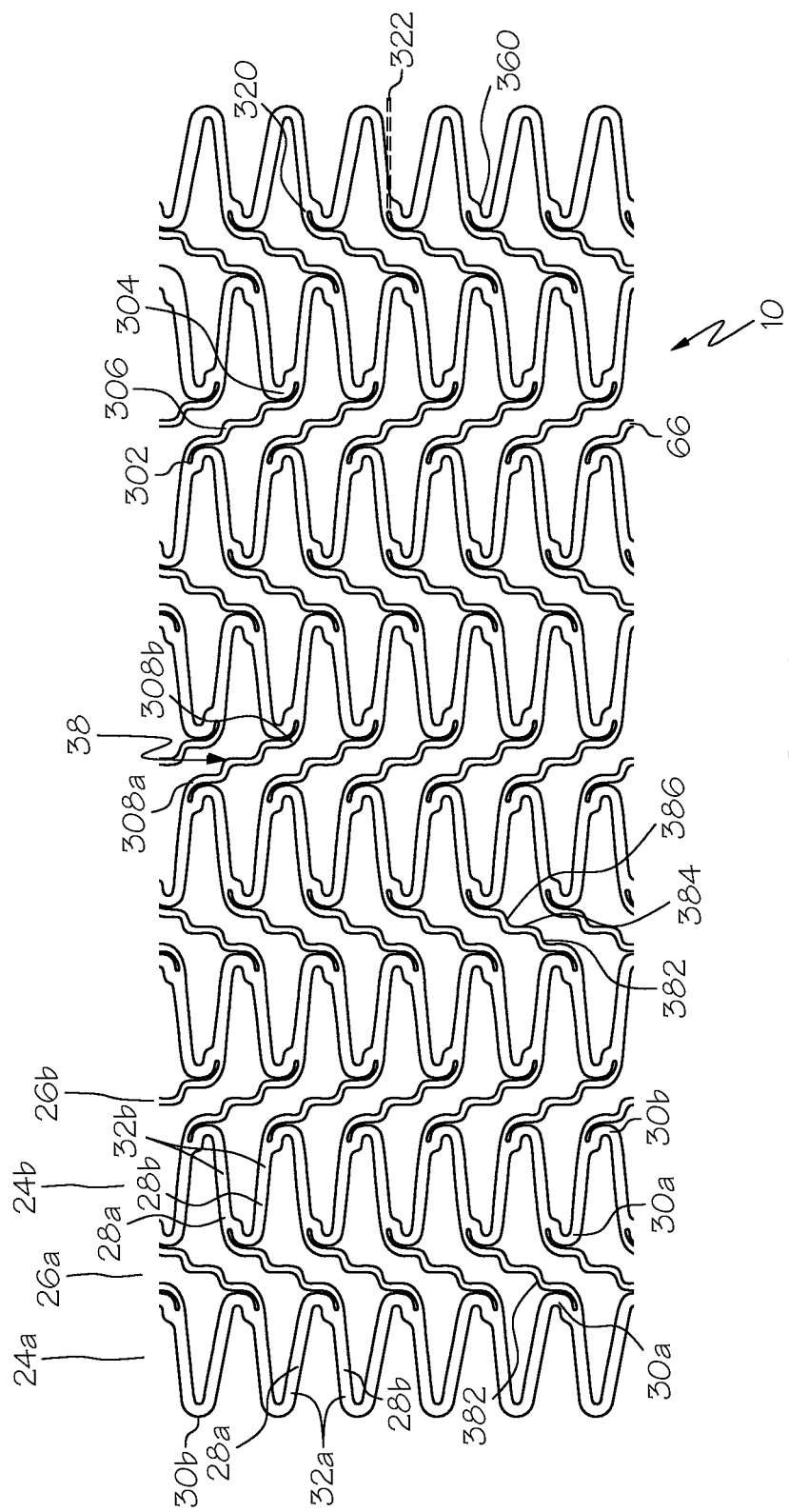

FIG. 19 is a side view of an embodiment of the invention.
FIG. 20 is a side view of an embodiment of the invention.
FIG. 21 is a side view of an embodiment of the invention.
FIG. 22 is a side view of an embodiment of the invention.
FIG. 23 is a side view of an embodiment of the invention.
FIG. 24 is a side view of an embodiment of the invention.
FIG. 25 is a perspective view of an embodiment of the invention.
FIG. 26 is a side view of an embodiment of the invention.
FIG. 27 is a side view of an embodiment of the invention.
FIG. 28 is a perspective view of an embodiment of the invention.
FIG. 29 is a side view of an embodiment of the invention.
FIG. 30 is a perspective view of an embodiment of the invention.
FIG. 31 is a side view of the embodiment of the invention shown in FIG. 30.
FIG. 32 is a perspective view of an embodiment of the invention.
FIG. 33 is a side view of an embodiment of the invention.
FIG. 34 is a side view of an embodiment of the invention.
FIG. 35A is a side view of an embodiment of the invention.
FIG. 35B is a side view of an embodiment of the invention.
FIG. 36A is an enlarged view of a portion of the embodiment shown in FIG. 35A.
FIG. 36B is an enlarged view of a portion of the embodiment shown in FIG. 35B
FIG. 37 is a perspective view of an embodiment of the invention.
FIG. 38 is a side view of an embodiment of the invention.
FIG. 39 is a side view of a configuration of the embodiment shown in FIG. 38.
FIG. 40 is a partial side view of an alternative configuration of the embodiment shown in FIG. 38.
FIG. 41 is a perspective view of an embodiment of the invention.
FIG. 42 is a side view of the embodiment shown in FIG. 41.
FIG. 43 is an enlarged side view of the embodiment shown in FIG. 41.
FIG. 44 is a perspective view of an embodiment of the invention.
FIG. 45 is a side view of the embodiment shown in FIG. 44.

Figure 46:
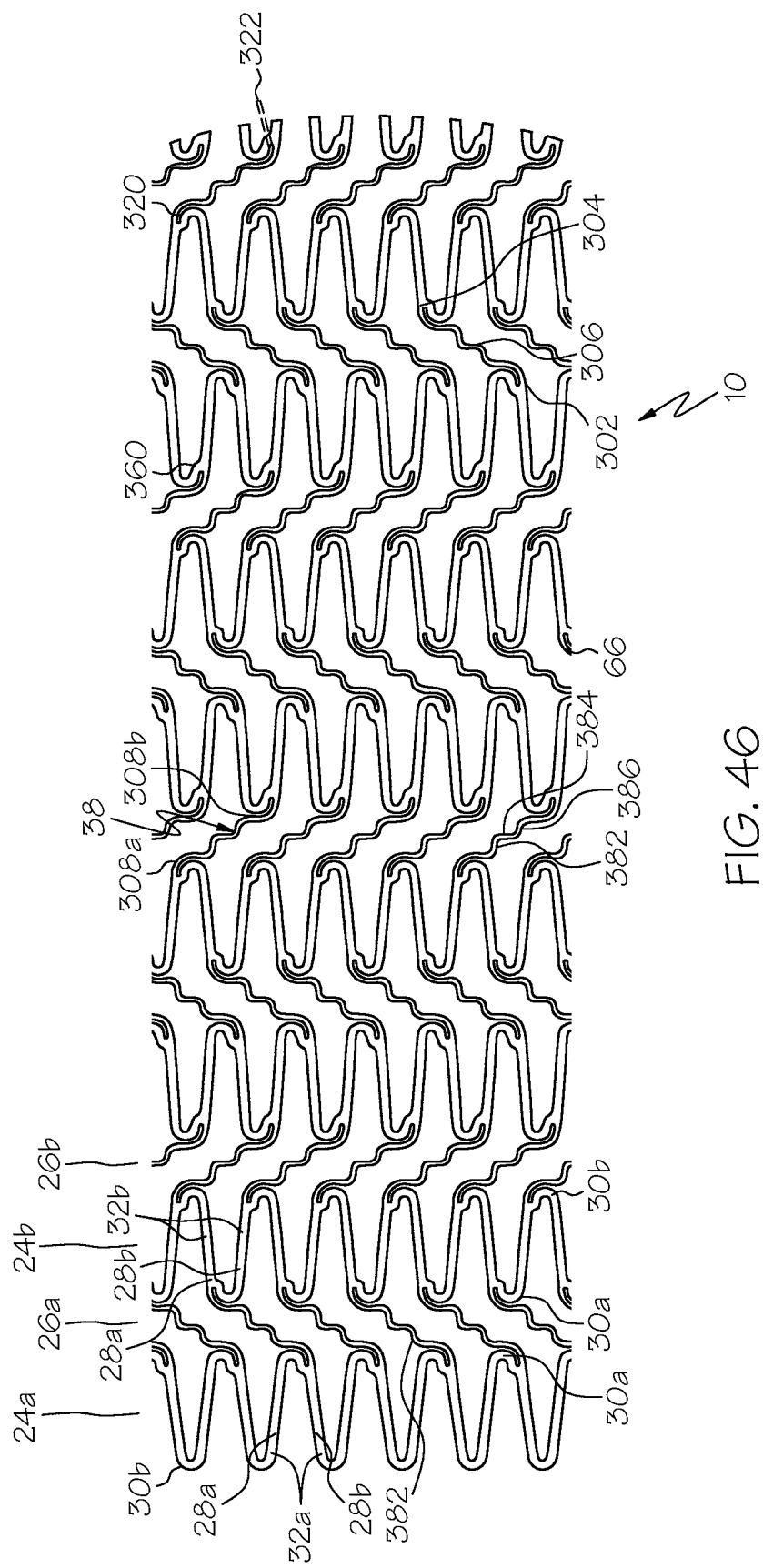
Figure 47:
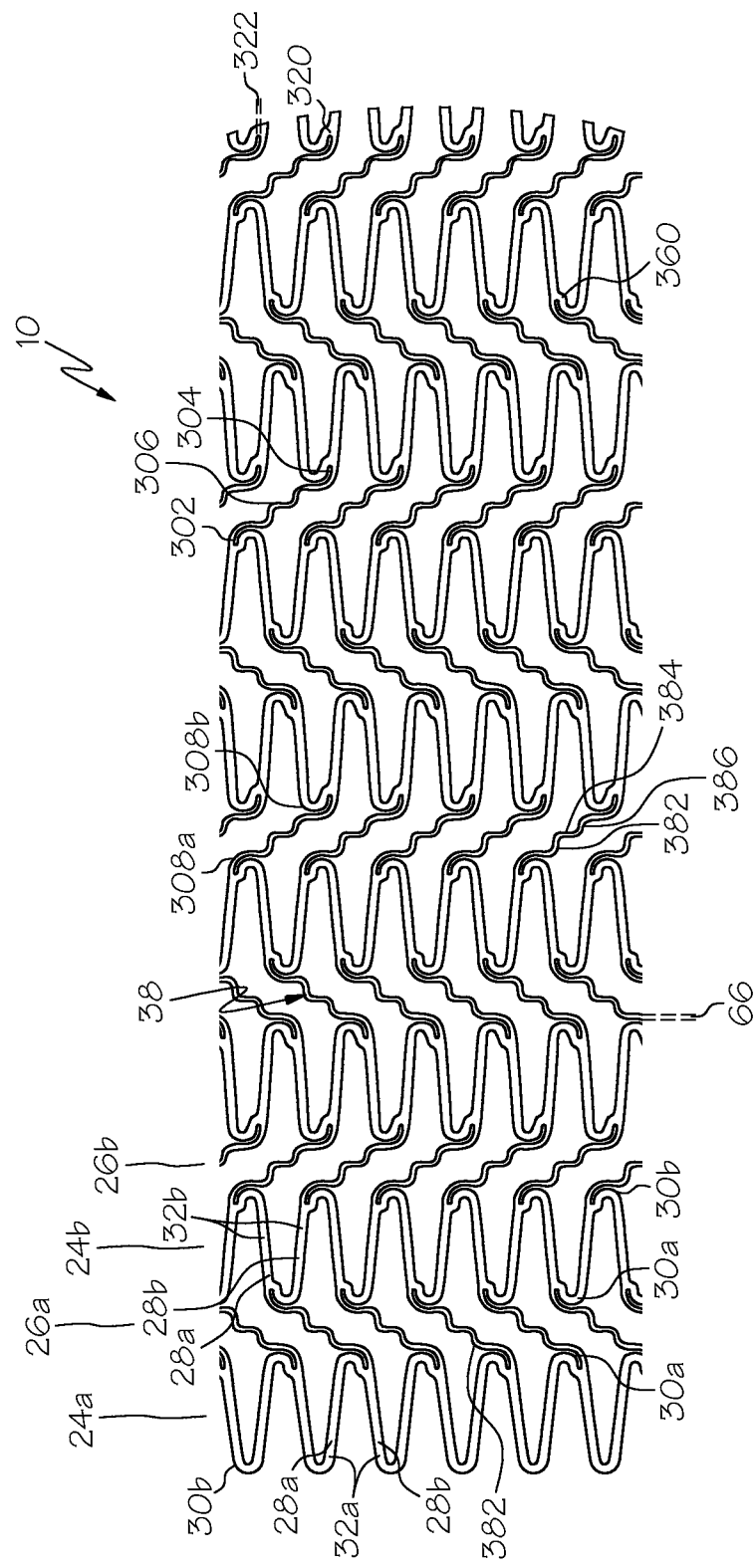
Figure 48:
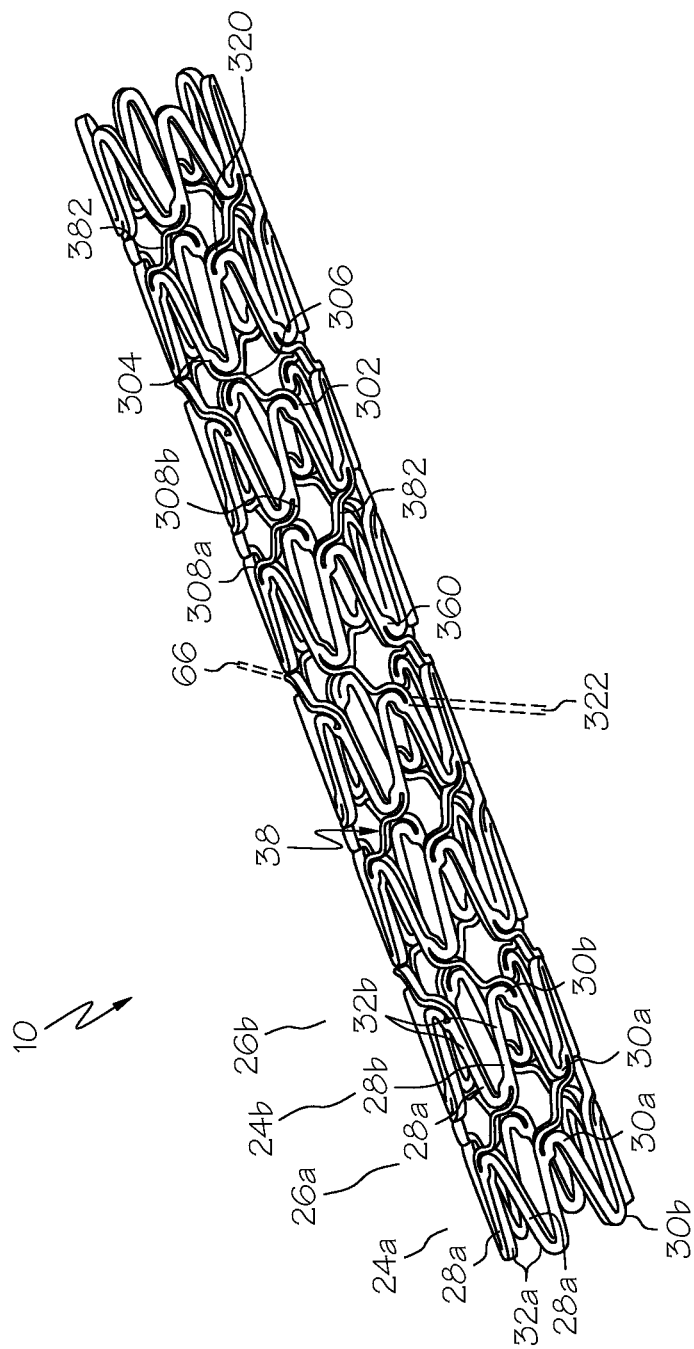
Figure 49:
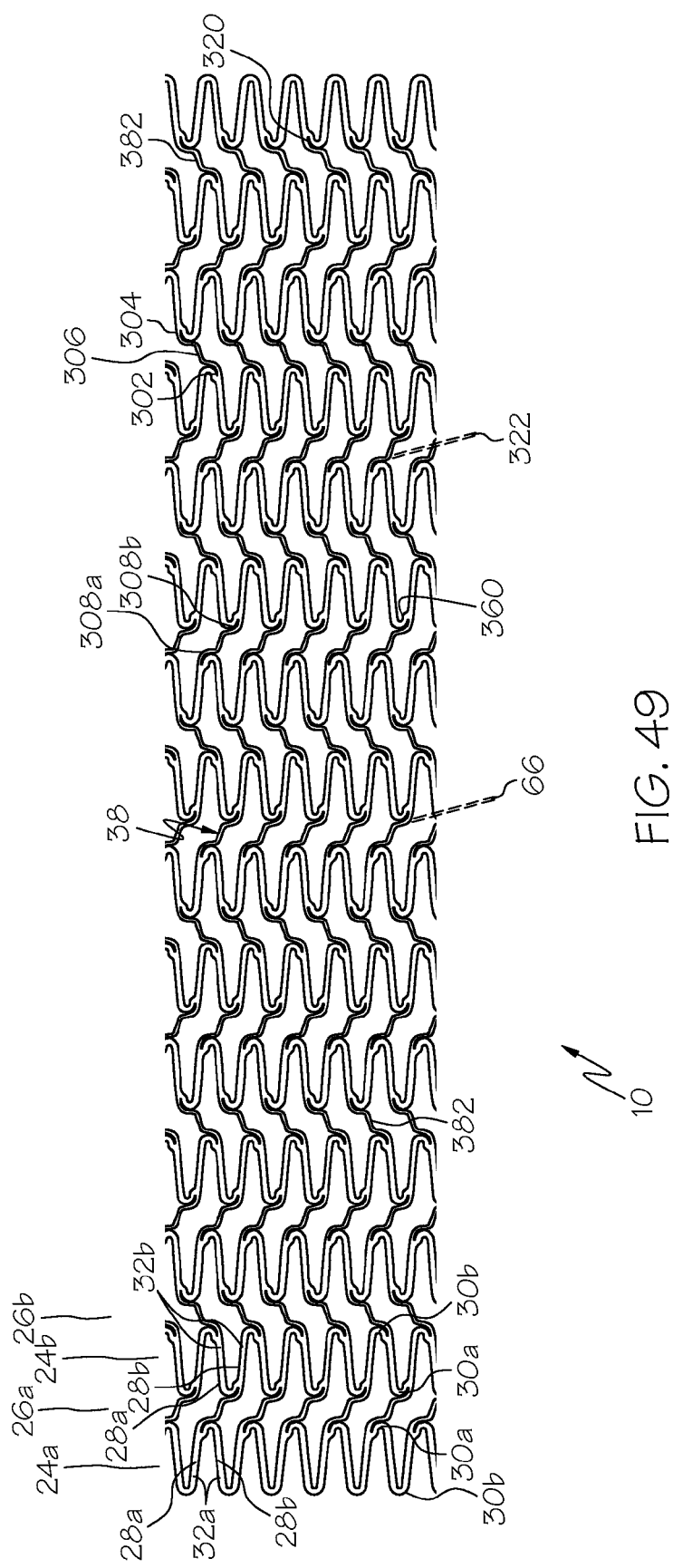
Figure 50:
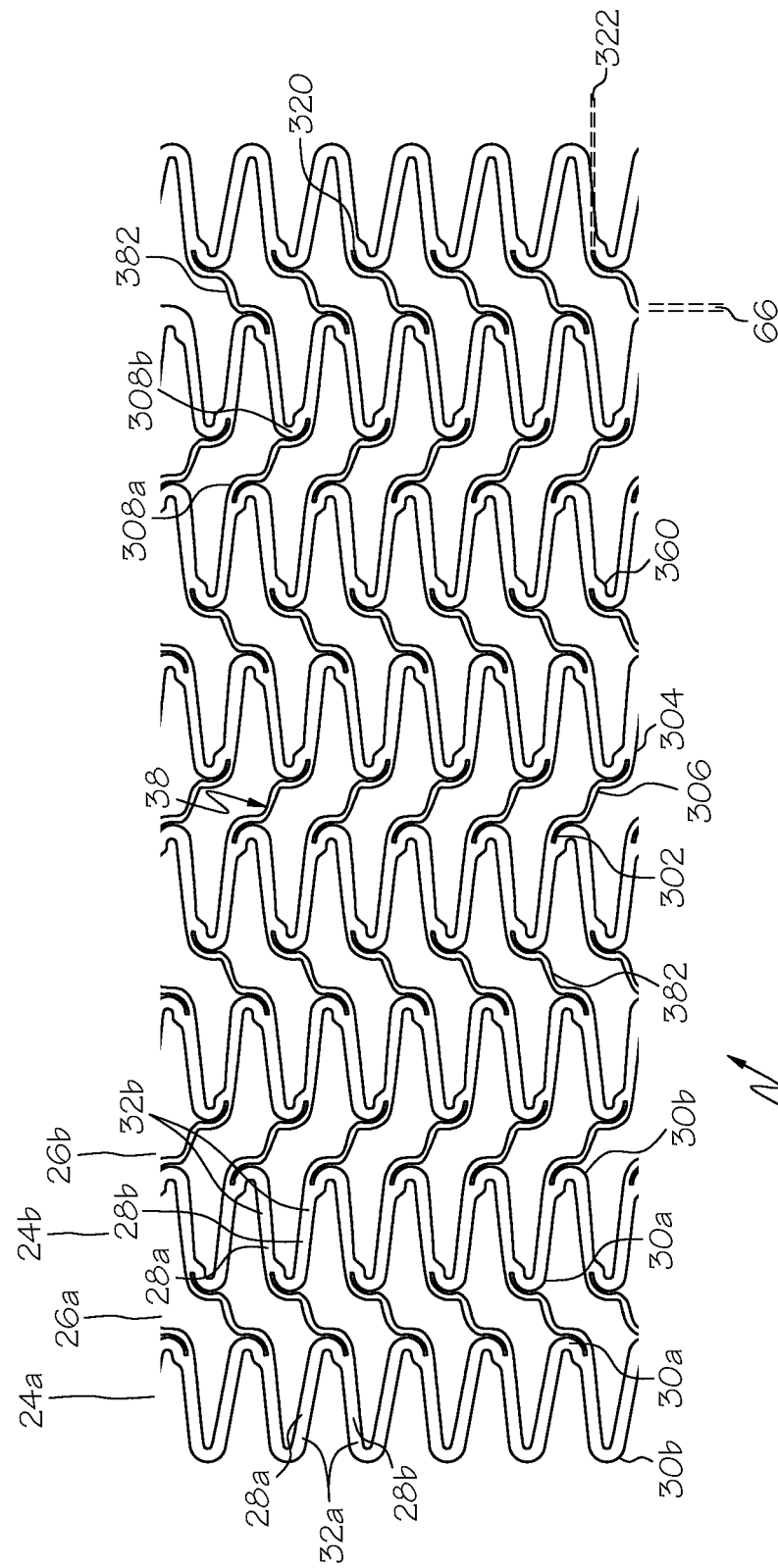
Figure 51:
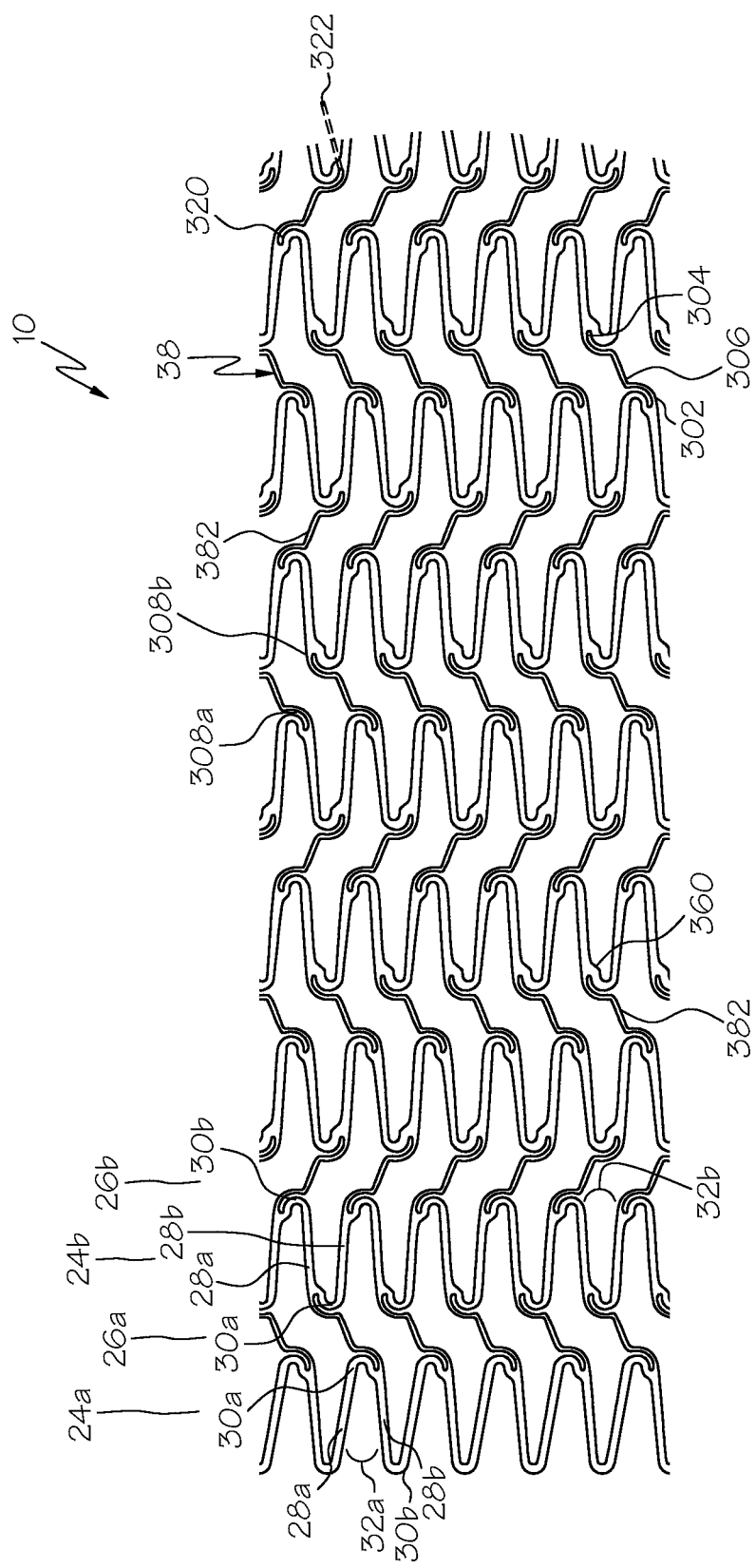
Figure 52:
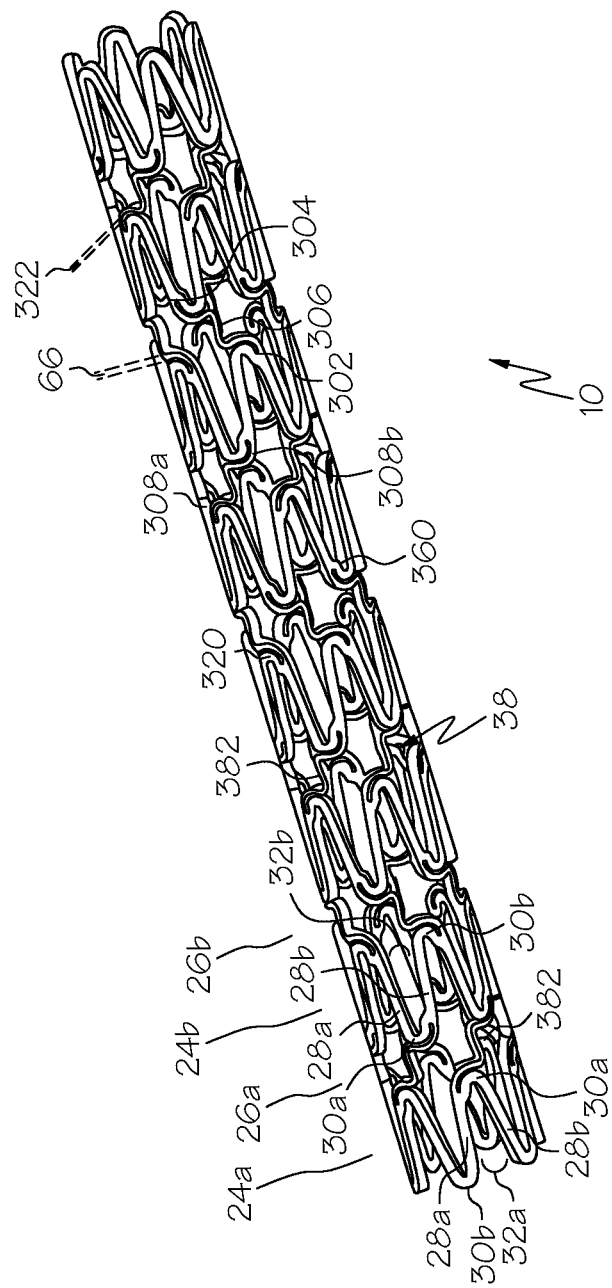
Figure 53:
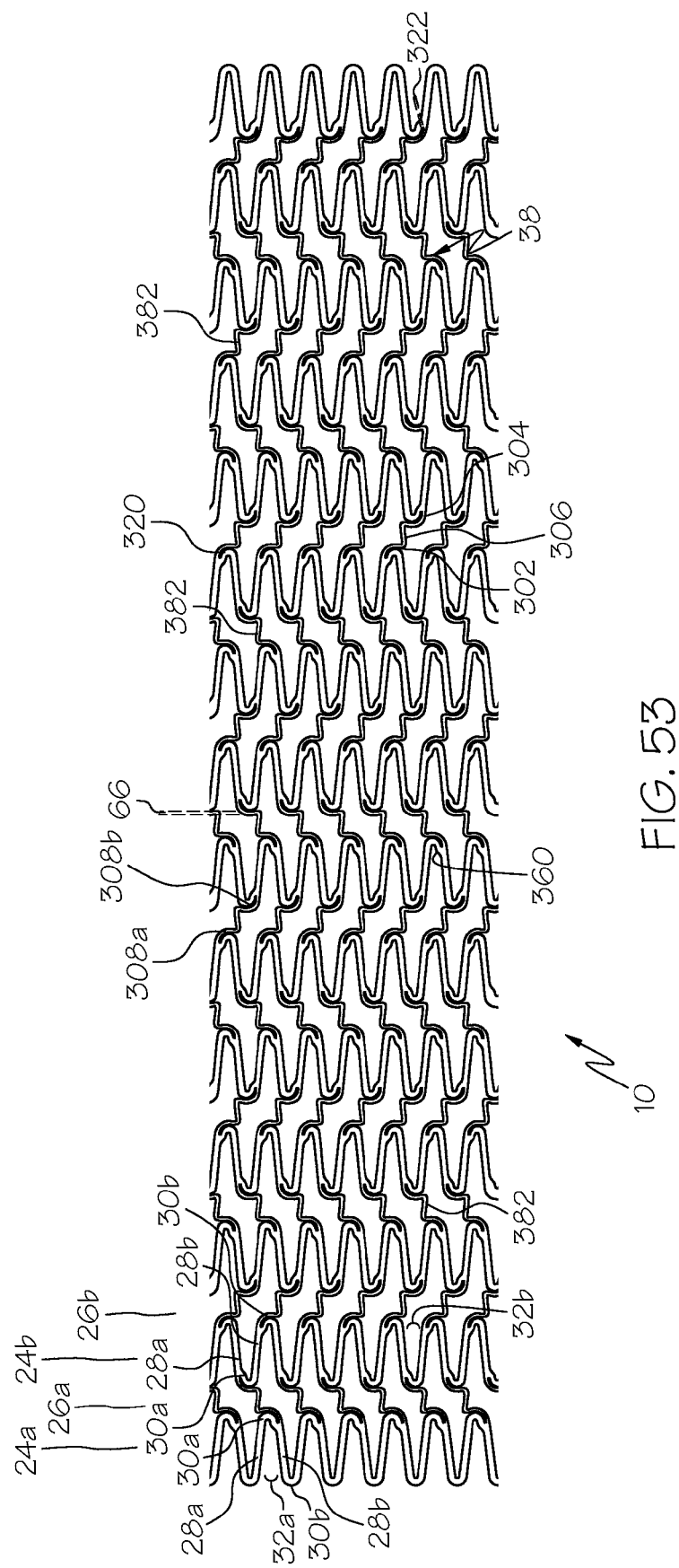
Figure 54:
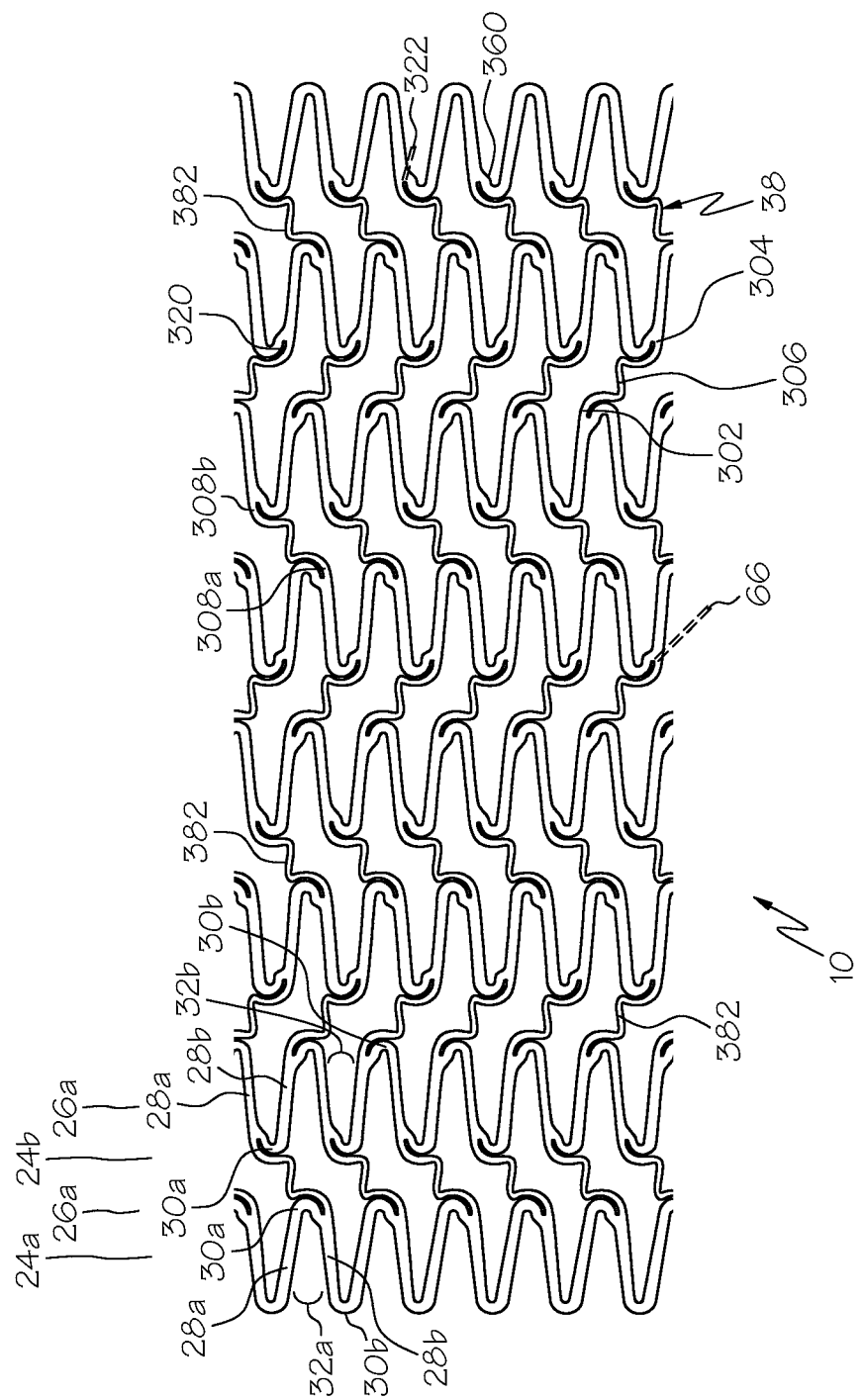
Figure 55:
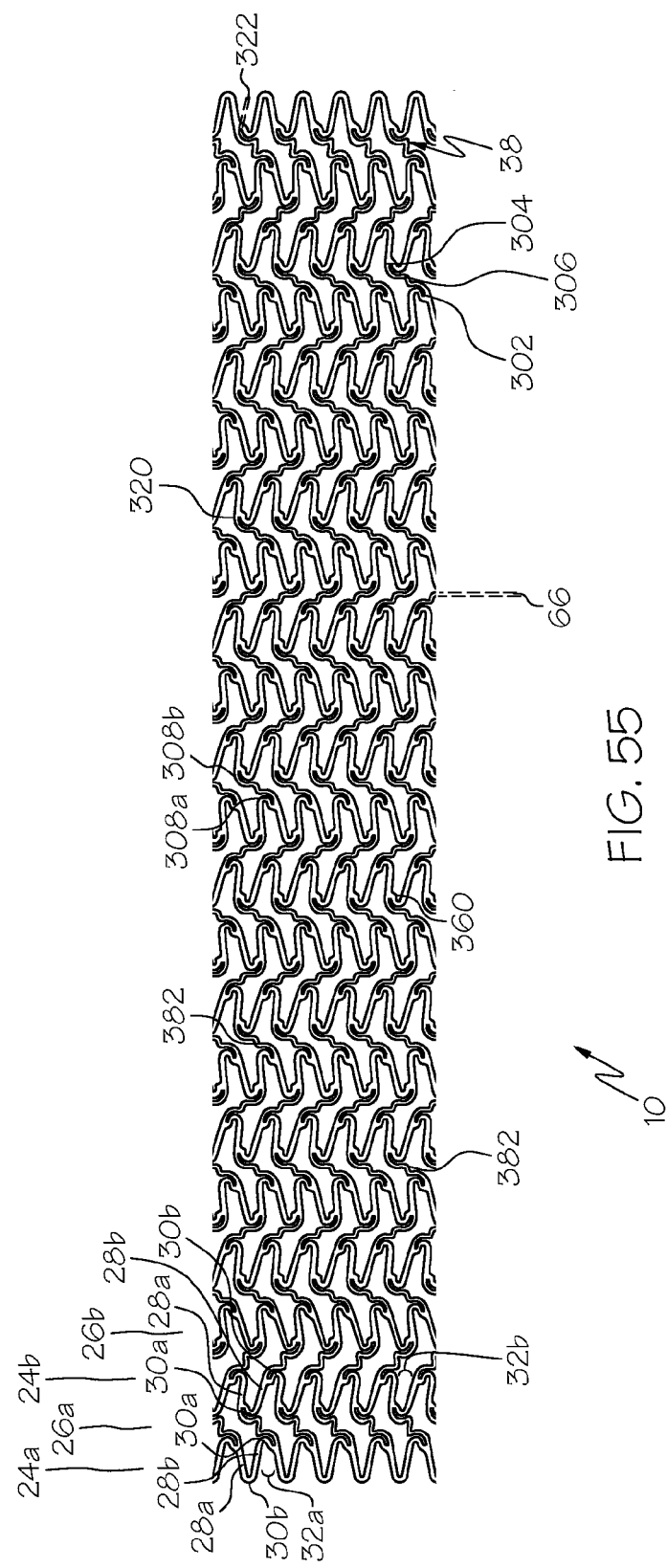
Figure 56:
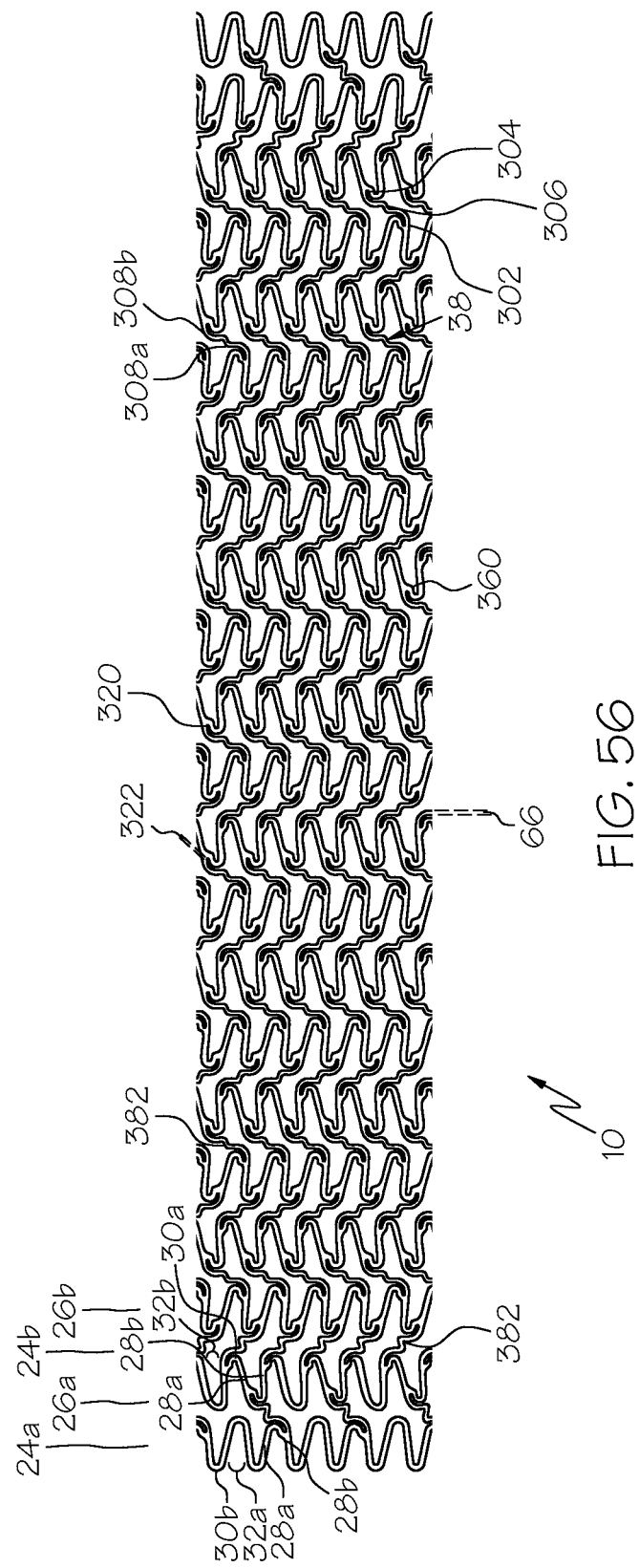
Figure 57:
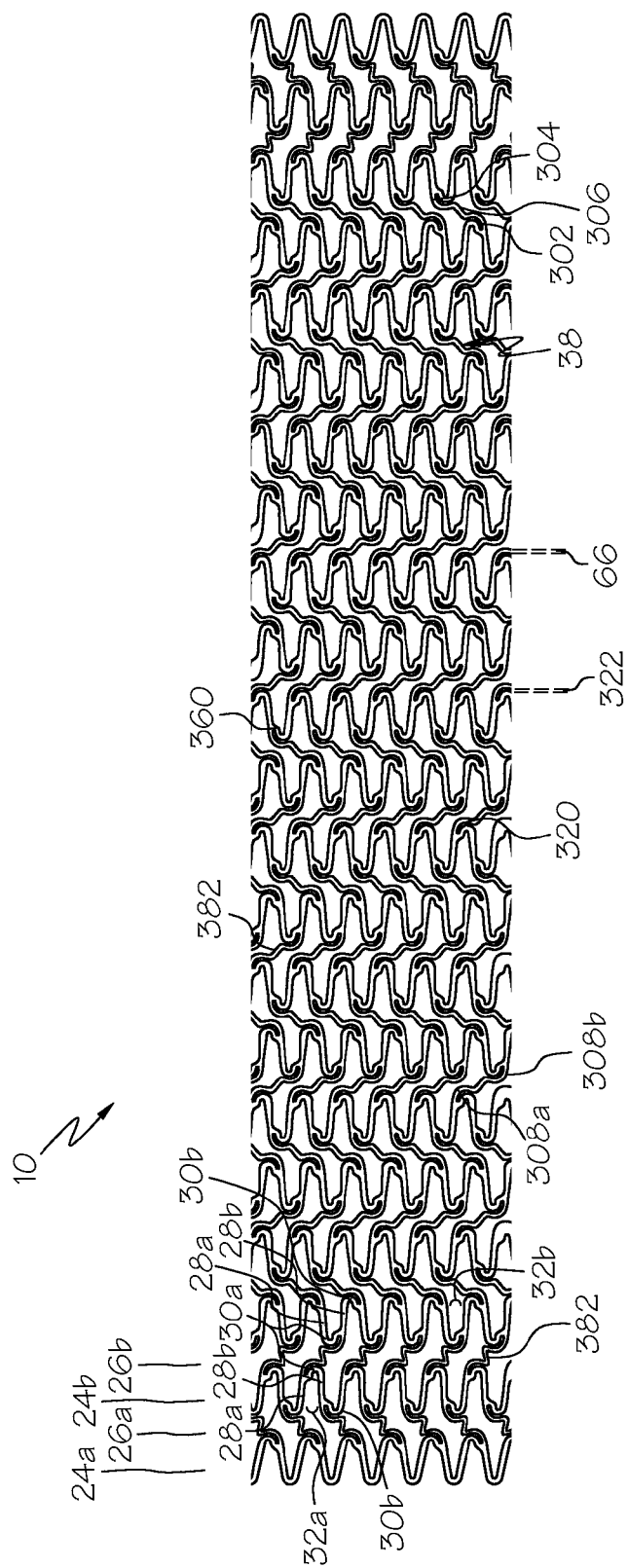
Figure 58:
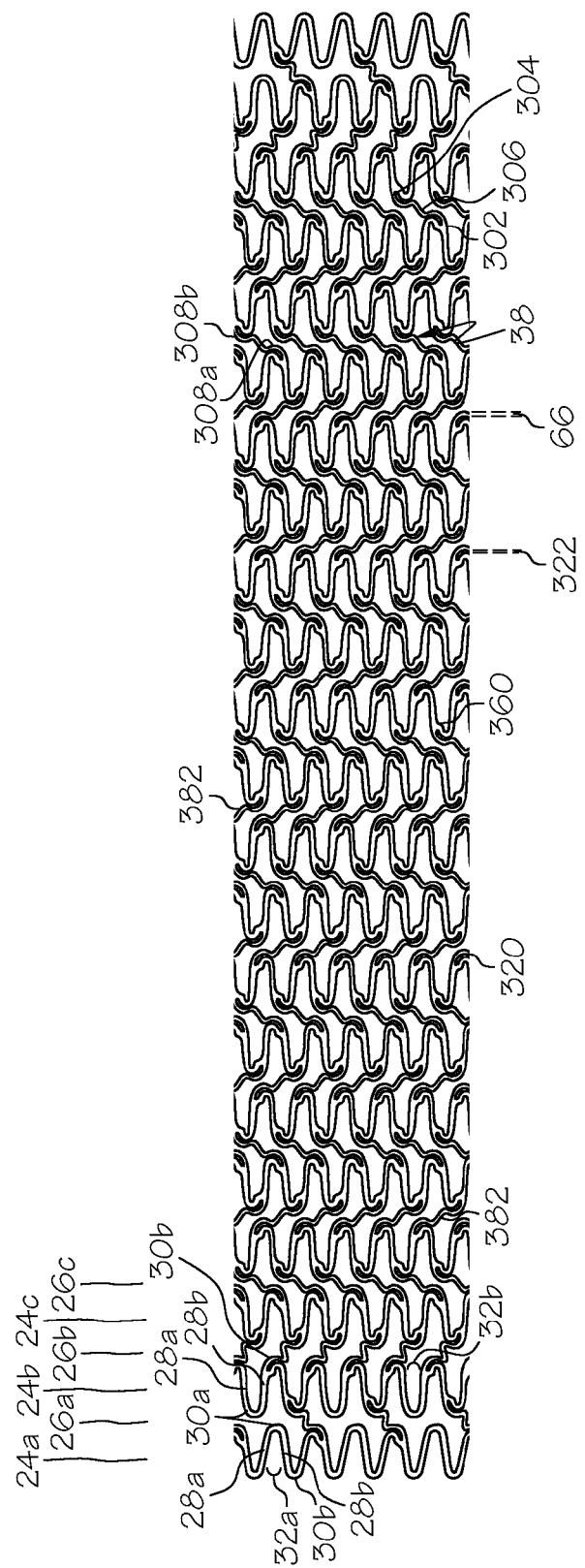
Figure 59:
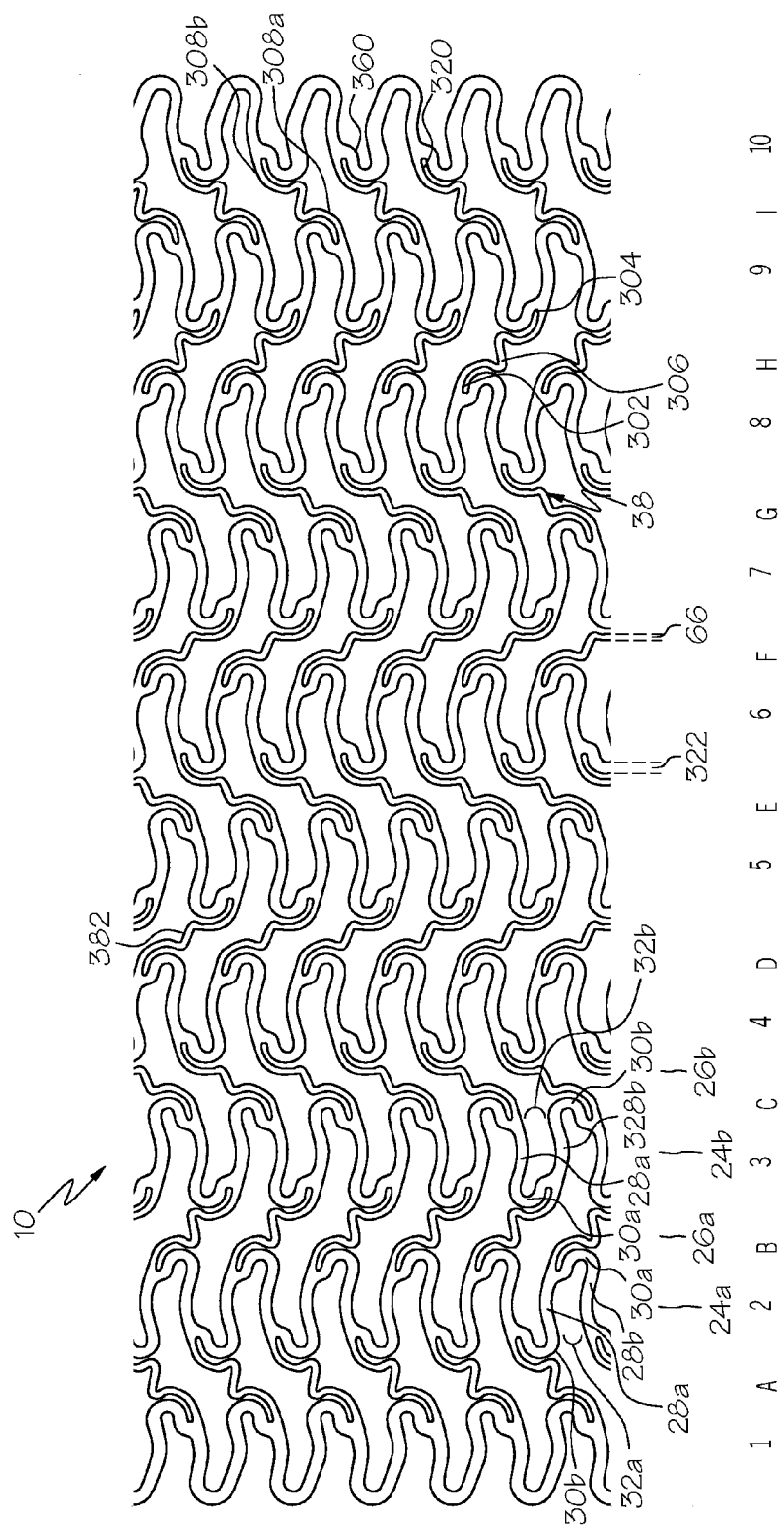
Figure 60:
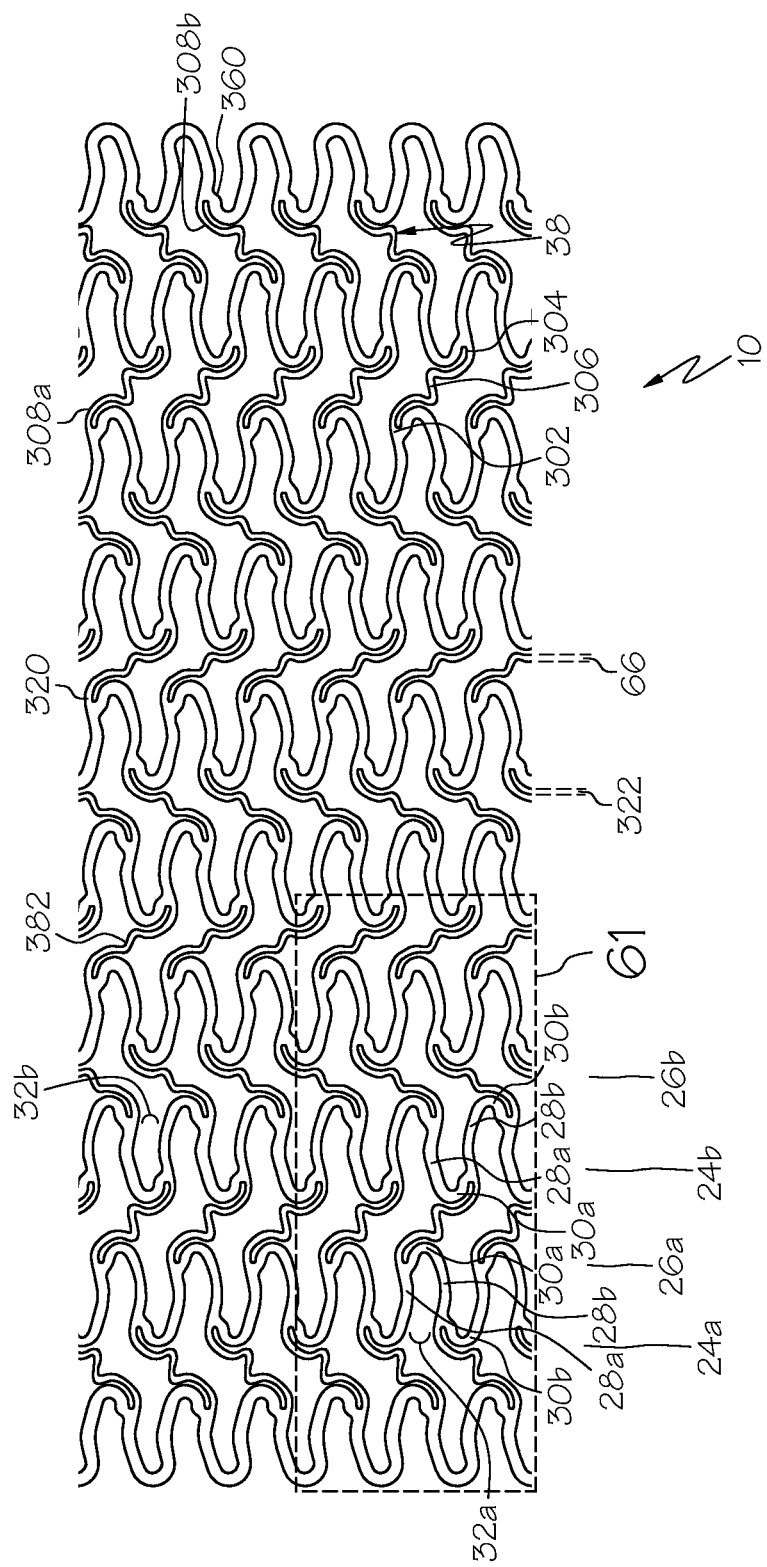
Figure 61:
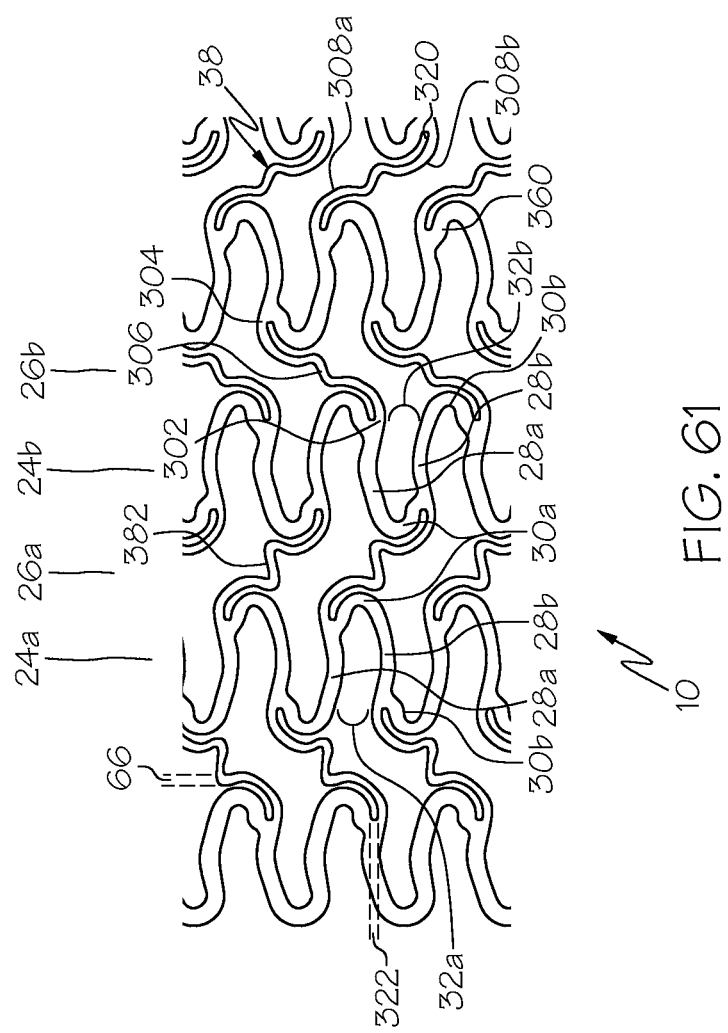
Figure 62:
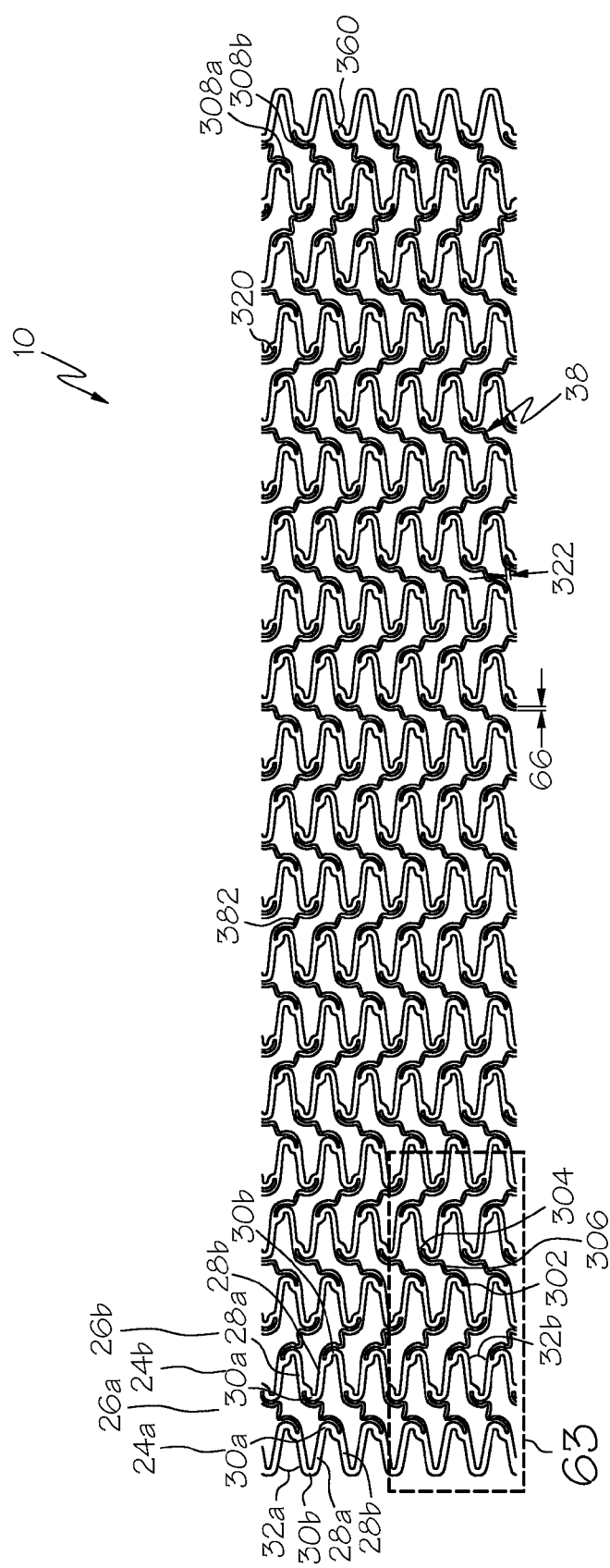
Figure 63:
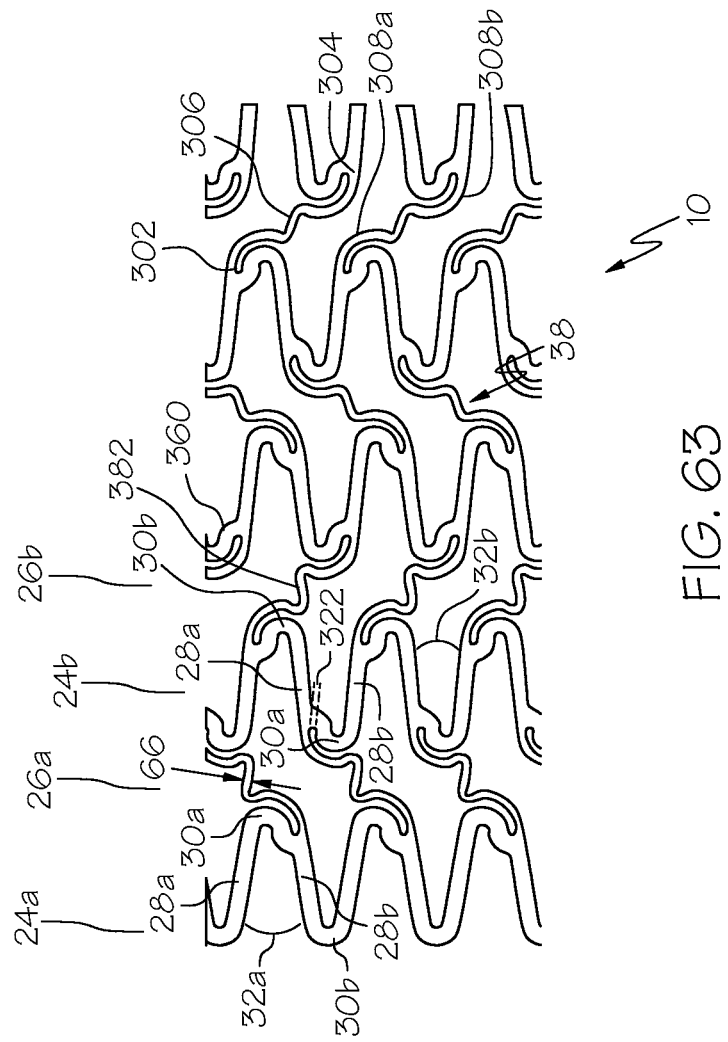
Figure 64:
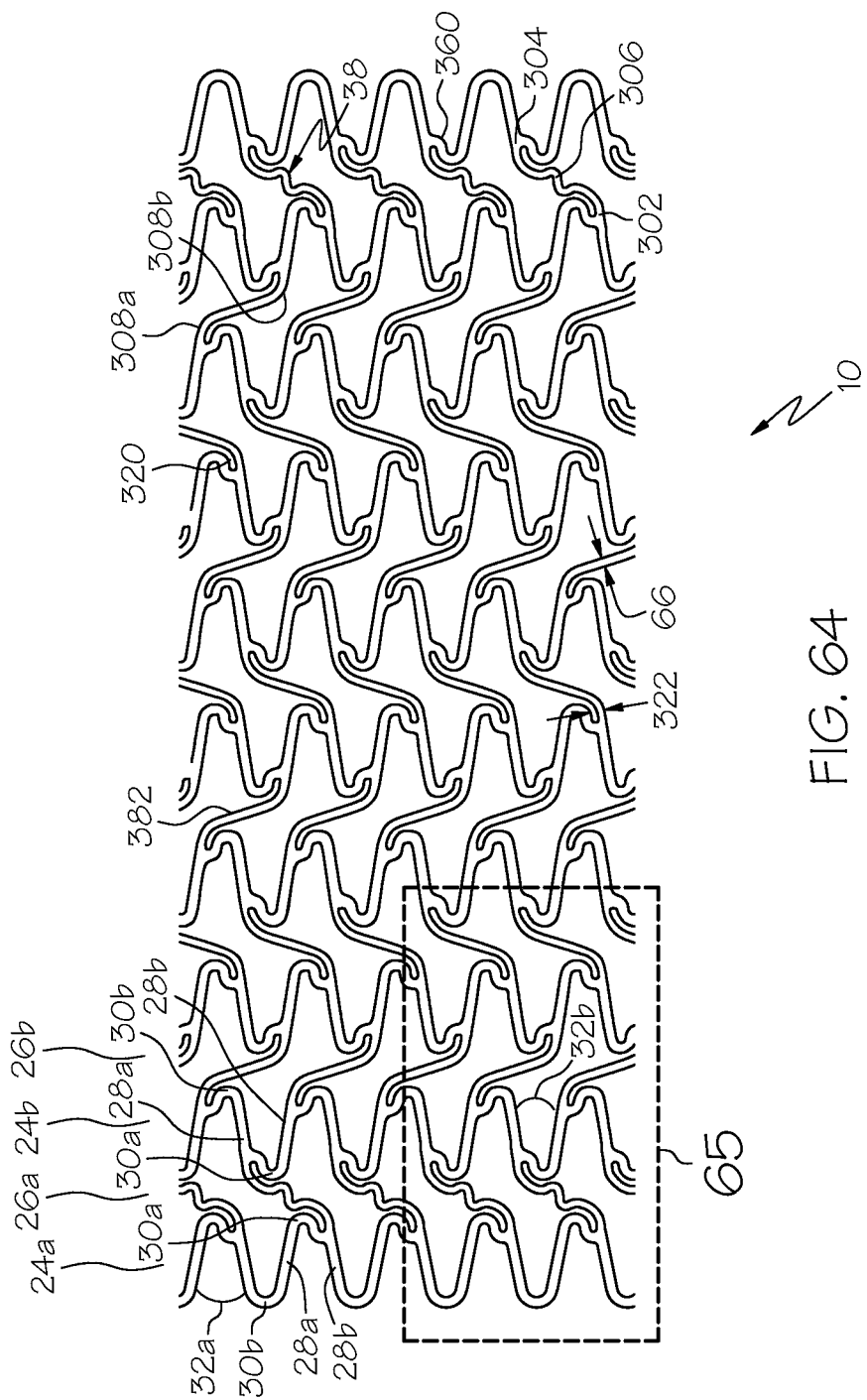
Figure 67:
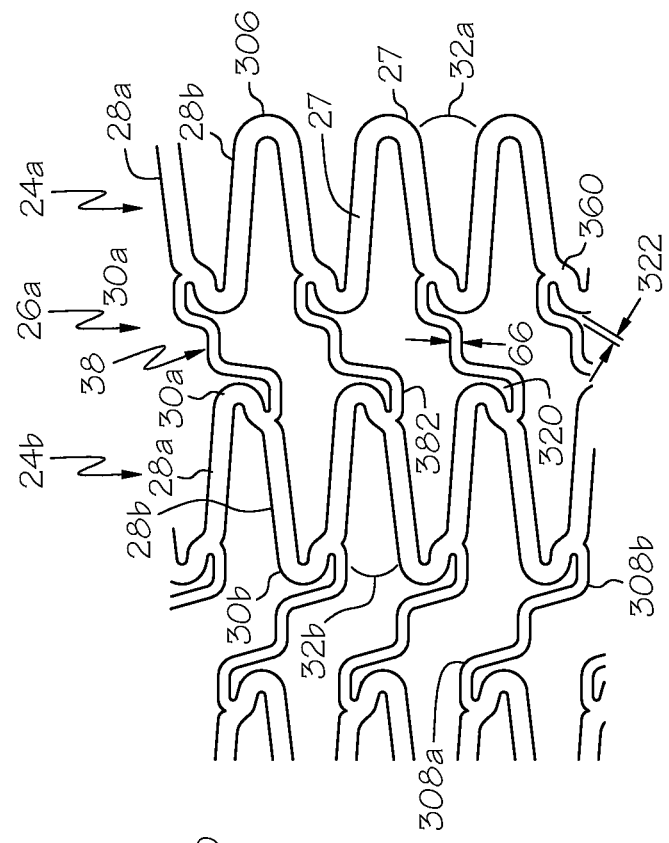
Figure 66:
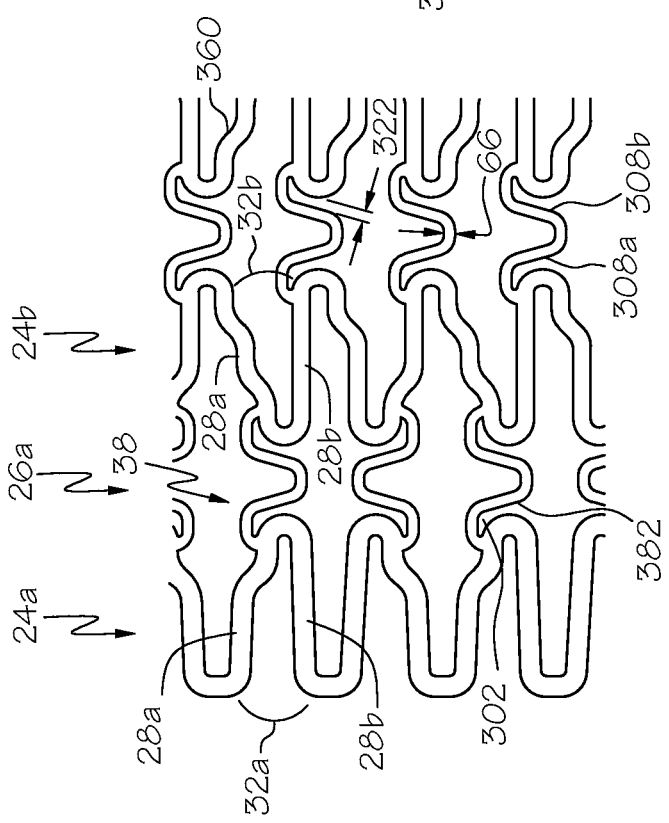

FIG. 46 is a partial side view of a configuration of the embodiment shown in FIG. 44.
FIG. 47 is a partial side view of a configuration of the embodiment shown in FIG. 44.
FIG. 48 is a perspective view of an embodiment of the invention.
FIG. 49 is a side view of the embodiment shown in FIG. 48.
FIG. 50 is an enlarged side view of the embodiment shown in FIG. 48
FIG. 51 is a partial side view of a configuration of the embodiment shown in FIG. 48.
FIG. 52 is a perspective view of an embodiment of the invention.
FIG. 53 is a side view of an embodiment of the invention.
FIG. 54 is a side view of an embodiment of the invention.
FIG. 55 is a side view of an embodiment of the invention.
FIG. 56 is a side view of an embodiment of the invention.
FIG. 57 is a side view of an embodiment of the invention.
FIG. 58 is a side view of an embodiment of the invention.
FIG. 59 is a side view of an embodiment of the invention.
FIG. 60 is a side view of an embodiment of the invention.
FIG. 61 is an enlarged sectional view of the embodiment shown in FIG. 61.
FIG. 62 is a side view of an embodiment of the invention.
FIG. 63 is an enlarged sectional view of the embodiment shown in FIG. 62.
FIG. 64 is a side view of an embodiment of the invention.
FIG. 65 is an enlarged sectional view of the embodiment shown in FIG. 64
FIG. 66 is a partial side view of an embodiment of the invention.
FIG. 67 is a partial side view of an embodiment of the invention.

DETAILED DESCRIPTION OF THE INVENTION

While this invention may be embodied in many different forms, there are described in detail herein embodiments of the invention. This description is an exemplification of the principles of the invention and is not intended to limit the invention to the particular embodiments illustrated.

For the purposes of this disclosure, like reference numerals in the figures shall refer to like features unless otherwise indicated.

An embodiment of the present invention is shown in FIGS. 1A, 1B, 1C, 2A and 2B. Referring to FIG. 1A, an elongate hollow tubular stent 10 in an unexpanded state is shown.

It is understood that a stent may have a variety of expansion states which provide the stent with a variety of different stent diameters that will vary depending on the specific expansion state the stent is in. The term "unexpanded" as used herein refers to one or more of such configurations and/or diameters prior to implantation of the stent into a body lumen.

A proximal end 12 and a distal end 14 define a longitudinal length 16 of stent 10. The longitudinal length 16 of the stent 10 can be as long as 100 mm or longer. A proximal opening 18 and a distal opening 20 connect to an inner lumen 22 of stent 10. Stent 10 can be a single piece, without any seams or welding joints or may include multiple pieces.

Stent 10 is constructed of two to fifty or more expansion columns or rings 24 connected together by interspersed connecting strut columns 26. The first column on the proximal end 12 and the last column on the distal end 14 of stent 10 are expansion columns 24.

Expansion columns 24 are formed from a series of expansion struts 28, and joining struts 30. Expansion struts 28 are elongate members arranged so that they extend at least in part in the direction of the longitudinal axis of stent 10. When an outward external force is applied to stent 10 from the inside by an expansion balloon or other means, or when the stent 10 is caused to self-expand, the expansion struts 28 are reoriented such that they extend in a more circumferential direction, i.e. along the surface of cylindrical stent 10 and perpendicular to its longitudinal axis. Reorientation of expansion struts 28 causes stent 10 to have an expanded circumference and diameter. In the embodiment shown in FIG. 1A, expansion struts 28 of unexpanded stent 10 are seen to extend substantially parallel to the longitudinal axis of stent 10.

Expansion struts 28 are joined together by joining struts 30 to form a plurality of expansion strut pairs 32. Expansion strut pairs have a closed end 34 and an open end 36. Additional joining struts 30 join together expansion struts 28 of adjacent expansion strut pairs 32, such that expansion struts 28 are joined alternately at their proximal and distal ends to adjacent expansion struts 28 to form expansion columns 24. Each expansion column 24 contains a plurality, typically eight to twenty, twenty to sixty, or more of expansion struts 28. Expansion columns are preferably continuous unbroken ring structures extending around the circumference of the stent 10; however, broken structures in which individual struts or pieces of struts are removed from an otherwise continuous expansion column 24 can also be used.

Connecting struts 38 connect adjacent expansion columns 24 forming a series of interspersed connecting strut columns 26 each extending around the circumference of stent 10. Each connecting strut 38 joins a pair of expansion struts 28 in an expansion column 24 to an adjacent pair of expansion struts 28 in an adjacent expansion column 24. For stent 10 of FIG. 1A, the ratio of expansion struts 28 in an expansion column 24 to connecting struts 38 in a connecting strut column 26 is two to one; however, this ratio in general can be X to 1 where X is greater or less than two. Other ratios may also be utilized. Furthermore, since the stent 10 of FIG. 1A begins with an expansion column 24 on the proximal end 12 and ends with an expansion column 24 on the distal end 14, if there are n expansion columns 24 with m expansion struts 28 per column, there will be m−1 connecting strut columns 26, and n(m−1)/2 connecting struts 38.

The reduced number of connecting struts 38 in each connecting strut column 26, as compared to expansion struts 28 in each expansion column 24, allows stent 10 to be longitudinally flexibility. Longitudinal flexibility can be further increased by using a narrow width connecting strut, providing additional flexibility and suppleness to the stent as it is navigated around turns in a natural blood vessel. In some embodiments at least one portion of one or more the connecting struts 38 may have a width different than that of one or more adjacent portions.

At least a portion of the open spaces between struts in stent 10 form asymmetrical cell spaces 40. A cell space or geometric cell is an empty region on the surface of stent 10, completely surrounded by one or a combination of stent struts, including expansion struts 28, connecting struts 38, or joining struts 30. Asymmetrical cell spaces 40 are cell spaces which have no geometrical symmetry i.e. no rotation, reflection, combination rotation and reflection or other symmetry. Asymmetrical cell spaces 40 have an asymmetrical geometric configuration.

Asymmetrical cell spaces 40 in FIG. 1A are surrounded by a first expansion strut pair 32 in a first expansion column 24, a first connecting strut 38, a second expansion strut pair 32 in an adjacent expansion column 24, a first joining strut 30, a second connecting strut 38, and a second joining strut 30. Furthermore, expansion strut pairs 32 of asymmetrical cell space 40 may be circumferentially offset i.e. have longitudinal axes that are not collinear and have their open ends 36 facing each other. The space between two expansion struts of an expansion strut pair 32 is known as a loop slot 42.

FIG. 1B shows inner lumen 22, radius 44 and stent wall 46 of stent 10. Stent wall 46 is comprised of stent struts including expansion struts 28, connecting struts 38 and joining struts 30.

FIG. 1C shows, proximal end 12, distal end 14, longitudinal length 16, inner lumen 22, and stent wall 46 of stent 10. Inner lumen 22 is surrounded by stent wall 46 which forms the cylindrical surface of stent 10.

Figure 2B:
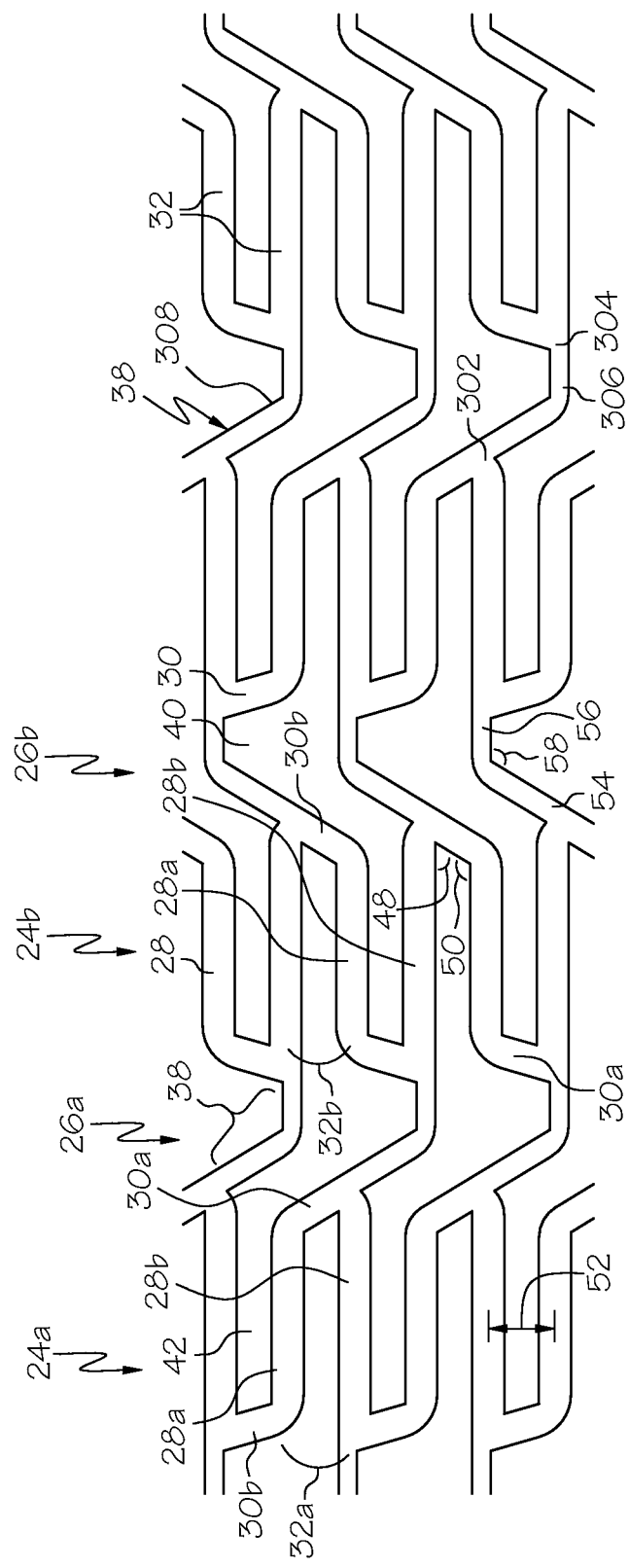
FIG. 2B is an expanded view of a section of the pattern of FIG. 2A.

Referring now to FIGS. 2A and 2B, joining struts 30 of stent 10 are seen to extend at an angle to the expansion struts 28, forming a narrow angle 48 with one expansion strut 28 in an expansion strut pair 32 and a wide angle 50 with the other expansion strut 28 of an expansion strut pair 32. Narrow angle 48 is less than ninety degrees, while wide angle 50 is greater than ninety degrees. Joining struts 30 extend both longitudinally along the longitudinal axis of stent 10 and circumferentially, along the surface of the stent 10 perpendicular to its longitudinal axis.

Expansion strut spacing 52 between adjacent expansion struts 28 in a given expansion column 24 are uniform in stent 10 of FIGS. 2A and 2B; however, non-uniform spacings can also be used. Expansion strut spacings 52 can be varied, for example, spacings 52 between adjacent expansion struts 28 in an expansion column 24 can alternate between a narrow and a wide spacings. Additionally, spacings 52 in a single expansion column 24 can differ from other spacings 52 in other columns 24.

It is noted that varying expansion strut spacings 52 which form the loop slots 42 results in variable loop slot widths. Furthermore, the longitudinal axis of the loop slots 42 need not be collinear or even parallel with the longitudinal axis of loop slots 42 of an adjacent expansion column 24. FIGS. 2A and 2B show an arrangement of expansion struts 28 such that collinear, parallel adjacent loop slots 42 are formed, but non-collinear and non-parallel loop slots 42 can also be used.

Additionally the shape of loop slots 42 need not be the same among loop slots of a single or multiple expansion columns 24. The shape of loop slots 42 can be altered by changing the orientation or physical dimensions of the expansion struts 28 and/or joining struts 30 which connect expansion struts 28 of expansion strut pairs 32 defining the boundaries of loop slots 42.

Connecting struts 38 couple adjacent expansion columns 24, by connecting the distal end of an expansion strut pair in one expansion column 24 to the proximal end of an adjacent expansion strut pair 32 in a second expansion column 24. Connecting struts 38 of FIGS. 2A and 2B are formed from two linear sections, a first linear section 54 being joined at its distal end to a second linear section 56 at its proximal end to form a first slant angle 58.

The first linear section 54 of a connecting strut 38 is joined to expansion strut 28 at the point where joining strut 30 makes narrow angle 48 with expansion strut 28. First linear section 54 extends substantially collinear to joining strut 30 continuing the line of joining strut 30 into the space between expansion columns 24. The distal end of the first linear section 54 is joined to the proximal end of the second linear section 56 forming slant angle 58. Second linear section 56 extends substantially parallel to expansion struts 28 connecting at its distal end to joining strut 30 in an adjacent expansion column 24. The distal end of second linear section 56 attaches to expansion strut 28 at the point where joining strut 30 makes narrow angle 48 with expansion strut 28. Further, joining strut 30 can have a second slant angle with a width that can be the same or different from the width of the first slant angle.

FIGS. 2A and 2B show connecting struts 38 and joining struts 30 slanted relative to the longitudinal axis of stent 10, with the circumferential direction of the slanted struts alternating from column to adjacent column. Circumferential direction refers to the handedness with which the slanted struts wind about the surface of the stent 10. The circumferential direction of the slant of connecting strut first linear sections 54 in a connecting strut column 26 is opposite the circumferential direction of the slant of connecting strut first linear sections 54 in an adjacent connecting strut column 26. Similarly, the circumferential direction of the slant of joining struts 30 in an expansion column 24 is opposite the circumferential direction of the slant of joining struts 30 in an adjacent expansion column 24. Alternating circumferential slant directions of connecting struts 38 and joining struts 30 prevents axial warping of stent 10 during deliver and expansion. Other non-alternating slant direction patterns can also be used for connecting struts 38 or joining struts 30 or both.

FIGS. 3A and 3B show a schematic illustration of a stent design according to the present invention in an unexpanded and expanded state respectively. The design is depicted as a flat projection, as if stent 10 were cut lengthwise parallel to its longitudinal axis and flattened out. The connecting struts 38 comprise first and second linear sections 54 and 56 forming slant angle 58 at pivot point 60. An asymmetrical cell space 40 is formed by expansion strut pairs 32, connecting struts 38 and joining struts 30. Multiple interlocking asymmetrical cell spaces 40 make up the design pattern.

As the stent is expanded, see FIG. 3B, the expansion strut pairs 32 spread apart at their open ends 36, shortening the length of expansion struts 28 along the longitudinal axis of the cylindrical stent. The longitudinal shortening of expansion struts 28 during expansion is countered by the longitudinal lengthening of connecting struts 38. The widening of slant angle 58 during expansion straightens connecting struts 38 and lengthens the distance between the coupled expansion strut pairs 32. The widening of the slant angle of connecting struts 38 substantially compensates for the longitudinal shortening of expansion struts 28. Thus, the stent has substantially constant unexpanded and expanded longitudinal lengths.

When the stent is expanded, each expansion column 24 becomes circumferentially stretched, enlarging the space between struts. The interlinking of expansion columns 24 by connecting struts 38 that have been straightened through the expansion process gives the stent 10a high radial support strength. The entire stent 10 when expanded is unitized into a continuous chain mesh of stretched expansion columns 24 and connecting strut columns 26 forming an asymmetrical interlocking cell geometry which resists collapse both axially and radially. When the stent is expanded it has increased rigidity and fatigue tolerance.

In addition, efficient bending and straightening of connecting struts 38 at pivot points 60 allows increased longitudinal flexibility of the stent. For the stent to bend longitudinally, at least some of connecting struts 38 are forced to bend in their tangent plane. The tangent plane of a specific connecting strut 38 refers to the plane substantially tangent to the cylindrical surface of the stent at that connecting strut 38. The width of connecting struts 38 can be twice as wide as a thickness. In some embodiments a one-to-one ratio may be provided for, however other configurations and ratios of thickness to width may be utilized. However, pivot points 60 in connecting struts 38 provide connecting struts 38a flexible joint about which to more easily bend increasing longitudinal flexibility of the stent.

Referring to FIGS. 4A and 4B, an embodiment of the stent 10 of the present invention is shown. In this embodiment stent 10 has a length 16 of 33.25 mm and an uncrimped and unexpanded circumference 88 of 5.26 mm. Fifteen expansion columns 24 are interspersed with connecting strut columns 26. Each expansion column 24 is comprised of twelve expansion struts 28 joined alternately at their proximal and distal ends by joining struts 30 forming six expansion strut pairs 32. Expansion struts 28 are aligned parallel to the longitudinal axis of cylindrical stent 10. Joining struts 30 form a narrow angle 48 and a wide angle 50 with the respective expansion struts 28 of expansion strut pairs 32. Adjacent expansion columns 24 employ alternating circumferential slant directions of joining struts 30.

In this embodiment expansion strut width 62 is 0.20 mm, expansion strut length 64 is 1.51 mm, and connecting strut width 66 is 0.13 mm. Distance 68 from the outer edge of a first expansion strut 28 to the outer edge of a second adjacent expansion strut 28 in the same expansion column 24 is 0.64 mm, leaving a loop slot width 70 of 0.24 mm.

In this embodiment, connecting struts 38 is comprised of a slanted first linear section 54 joined to a second linear section 56 at a slant angle 58. First linear section 54 is slightly longer than second linear section 56 and is attached at its proximal end to an expansion strut 28 in an expansion column 24. The attachment of the proximal end of first linear section 54 to expansion strut 28 is at the point where joining strut 30 makes narrow angle 48 with expansion strut 28. First linear section 54 extends substantially collinear to joining strut 30 attaching at its distal end to the proximal end of second linear section 56 to form slant angle 58. Second linear section 56 extends substantially collinear to expansion struts 28, attaching at its distal end to an expansion strut 28 in an adjacent expansion column 24. The attachment occurs at the point where expansion strut 28 forms narrow angle 48 with joining strut 30. Joining struts 30 and connecting strut first linear sections 54 slant in alternating circumferential directions from column to adjacent column.

The joining of connecting struts 38 and expansion struts 28 at the point where narrow angle 48 is formed aids smooth delivery of stent 10 by streamlining the surface of the unexpanded stent and minimizing possible catching points. Bare delivery of stent 10 to the target lesion in a vessel will thus result in minimal snagging or catching as it is navigated through turns and curvatures in the vessel. Stent 10 behaves like a flexible, tubular sled as it is moved forward or backward in the vessel on the delivery catheter, sliding through tortuous vessels and over irregular bumps caused by atherosclerotic plaques inside the vessel lumen.

When fully expanded the stent 10 of FIGS. 4A and 4B has an internal diameter of up to 5.0 mm or more, while maintaining an acceptable radial strength and fatigue tolerance. The crimped stent outer diameter can be as small as 1.0 mm or less depending on the condition of the underlying delivery balloon profile; a small crimped outer diameter is especially important if stent delivery is to be attempted without predilation of the target site. When the stent is optimally crimped over the delivery balloon, the surface of the crimped stent is smooth allowing for no snagging of the stent struts during either forward or backward movement through a vessel.

Figure 5:
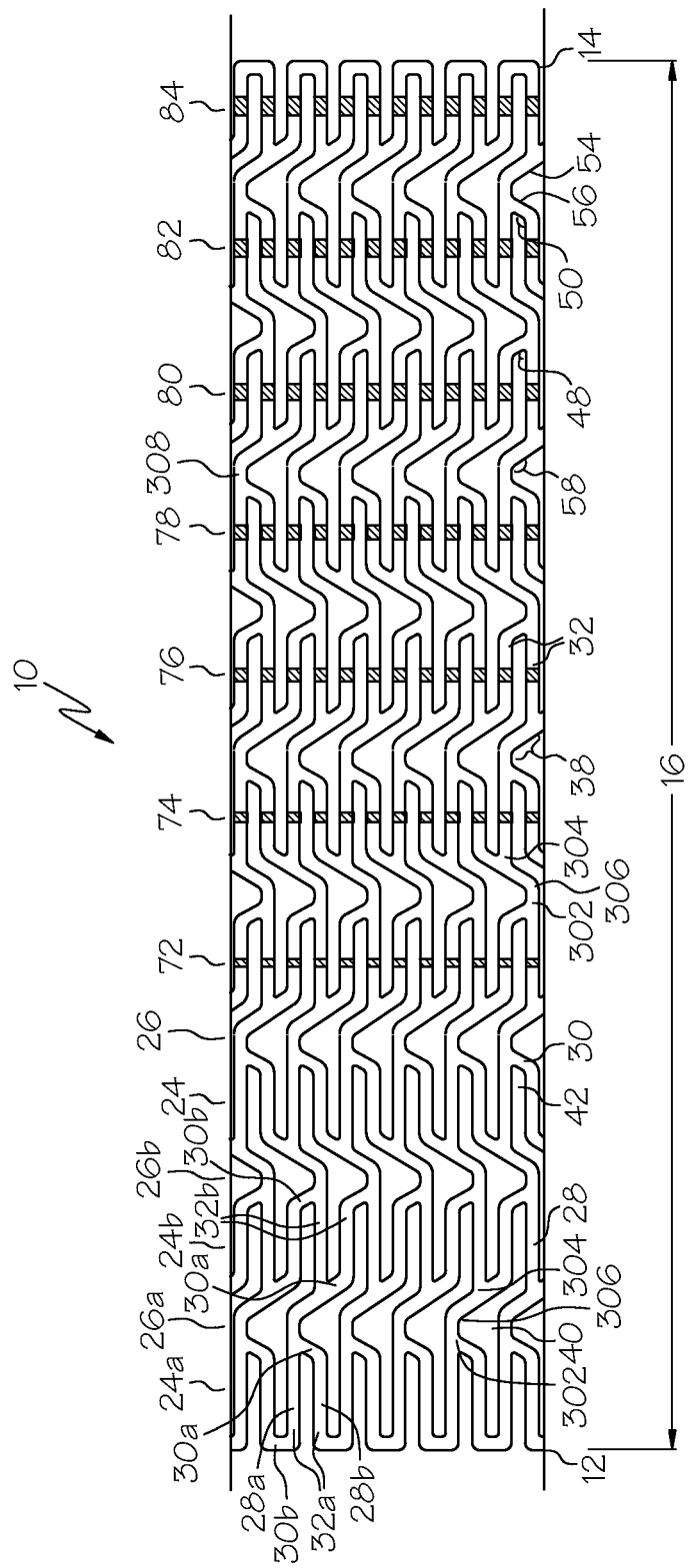
FIG. 5 is a scale drawing of an embodiment of the stent of the present invention with a tapered diameter in its post-expansion mode.

FIG. 5 shows an embodiment of the present invention in which the stent 10 in its expanded form has a gradual taper from proximal end 12 to distal end 14. The shaded segments 72, 74, 76, 78, 80, 82 and 84 of expansion struts 28 represent regions of expansion struts 28 to be removed. Removal of the shaded segments 72, 74, 76, 78, 80, 82 and 84 provides stent 10 with a gradual taper when expanded with distal end 14 having a smaller expanded diameter than proximal end 12. The degree of shortening of the expanded diameter of the stent 10 at a given expansion column 24 will be proportional to the length of the removed segment 72, 74, 76, 78, 80, 82, or 84 at that expansion column 24. In the expanded stent 10 the shortened expansion struts 28 will have a shortened component along the circumference of the stent resulting in a shortened circumference and diameter. The tapered diameter portion can be positioned anywhere along the length of stent 10, and the tapering can be made more or less gradual by removing appropriately larger or smaller portions of the expansion struts 28 in a given expansion column 24.

Tapering may be especially important in long stents, longer than 12 mm, since tapering of blood vessels is often more pronounced over longer lengths. Thus in some embodiments it is desirable to have a stent with a tapered expanded diameter.

Another way to achieve a tapered expanded stent is to change the stiffness of the stent struts, expansion struts, connecting struts or joining struts such that the stiffness of the struts varies along the length of the stent. The stiffness of the struts can be changed by altering length, width or thickness, adding additional stiffening material, using a chemical or mechanical means to alter the physical properties of the stent material, or applying one or a series of elastic elements about the stent.

Along with the use of a tapered diameter stent, a matching tapered balloon catheter would ideally be made for delivery and deployment of the tapered diameter stent. The method of using a tapered matching balloon catheter with a tapered diameter stent is within the scope of the present invention.

Using a tapered balloon to expand a non-tapered stent will also achieve a tapered expanded stent; however, since no metal is removed from the stent, the stent is tapered as a result of incomplete expansion. The stent will therefore have increased metal fraction at the tapered end resulting in increased risk of acute thrombosis. Metal fraction is the proportion of the surface of the expanded stent covered by the stent strut material. Shortening the expansion struts as shown in FIG. 5 allows for a tapered expanded stent with substantially constant metal fraction along its length.

Figure 6B:
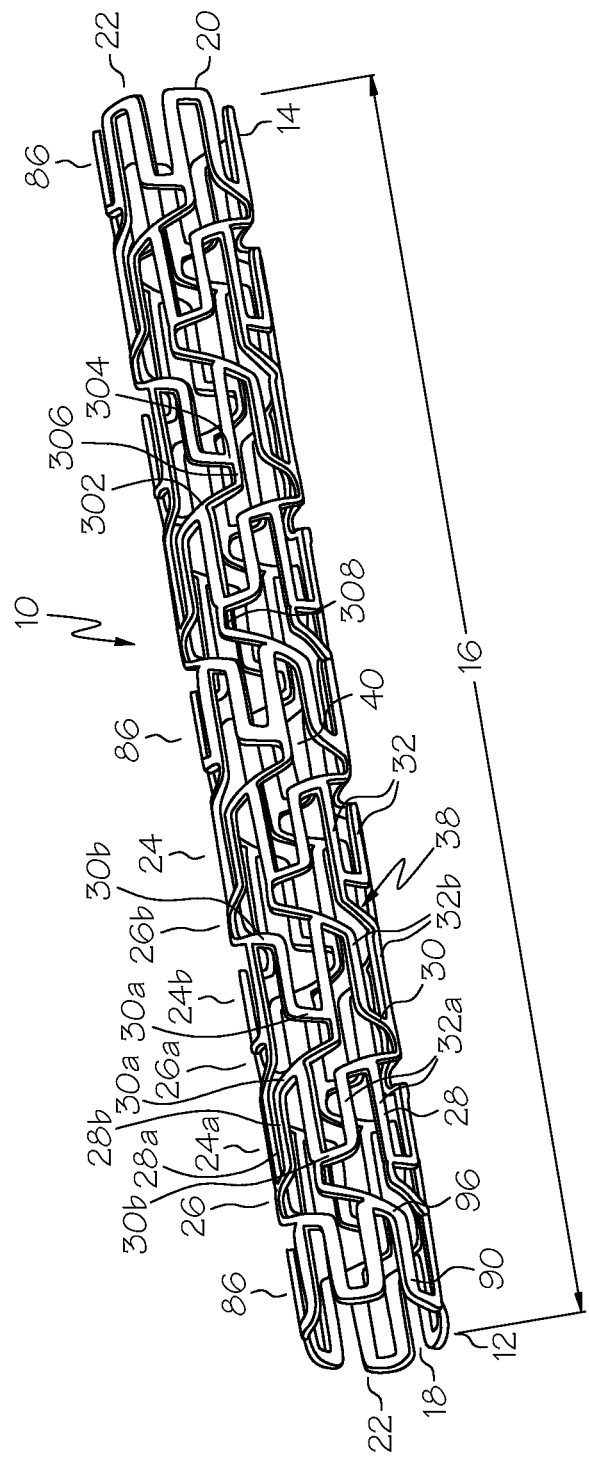
FIG. 6B is a perspective view of the embodiment of FIG. 6A.

Another embodiment of the present invention shown in FIGS. 6A and 6B has multiple re-enforcement expansion columns 86 placed along the length of the stent 10. The re-enforcement columns 86 are placed along the stent length to provide additional localized radial strength and rigidity to stent 10. Additional strength and rigidity are especially important at the ends of the stent to prevent deformation of the stent both during delivery and after placement. During delivery the stent ends can catch on the vessel wall possibly deforming the unexpanded stent and altering its expansion characteristics. After the stent has been placed it is important that the stent ends are rigid so that they set firmly against the vessel wall; otherwise, during a subsequent catheter procedure, the catheter or guidewire can catch on the stent ends pulling the stent away from the vessel wall and possibly damaging and/or blocking the vessel.

A variation of the embodiment of stent 10 depicted in FIGS. 6A, 6B, and 6C has a length 16 of 20.70 mm and an uncrimped and unexpanded circumference 88 of 5.26 mm. The stent 10 may comprise six expansion columns 24 and three re-enforcement expansion columns 86, each comprising respectively of twelve expansion struts 28 or re-enforcement expansion struts 90. The re-enforcement expansion columns 86 are positioned one at either end, and one along the length of the stent 10.

In some embodiments the expansion strut width 62 is 0.15 mm, re-enforcement expansion strut width 92 is 0.20 mm, and the connecting strut width 66 is 0.10 mm. The narrow angle 48 formed by joining strut 30 and expansion strut 28 is 75 degrees, and the narrow angle 94 formed by re-enforcement joining strut 96 and re-enforcement expansion strut 90 is 60 degrees.

Other arrangements of re-enforcement expansion columns 86, such as providing re-enforcement expansion columns 86 only on the ends of the stent, only on one end, or at multiple locations throughout the length of the stent can also be used and fall within the scope of the present invention. A taper can also be programmed into the re-enforced stent 10 by shortening expansion struts 28 and re-enforcement expansion struts 90 in appropriate expansion columns 24 and 86.

Figure 7A:
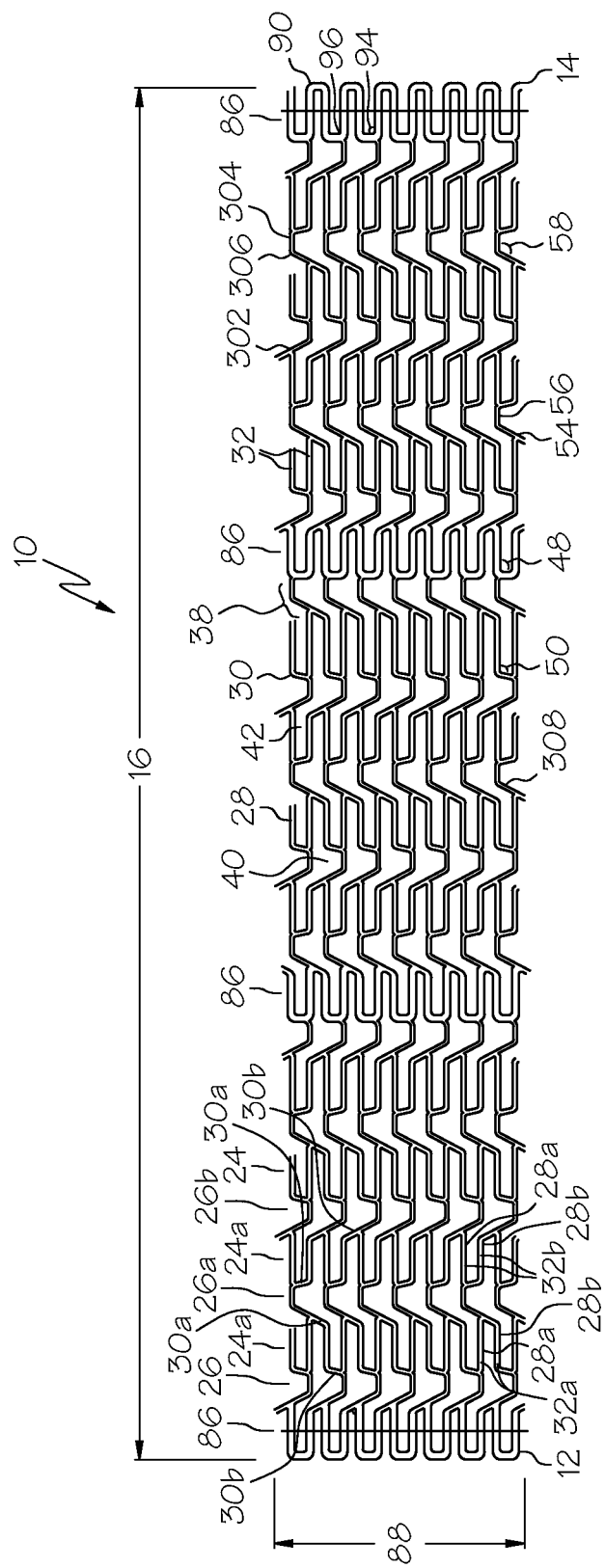
FIG. 7A is a scale drawing of an embodiment of the stent of the present invention including relief notches at strut joints to increase flexibility of the joints.
Figure 7B:
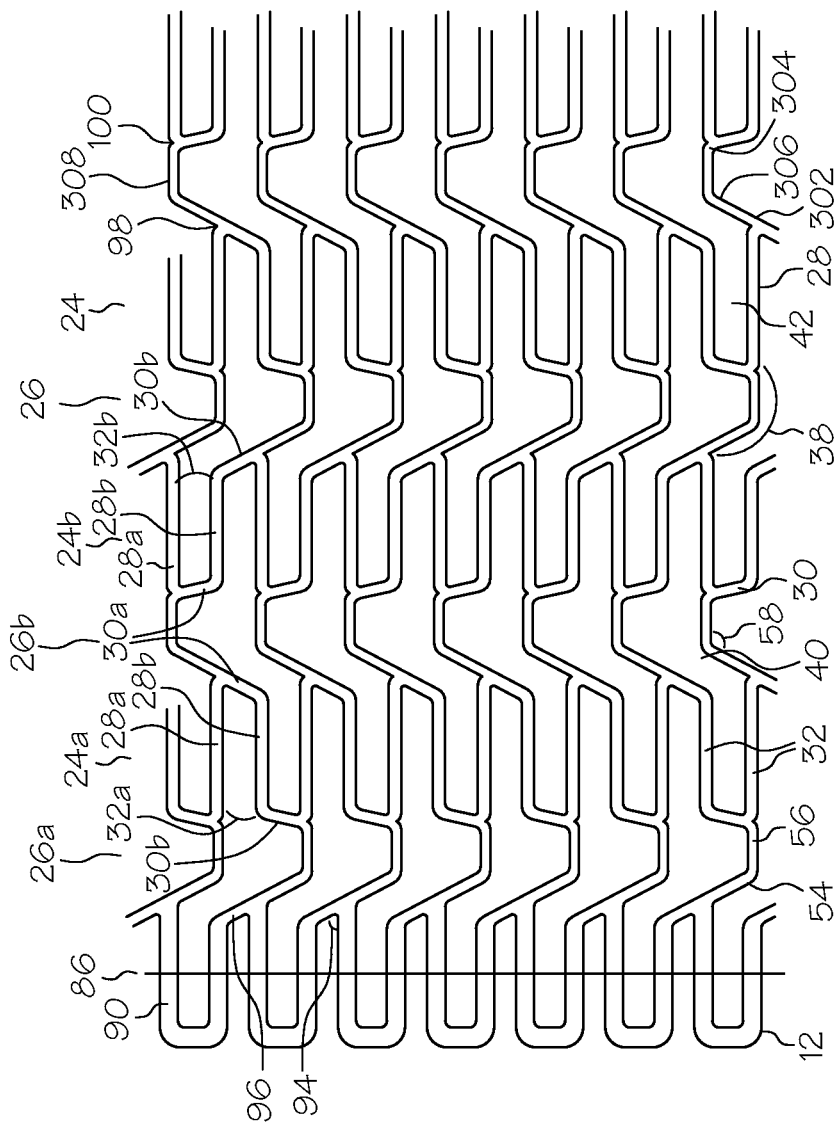
FIG. 7B is an enlarged region of the embodiment of FIG. 7A.
Figure 7C:
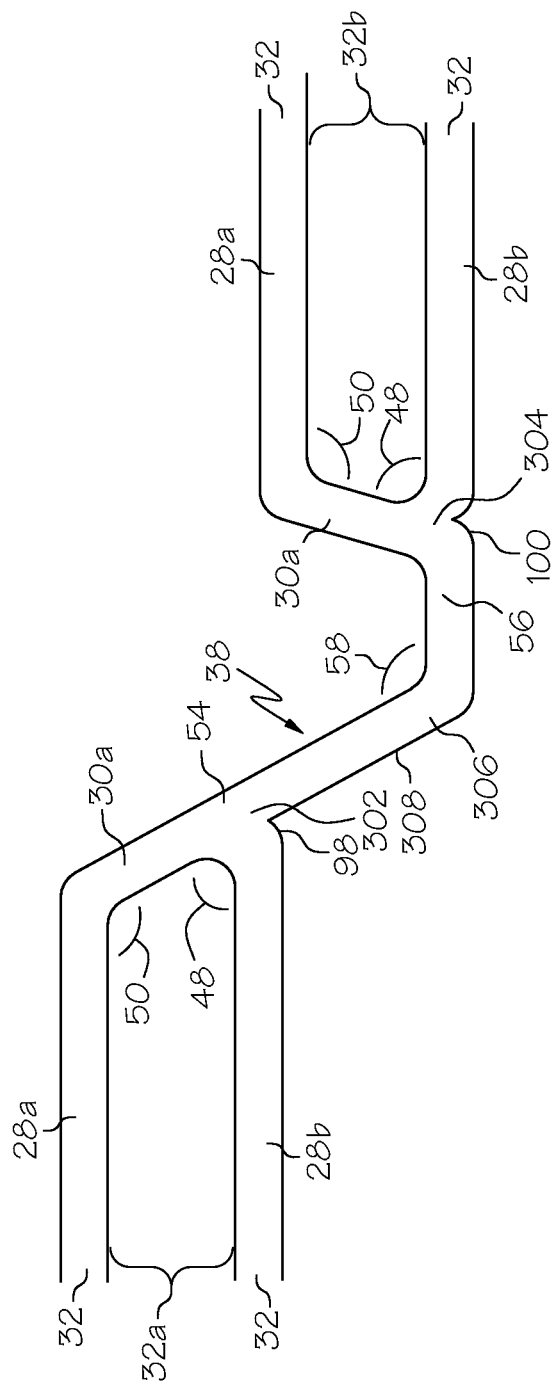
FIG. 7C is an enlarged view of a single connecting strut joining two expansion strut pairs in accordance with the embodiment of FIG. 7A.

Yet another embodiment of the present invention, shown in the FIGS. 7A, 7B and 7C, is similar to the embodiment shown in FIGS. 6A and 6B but has the added feature of relief notches 98 and 100. A relief notch is a notch where metal has been removed from a strut, usually at a joint where multiple struts are connected. Relief notches increase flexibility of a strut or joint by creating a thinned, narrow region along the strut or joint. Relief notch 98 is formed at the joint formed between first linear section 54 of connecting strut 38 and expansion strut 28. Relief notch 100 is formed at the joint between second linear section 56 of connecting strut 38 and expansion strut 28. The positioning of the relief notches gives added flexibility to the unexpanded stent and prevents warping at the joints when the stent is expanded. This results in a smooth surface modulation to the expanded stent frame. Relief notches can be placed at other joints and can be included in any of the previously mentioned embodiments.

FIGS. 8A and 8B show a side elevation view of a variation of an embodiment of the stent of the present invention. In this embodiment a four piece slanted connecting strut 38 is used to couple the corner of an expansion strut pair 32 in one expansion column 24 to the joining strut 30 of a circumferentially offset expansion strut pair 32 in an adjacent expansion column 24. The expansion struts 28, joining struts 30, expansion columns 24, re-enforcement expansion struts 90, re-enforcement joining struts 96, and re-enforcement expansion columns 86 are substantially similar to the fourth embodiment of FIG. 6A. Connecting struts 38 in connecting strut columns 26, however, have an altered geometry and connectivity, described in more detail below.

FIG. 8A shows only the stent struts on the front half of the stent surface. The stent struts on the rear half of the stent surface are not shown. The stent appears as it would if the stent struts and space there between were opaque. FIG. 8B shows all stent struts from both the front and rear halves. The stent appears as it would if the stent struts and the space there between were transparent.

Figure 8C:
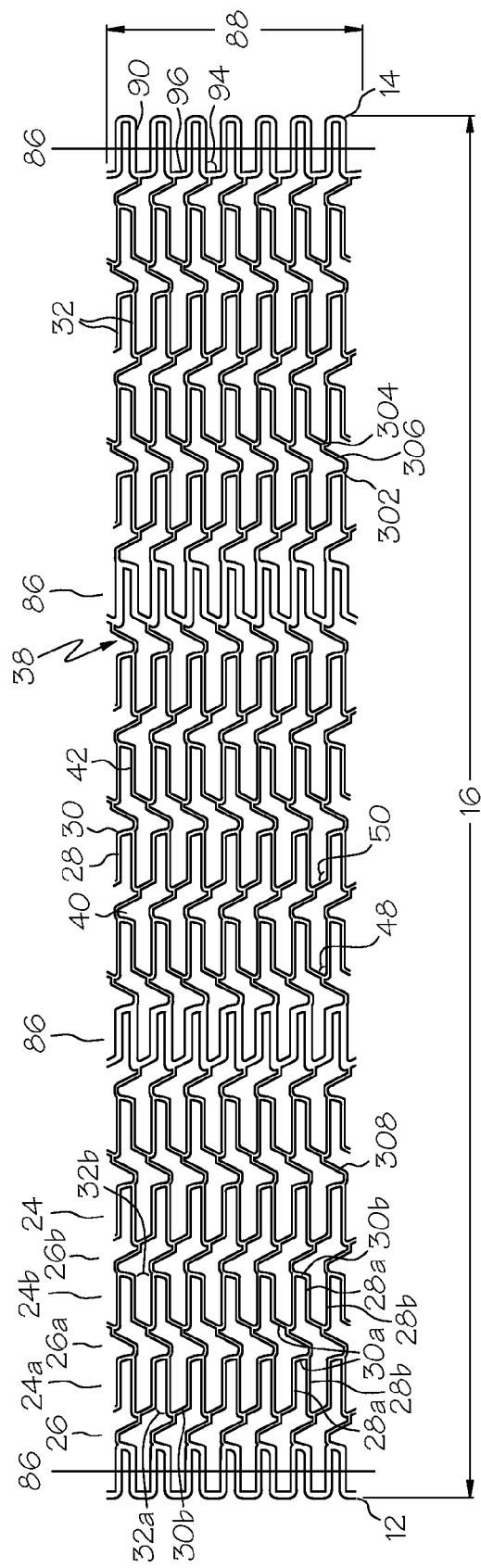
FIG. 8C is a scale drawing of an embodiment of the stent of the present invention.

Another variation of the embodiment shown in FIGS. 8A and 8B is depicted in FIG. 8C wherein the stent 10 is provided with twelve expansion columns 24, four re-enforcement expansion columns 86, and fifteen connecting strut columns 26. In this variation, the stent 10 has a length 16 of 31.96 mm, and an unexpanded circumference 88 of 5.26 mm.

Figure 8D:
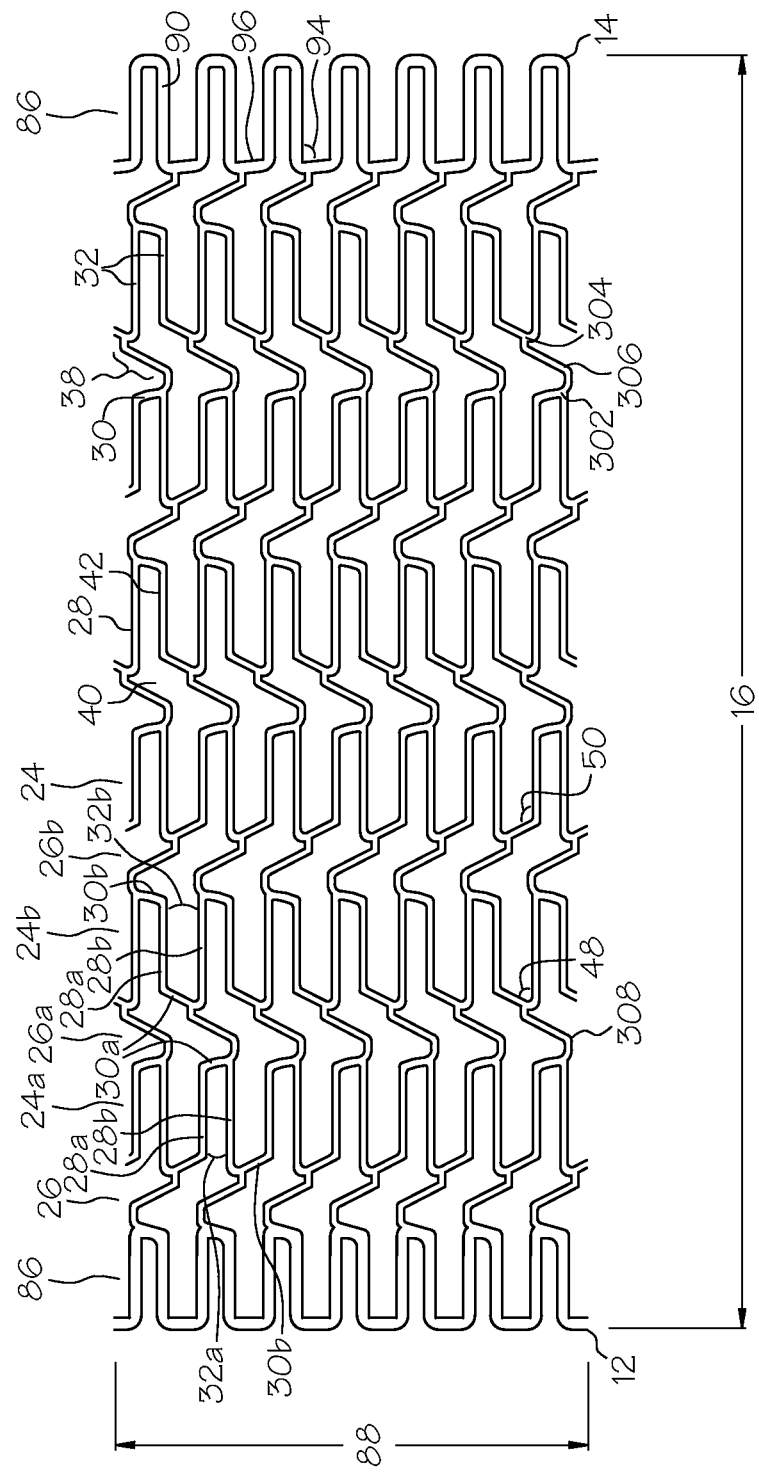
FIG. 8D is a variation of the embodiment of the stent of FIG. 8C.
Figure 8E:
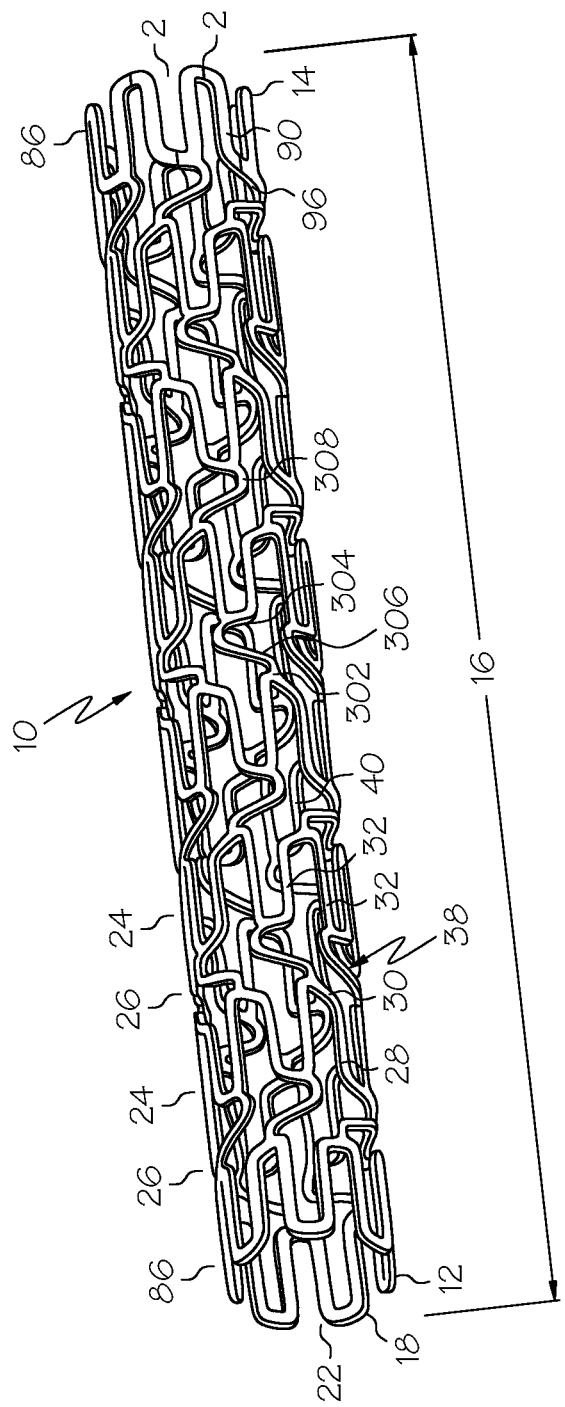
FIG. 8E is a perspective view of the embodiment of FIG. 8D.
Figure 8F:
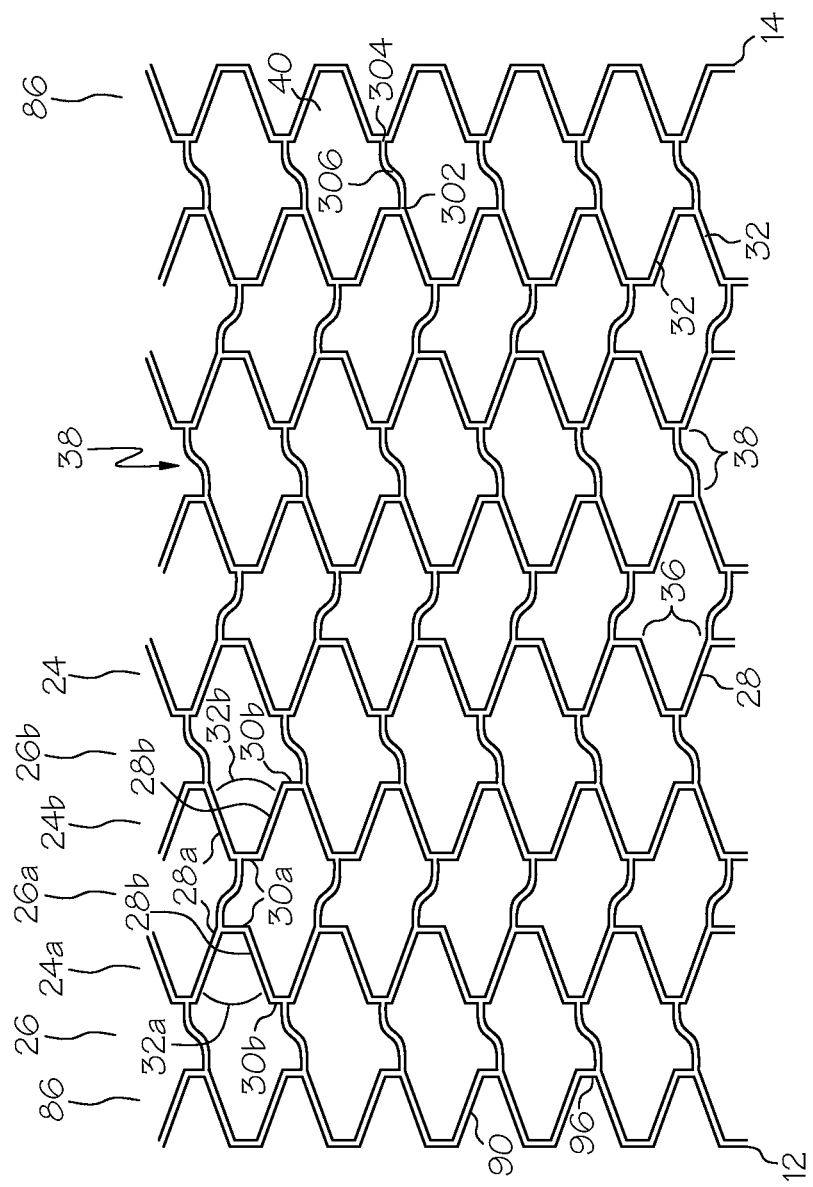
FIG. 8F is a drawing illustrating the post-expansion mode of the stent of the embodiment of FIG. 8D of the present invention.
Figure 8G:
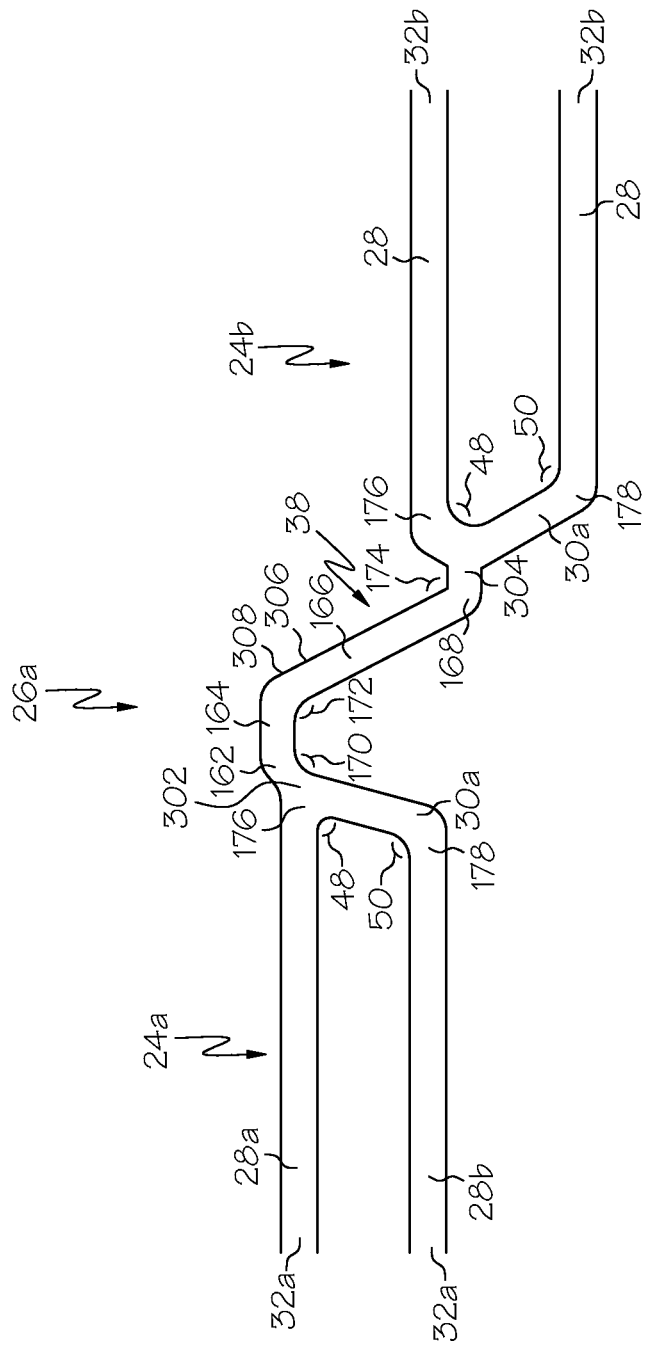
FIG. 8G is an enlarged view of a single connecting strut joining two expansion strut pairs in accordance with an embodiment of the present invention.

Connecting struts 38 shown in an enlarged view in FIG. 8G are made up of four linear sections, a proximal end section 162, first and second intermediate sections 164 and 166 respectively and a distal end section 168 forming three slant angles 170, 172 and 174. The proximal end of proximal section 162 is attached to a corner 176 of an expansion strut pair 32 of an expansion column 24. Corner 176 is formed where joining strut 30 makes narrow angle 48 with expansion strut 28. A second corner 178 of expansion strut 32 is formed where joining strut 30 makes wide angle 50 with expansion strut 28. Corners 176 and 178 can have an angular shape formed by joining linear expansion struts 28 and joining struts 30, or preferably corners 176 and 178 are rounded to remove sharp edges and provide increased flexibility. Additionally rounded corners provide stent 10 with greater expandability and reduce stress in the stent strut material at the corners in the expanded stent.

Proximal end section 162 of connecting strut 38 extends from corner 176 and is attached at its distal end to first intermediate section 164 forming slant angle 170. First intermediate section 164 extends from proximal end section 162 such that first intermediate section 164 is parallel to expansion struts 28 and is connected at its distal end to the proximal end of second intermediate section 166 forming slant angle 172.

Second intermediate section 166 extends in a slanted orientation relative to the longitudinal axis of stent 10, extending both longitudinally along and circumferentially about stent 10. Preferably, second intermediate section 166 is parallel to joining strut 30 of the circumferentially offset expansion strut pair 32 in adjacent expansion column 24.

Second intermediate section 166 attaches at its distal end to the proximal end of distal end section 168 forming slant angle 174. Distal end section 168 extends from second intermediate section 166 attaching at its distal end to joining strut 30 of circumferentially offset expansion strut pair 32 of adjacent expansion column 24. The attachment is at a point intermediate corners 176 and 178, where joining strut 30 forms narrow angle 48 and wide angle 50 respectively with expansion struts 28.

The connection point of distal end section 168 to joining strut 30 is closer to corner 176 than corner 178. Preferably the connection point is one to two or more expansion strut widths from corner 176. Offsetting the connection point of distal end section 168 to joining strut 30 from corner 176 to a point intermediate corner 176 and corner 178 reduces warping of the expanded stent 10, resulting in a smooth surface modulation and reduced risk of thrombosis. Additionally, this design provides a longer total straightened length of connecting strut 38, which further reduces foreshortening of stent 10 during expansion.

Another variation of the stent described above is shown in an unexpanded form in FIGS. 8D, 8E and in an expanded form in FIG. 8F comprises a stent 10 with six expansion columns 24, two re-enforcement expansion columns 86, and seven connecting strut columns 26. In this variation, the stent 10 has a length 16 of 15.04 mm, and an unexpanded circumference 88 of 5.26 mm. The stent design 10 is substantially similar to the design of the embodiment of FIG. 8C with a reduced number of expansion columns, re-enforcement expansion columns, and connecting strut columns.

FIG. 8F illustrates a portion of the expanded stent 10. After expansion of stent 10 by balloon or other means, the expansion struts 28 are spread apart circumferentially, increasing the separation at the open end 36 of expansion strut pairs 32 resulting in an increase in the circumference of the stent 10. The spreading of the expansion struts 28 causes a longitudinal shortening of the expansion columns 24, which is compensated by a straightening of the connecting struts 38. During the expansion process, the slant angles 170, 172 and 174 widen straightening the connecting struts 38, and causing an increase in the separation distance between adjacent expansion columns 24. The asymmetrical interlocking cell geometry of the expanded stent is illustrated in FIG. 8F.

FIGS. 9A, 9B, 9C, 9D, 9E, 9F and 9G illustrate another embodiment of the stent of the present invention. In this embodiment a three piece slanted connecting strut 38 is used to couple the joining strut 30 of an expansion strut pair 32 in one expansion column 24 to the joining strut 30 of a circumferentially offset expansion strut pair 32 in an adjacent expansion column 24. The joints between segments of connecting strut 38 are curved forming a smooth rounded shape. The expansion struts 28, joining struts 30, expansion columns 24, re-enforcement expansion struts 90, re-enforcement joining struts 96, and re-enforcement expansion columns 86 are substantially similar to the fourth embodiment of FIG. 8A. Connecting struts 38 in connecting strut columns 26, however, have an altered geometry and connectivity, described in more detail below.

In the present embodiment shown in FIGS. 9A, 9B and 9C the stent comprises eight expansion columns 24, three re-enforcement expansion columns 86, and ten connecting strut columns 26. In this variation, the stent 10 has a length 16 of 20.32 mm.

Relief notches 204 are utilized at the joints between re-enforcement expansion struts 90 and re-enforcement joining struts 96 in the re-enforcement expansion columns 86 at the stent proximal end 12 and distal end 14. Relief notches 204 reduce the width of the joints between re-enforcement expansion struts 90 and re-enforcement joining struts 96, which reduces stress in the metal at the joints during and after expansion of the stent. Relief notches 204 are particularly important at the stent ends since the stent ends are especially susceptible to warping during and after expansion. In some embodiments relief notches 204 reduce the joint widths, such that the joint widths are substantially the same as the thickness of stent wall 46 (see FIGS. 1B and 1C).

Figure 9D:
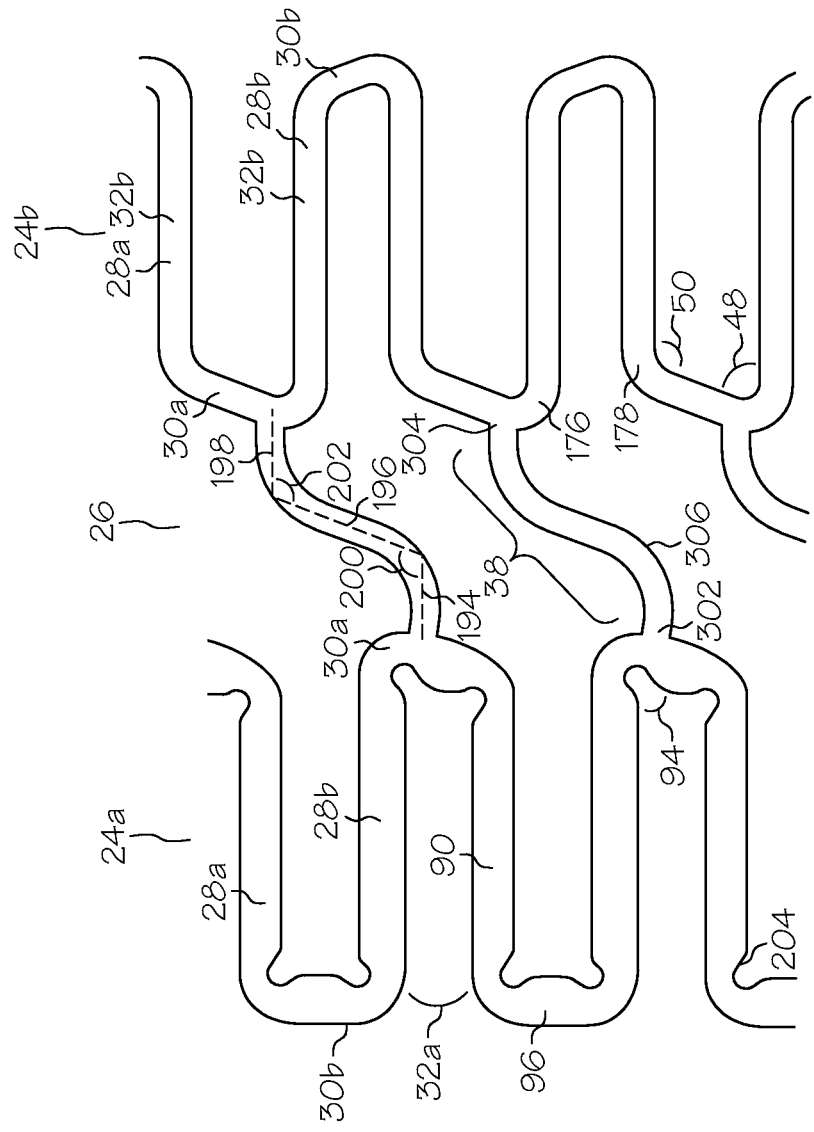
FIG. 9D is an enlarged region of the drawing of FIG. 9C.

Connecting struts 38 shown in an enlarged view in FIG. 9D are made up of three linear sections, a proximal end section 194, an intermediate section 196 and a distal end section 198 forming two slant angles 200, 202. The connecting struts 38 have wide radii of curvature at the joints between connecting strut sections 194, 196 and 198. The shape of connecting strut 38 is thus curved or wavy rather than jagged and angular. The slant angles 200 and 202 are defined by linearly extrapolating proximal end section 194, intermediate section 196 and distal end section 198, as shown by the dotted lines in FIG. 9D.

Figure 9E:
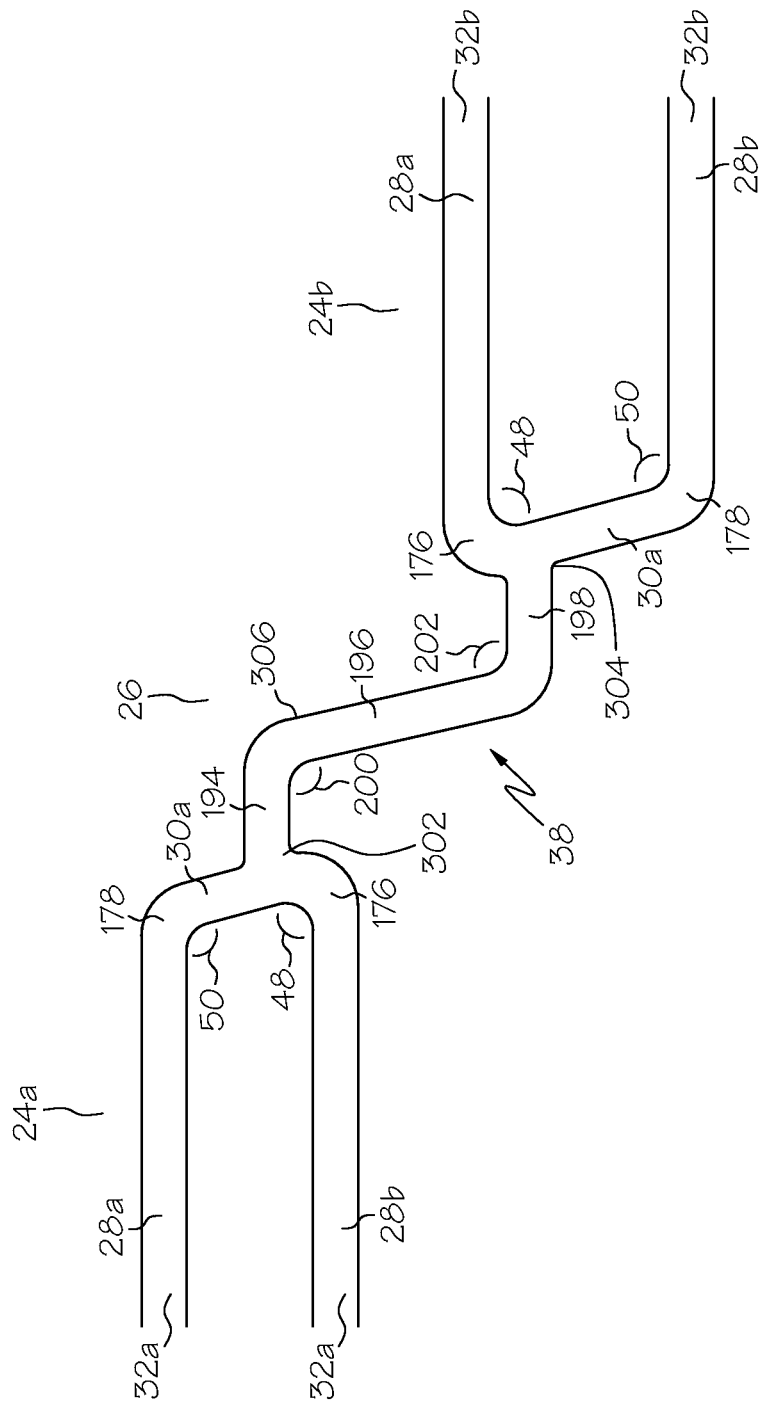
FIG. 9E is a scale drawing of an embodiment of the stent of the present invention.

FIG. 9E shows a variation of the connecting strut design of an embodiment of the invention. The connecting strut 38 of FIG. 9E has smaller radii of curvature at the joints between proximal end section 194, intermediate section 196 and distal end section 198. Connecting strut 38 of FIG. 9E is thus more jagged and angular than that of FIG. 9D.

Referring to the connecting struts 38 of FIGS. 9D and 9E, the proximal end of proximal section 194 is attached to joining strut 30 of expansion strut pair 32 intermediate corners 176 and 178. Proximal end section 194 of connecting strut 38 extends from joining strut 30 and is attached at its distal end to intermediate section 196 forming slant angle 200. Intermediate section 196 extends from proximal end section 194 in a slanted orientation relative to the longitudinal axis of stent 10, extending both longitudinally along and circumferentially about stent 10. Intermediate section 196 is preferably parallel to joining struts 30 of coupled expansion strut pairs 32.

Intermediate section 196 is connected at its distal end to the proximal end of distal end section 198 forming slant angle 202. Distal end section 198 extends from second intermediate section 196 attaching at its distal end to joining strut 30 of circumferentially offset expansion strut pair 32 of adjacent expansion column 24. The attachment is at a point intermediate corners 176 and 178, where joining strut 30 forms narrow angle 48 and wide angle 50 respectively with expansion struts 28.

The connection point of proximal end section 194 and distal end section 198 to joining struts 30 is closer to corner 176 than corner 178. Preferably the connection point is one to two or more expansion strut widths from corner 176. Offsetting the connection point of distal end section 198 to joining strut 30 from corner 176 to a point intermediate corner 176 and corner 178 reduces warping of the expanded stent 10, resulting in a smooth surface modulation and reduced risk of thrombosis. Additionally, this design provides a longer total straightened length of connecting strut 38, which further reduces foreshortening of stent 10 during expansion.

The connecting strut 38 of at least one embodiment has one hundred and eighty degree rotational symmetry about its center. The symmetry of the connecting strut 38 does not, however, result in a symmetrical cell space as the width of loop slots 42 connected in each cell space are different. Adjacent loop slots 42 in each expansion column have alternating narrow and wide widths, preserving the asymmetry of the cell spaces. Introduction of one or many symmetrical cell spaces can be achieved in this design e.g. by providing uniform loop slot width to loop slots in adjacent expansion columns 24 contained in the same cell space. Additionally completely non-uniform cell space patterns utilizing symmetric or asymmetric cell spaces can be achieved e.g. by providing non-uniform variations in the widths of loop slots 42.

Figure 9F:
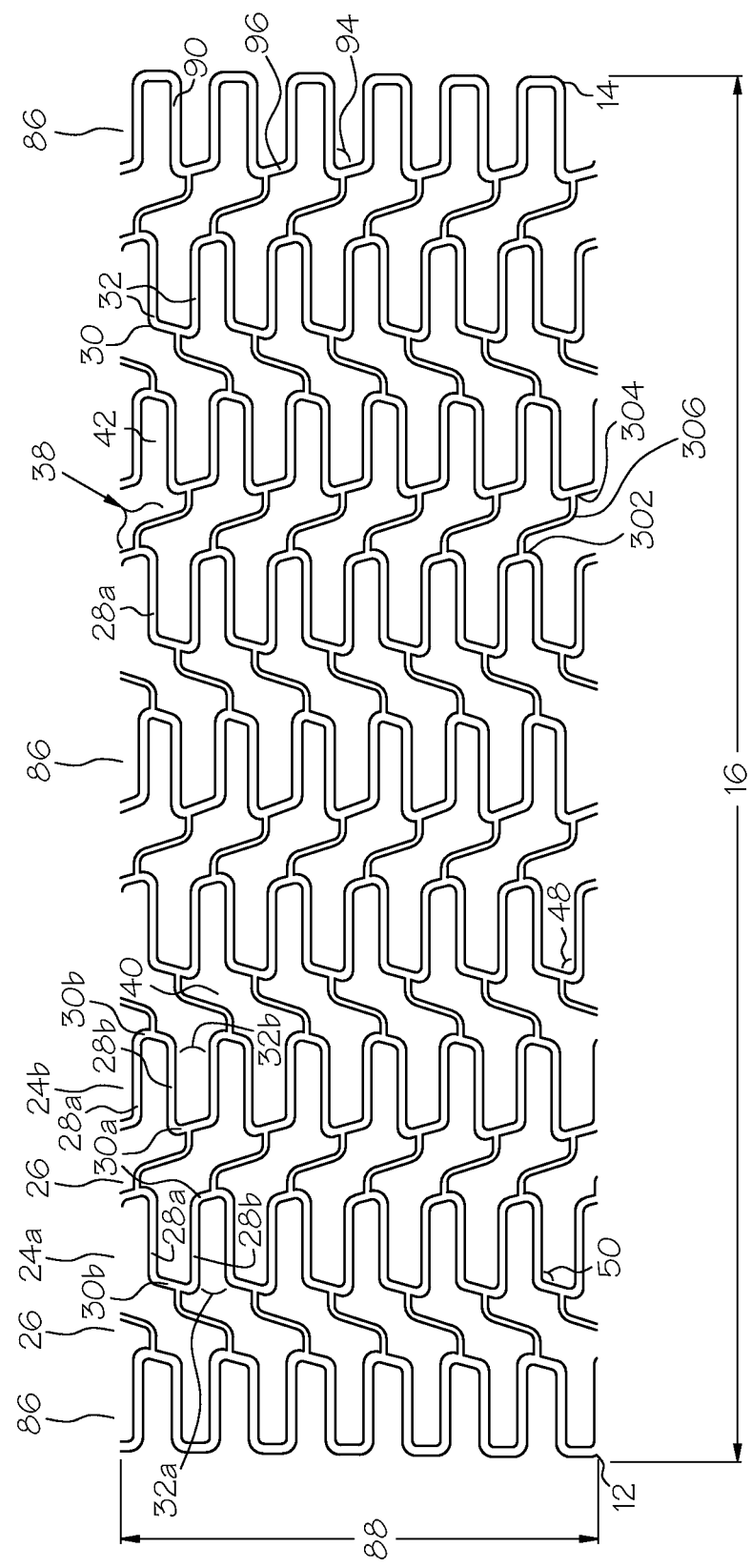
FIG. 9F is a scale drawing of an embodiment of the stent of the present invention.

In another embodiment shown in FIG. 9F, the stent 10 is shown in an unexpanded form and comprises six expansion columns 24, three re-enforcement expansion columns 86, and eight connecting strut columns 26. In this variation, the stent 10 has a length 16 of 16.00 mm, and an unexpanded circumference 88 of 5.26 mm. The stent design 10 is substantially similar to the design of the embodiment of FIGS. 9A, 9B and 9C with a reduced number of expansion columns 24 and connecting strut columns 26.

Figure 9G:
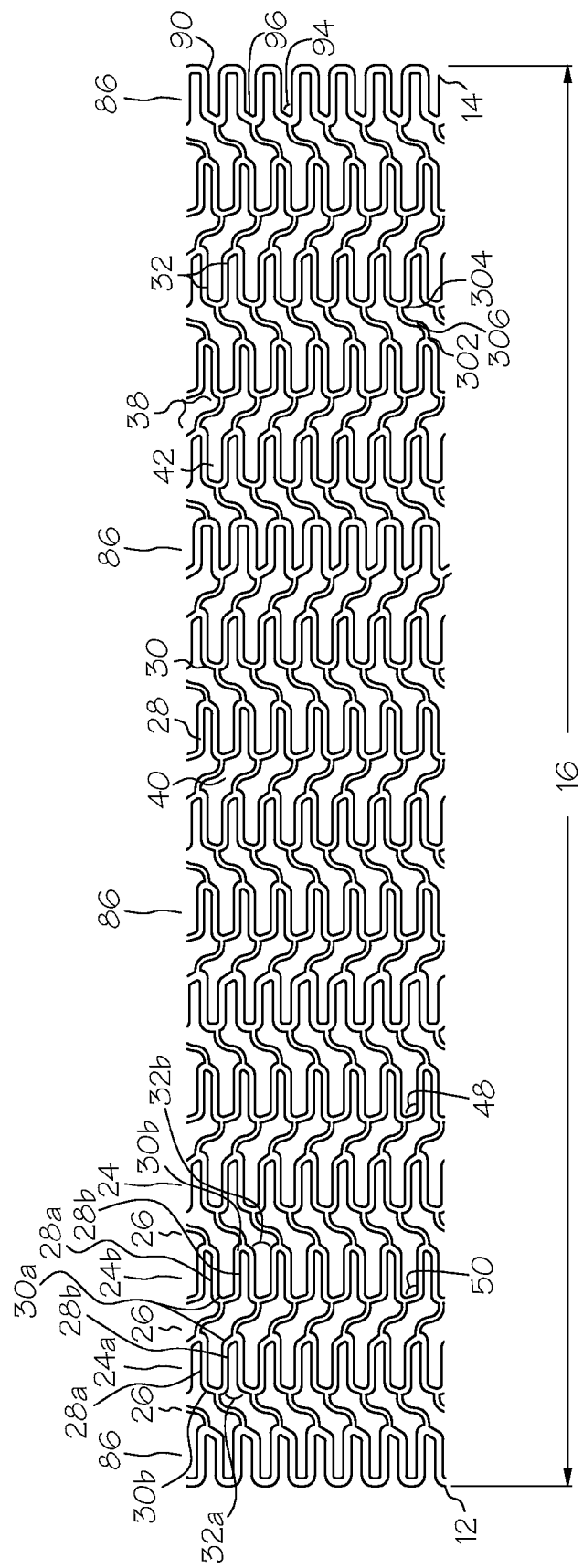
FIG. 9G is an enlarged view of a single connecting strut joining two expansion strut pairs in accordance with an embodiment of the present invention.

In the embodiment shown in FIG. 9G comprises a stent 10 with twelve expansion columns 24, four re-enforcement expansion columns 86, and fifteen connecting strut columns 26. In this variation, the stent 10 has a length 16 of 30.01 mm, and an unexpanded circumference 88 of 5.26 mm. The stent design 10 is substantially similar to the design of the embodiment of FIGS. 9A, 9B and 9C with an increased number of expansion columns 24 re-enforcement expansion columns 86 and connecting strut columns 26.

Figure 10F:
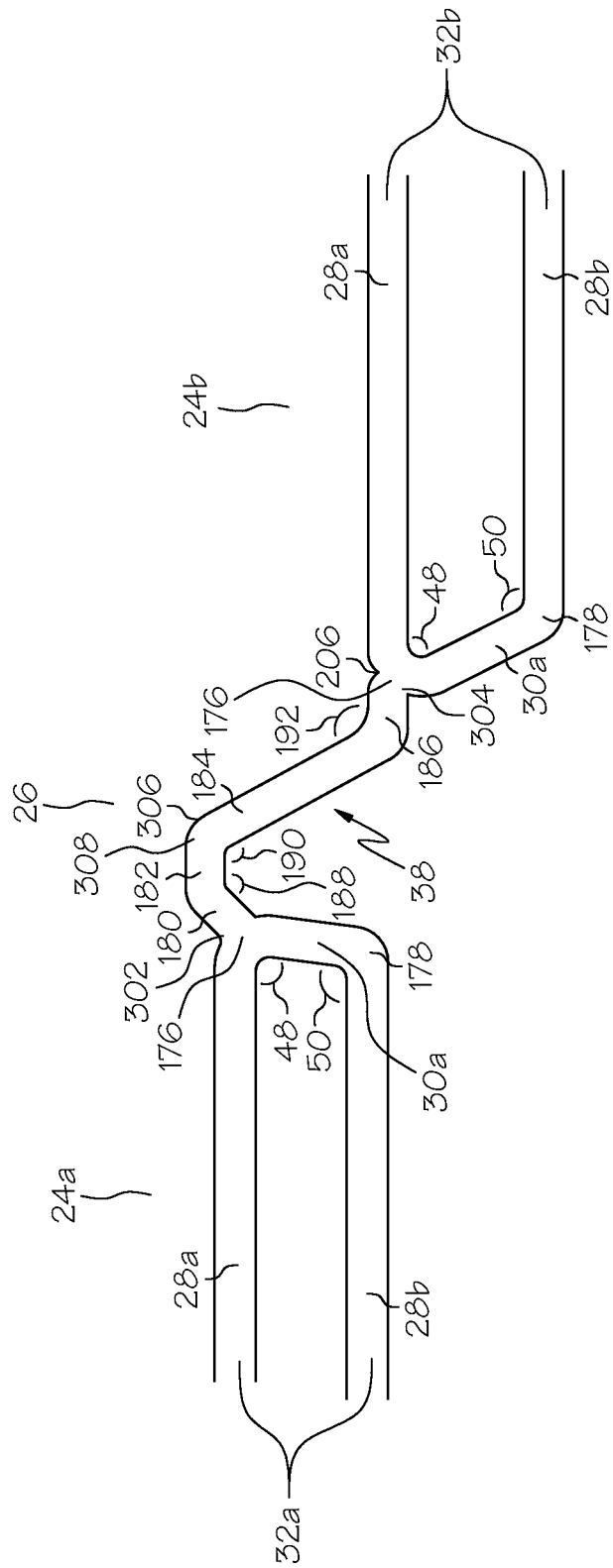
FIG. 10F is a drawing of an alternate geometry of connecting struts and joining struts in accord with the present invention.

FIGS. 10A, 10B, 10C, 10D, 10E and 10F illustrate some examples of alternate connecting strut designs which can be used in any of the previously discussed embodiments. FIG. 10A shows a rounded loop connecting strut 38 which joins two circumferentially offset expansion strut pairs 32 in adjacent expansion columns. Expansion struts 28 in each expansion strut pair 32 are joined by adjoining strut 30. Joining struts 30 are slanted such as to form a narrow angle 48 and a wide angle 50 with the expansion struts 28 they connect. The rounded loop connecting strut 38 connects expansion struts 28 at the point where narrow angle 48 is formed between expansion struts 28 and joining struts 30. The slopes of the rounded connecting strut 38 at its proximal end 102 and distal end 104 substantially match the slopes of the joining struts 30 connecting the pairs of expansion struts 28. The rounded loop connecting strut 38 thus blends smoothly into the joining struts 30. Additionally the rounded loop connecting strut 38 has a first radius of curvature 106 and a second radius of curvature 108.

In the embodiment shown in FIG. 10B a rounded loop connecting strut 38 joins two circumferentially offset expansion strut pairs 32 in adjacent expansion columns. Expansion struts 28 in each expansion strut pair 32 are joined by a joining strut 30. Joining struts 30 are at right angles to the expansion struts 28 they connect. The rounded loop connecting strut 38 connects to expansion struts 28 at the same point as joining struts 30. The rounded connecting strut 38 has a first radius of curvature 106 and a second radius of curvature 108 such that it connects circumferentially offset expansion strut pairs 32.

In the embodiment of FIG. 10C connecting strut 38 joins two circumferentially offset expansion strut pairs 32 in adjacent expansion columns. Expansion struts 28 in each expansion strut pair 32 are joined by adjoining strut 30. Joining struts 30 are slanted such as to form a narrow angle 48 and a wide angle 50 with the expansion struts 28 they connect. The connecting strut 38 connects expansion struts 28 at the point where narrow angle 48 is formed between expansion strut 28 and joining strut 30.

The connecting strut 38 is made up of three linear sections 110, 112, and 114 forming two slant angles 116 and 118. The proximal end of section 110 is attached to expansion strut 28 at the point where joining strut 30 forms narrow angle 48 with expansion strut 28. Section 110 extends substantially collinear to joining strut 30 and is attached at its distal end to intermediate section 112 forming slant angle 116.

Intermediate section 112 extends at an angle to section 110 such that intermediate section 112 is substantially parallel to expansion struts 28 and is connected at its distal end to the proximal end of distal section 114 forming slant angle 118. Distal section 114 extends at an angle such that it is substantially collinear to joining strut 30 of the adjacent expansion strut pair 32. Distal section 114 attaches at its distal end to expansion strut 28 of the adjacent expansion strut pair 32, at the point where joining strut 30 forms narrow angle 48 with expansion strut 28.

In the embodiment of FIGS. 10D and 10E a connecting strut 38 joins two circumferentially offset expansion strut pairs 32 in adjacent expansion columns. Expansion struts 28 in each expansion strut pair 32 are joined by a joining strut 30. Joining struts 30 are at right angles to the expansion struts 28 they connect. The connecting strut 38 connects to expansion struts 28 at the same point as joining struts 30.

The connecting struts 38 of FIGS. 10D and 10E are made up of multiple connecting strut sections connected end to end to form a jagged connecting strut 38 with multiple slant angles, coupling expansion strut pair 32 to adjacent expansion strut pair 32. The connecting strut of FIG. 10D is made up of three connecting strut sections, a proximal section 120, an intermediate section 122 and a distal section 124 defining two slant angles 126 and 128, while the connecting strut of FIG. 10E comprises of four connecting strut sections, a proximal section 130, intermediate sections 132 and 134, and a distal section 136 defining three slant angles 138, 140 and 142. In addition, connecting strut section 134 can be modified by replacing connecting strut section 136 by the dotted connecting strut section 144 to give another possible geometry of connecting struts 38.

In the embodiment of FIG. 10F connecting strut 38 joins two circumferentially offset expansion strut pairs 32 in adjacent expansion columns. Expansion struts 28 in each expansion strut pair 32 are joined by a joining strut 30. Joining struts 30 are slanted such as to form a narrow angle 48 and a wide angle 50 with the expansion struts 28 they connect.

Connecting strut 38 is made up of four linear sections, a proximal end section 180, first and second intermediate sections 182 and 184 respectively and a distal end section 186 forming three slant angles 188, 190 and 192. The proximal end of section 180 is attached to corner 176 at the point where joining strut 30 forms narrow angle 48 with expansion strut 28. Proximal end section 180 extends at an angle to joining strut 30 and is attached at its distal end to first intermediate section 182 forming slant angle 188. First intermediate section 182 extends at an angle to proximal end section 180 such that first intermediate section 182 is substantially parallel to expansion struts 28 and is connected at its distal end to the proximal end of second intermediate section 184 forming slant angle 190. Second intermediate section 184 is substantially longer than the first intermediate section 182. Second intermediate section 184 extends at an angle such that it is substantially collinear to joining strut 30 of the adjacent expansion strut pair 32. Second intermediate section 184 attaches at its distal end to the proximal end of distal end section 186 forming slant angle 192. Distal end section 186 extends in a slightly sloping orientation relative to expansion struts 28, attaching to corner 176 of expansion strut pair 32 where joining strut 30 forms narrow angle 48 with expansion strut 28. Relief notches 206 are formed at the joint between distal end segment 186 of connecting strut 38 and corner 176 of expansion strut pair 32 to increase flexibility of the unexpanded stent and prevent warping when the stent is expanded.

One skilled in the art will recognize that there are many possible arrangements of connecting struts and joining struts consistent with the present invention; the above examples are not intended to be an exhaustive list. In particular, it is noted that (a) connecting strut sections need not be linear but may contain one or many radii of curvature, (b) connecting strut sections may each have a different longitudinal axis, (c) the joint between connecting strut sections need not be jagged or sharp, but rather can be smooth containing one or multiple radii of curvature, and (d) relief notches may be present at any of the strut joints.

The stent of the present invention is ideally suited for application in coronary vessels although versatility in the stent design allows for applications in non-coronary vessels, the aorta, and nonvascular tubular body organs.

Typical coronary vascular stents have expanded diameters that range from 2.5 to 5.0 mm. However, a stent with high radial strength and fatigue tolerance that expands to a 5.0 mm diameter may have unacceptably high stent metal fraction when used in smaller diameter vessels. If the stent metal fraction is high, the chances of acute thrombosis and restenosis potential will increase. Even with the same metal fraction a smaller caliber vessel is more likely than a larger one to have a high rate of thrombosis. It is, therefore, preferred to have at least two different categories of stents for coronary application, for example, small vessels stents for use in vessels with diameters from 2.5 mm to 3.0 mm, and large vessel stents for use in vessels with diameters from 3.0 mm to 5.0 mm. Thus, both small vessels and large vessels when treated with the appropriate sized stent will contain stents of similar idealized metal fraction.

The stent of the present invention can be made using a CAM-driven laser cutting system to cut the stent pattern from a stainless steel tube. The rough-cut stent is preferably electro-polished to remove surface imperfections and sharp edges. Other methods of fabricating the stent can also be used such as, water/laser-jet, EDM, photo-electric etching technology, or other methods. Any suitable material can be used for the stent including other metals and polymers so long as they provide the essential structural strength, flexibility, biocompatibility and expandability.

In some embodiments at least a portion of the stent is plated or otherwise provided with a radiopaque material such as metals including gold, platinum, tantalum or other suitable metal. It is preferred to provide one or both ends of the stent with a radiopaque material by localized plating or other mechanisms; however, the entire stent or other regions can also be plated or otherwise provided with radiopaque material. When plating both ends, one to three or more expansion columns on each end of the stent are plated to mark the ends of the stent so they can be identified under fluoroscopy during the stenting procedure. By plating the stent only at the ends, interference of the radiopaque plating material with performance characteristics or surface modulation of the stent frame is minimized. Additionally the amount of plating material required is reduced, lowering the material cost of the stent.

In some embodiments one or more expansion struts or other portions of the stent are provided with one or more radiopaque fasteners such as a crimped sleeve of radiopaque material, a rivet of radiopaque material or other device(s).

After plating, the stent is cleaned, typically with detergent, saline and ultrasonic means that are well-known in the art. The stents are then inspected for quality control, assembled with the delivery balloon catheter, and properly packaged, labeled, and sterilized.

Figure 11:
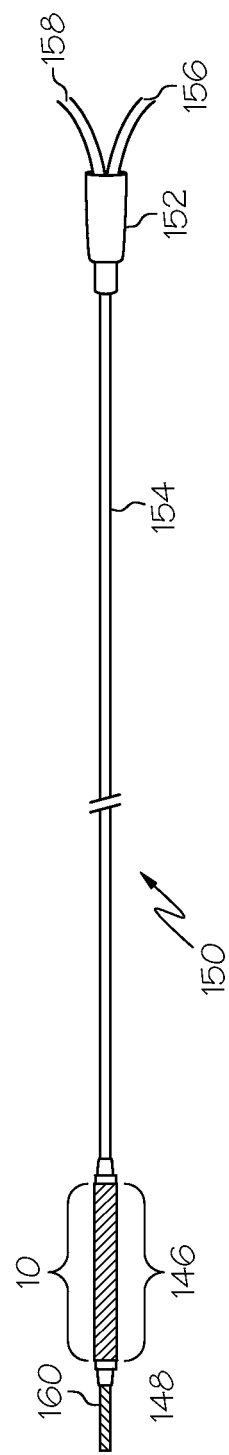
FIG. 11 is a delivery balloon catheter, illustrating a method of deliver of a stent in accord with the present invention.

Stent 10 can be marketed as stand alone or as a pre-mounted delivery balloon catheter assembly as shown in FIG. 11. Referring to FIG. 11, the stent 10 is crimped over a folded balloon 146 at the distal end 148 of a delivery balloon catheter assembly 150. The assembly 150 includes a proximal end adapter 152, a catheter shaft 154, a balloon channel 156, a guidewire channel 158, a balloon 146, and a guidewire 160. Balloon 146 can be tapered, curved, or both tapered and curved from a proximal end to a distal end in the expanded state. Additionally stent 10 can be non-tapered or tapered in the expanded state.

Typically the guidewire 160 is inserted into the vein or artery and advanced to the target site. The catheter shaft 154 is then forwarded over the guidewire 160 to position the stent 10 and balloon 146 into position at the target site. Once in position the balloon 146 is inflated through the balloon channel 156 to expand the stent 10 from a crimped to an expanded state. In the expanded state, the stent 10 provides the desired scaffolding support to the vessel. Once the stent 10 has been expanded, the balloon 146 is deflated and the catheter shaft 154, balloon 146, and guidewire 160 are withdrawn from the patient.

The stent of the present invention can be made as short as less than 10 mm in length or as long as 100 mm or more. If long stents are to be used, however, matching length or preferably slightly longer delivery catheter balloons will typically be needed to expand the stents into their deployed positions. Long stents, depending on the target vessel, may require curved long balloons, tapered long balloons or curved and tapered long balloons for deployment. Curved and/or tapered balloons which match the natural curve and taper of a blood vessel reduce stress on the blood vessel during and after stent deployment. This is especially important in many coronary applications which involve stenting in curved and tapered coronary vessels. The use of such curved and/or tapered balloons is within the scope of the present invention.

In some embodiments of the invention such as those depicted in FIGS. 1A, 2A-8E, 8G, 10A-10F and 12-67, the stent 10 may be characterized as having a first expansion strut column 24a comprised of a plurality of adjacent first expansion strut pairs 32a, each of which in turn have a first expansion strut 28a and a second expansion strut 28b. The first expansion strut column 24a further comprises a plurality of first joining portions or struts 30a. The first expansion strut 28a is in communication with the second expansion strut 28b via the first joining portion 30a. The first expansion strut column 24a also comprises a plurality of second joining portions 30b, each first expansion strut pair 32a is in communication with an adjacent first expansion strut pair 32a via a second joining portion 30b.

Adjacent to the first expansion strut column 24a is a second expansion strut column 24b that is comprised of a plurality of adjacent second expansion strut pairs 32b, wherein each second expansion strut pair comprises a first expansion strut 28a and a second expansion strut 28b. The second expansion strut column further comprises a plurality of first joining portions 30a, wherein the first expansion strut 28a is in communication with the second expansion strut 28b at a first joining portion 30a. The second expansion strut column further comprises a plurality of second joining portions 30b. Each second expansion strut pair 32b is in communication with an adjacent second expansion strut pair 32b via a second joining portion 30b;

Between the first expansion strut column 24a and the second expansion strut column 24b is positioned a first connecting strut column 26a. The first connecting strut column 26a comprises at least one connecting strut 38. The connecting strut 38, comprises a first end region 302, a second end region 304 and an intermediate region 306 therebetween.

The first end region 302 extends from a portion of one of the first expansion strut pairs 32a at a location in closer proximity to the first expansion strut 28a than to the second expansion strut 28b. The second end region 304 extends from a portion of one of the second expansion strut pairs 32b. In some embodiments, such as for example in the embodiment shown in FIG. 34, the second end region 304 is engaged to a portion of the second expansion strut pair 32b at a location substantially equal in proximity to the first expansion strut 28a and the second expansion strut 28b. In other embodiments, such as for example those depicted in FIGS. 12-33 and 35A-67, the second end region 304 is engaged to a portion of the second expansion strut pair 32b at a location in closer proximity to the first expansion strut 28a than to the second expansion strut 28b.

At least one of the connecting struts comprise a wrap portion 308. The wrap portion 308 is at least partially wrapped about at least one first joining portions 30a of either or both the first expansion strut column 24a and the second expansion strut column 24b. The wrap portion 308 of the connector 38 may comprise one or more portions of the connector or alternatively the entire connector 38 may be characterize as a wrap portion 308 or one or more interconnected wrap portions 308.

Figure 12:
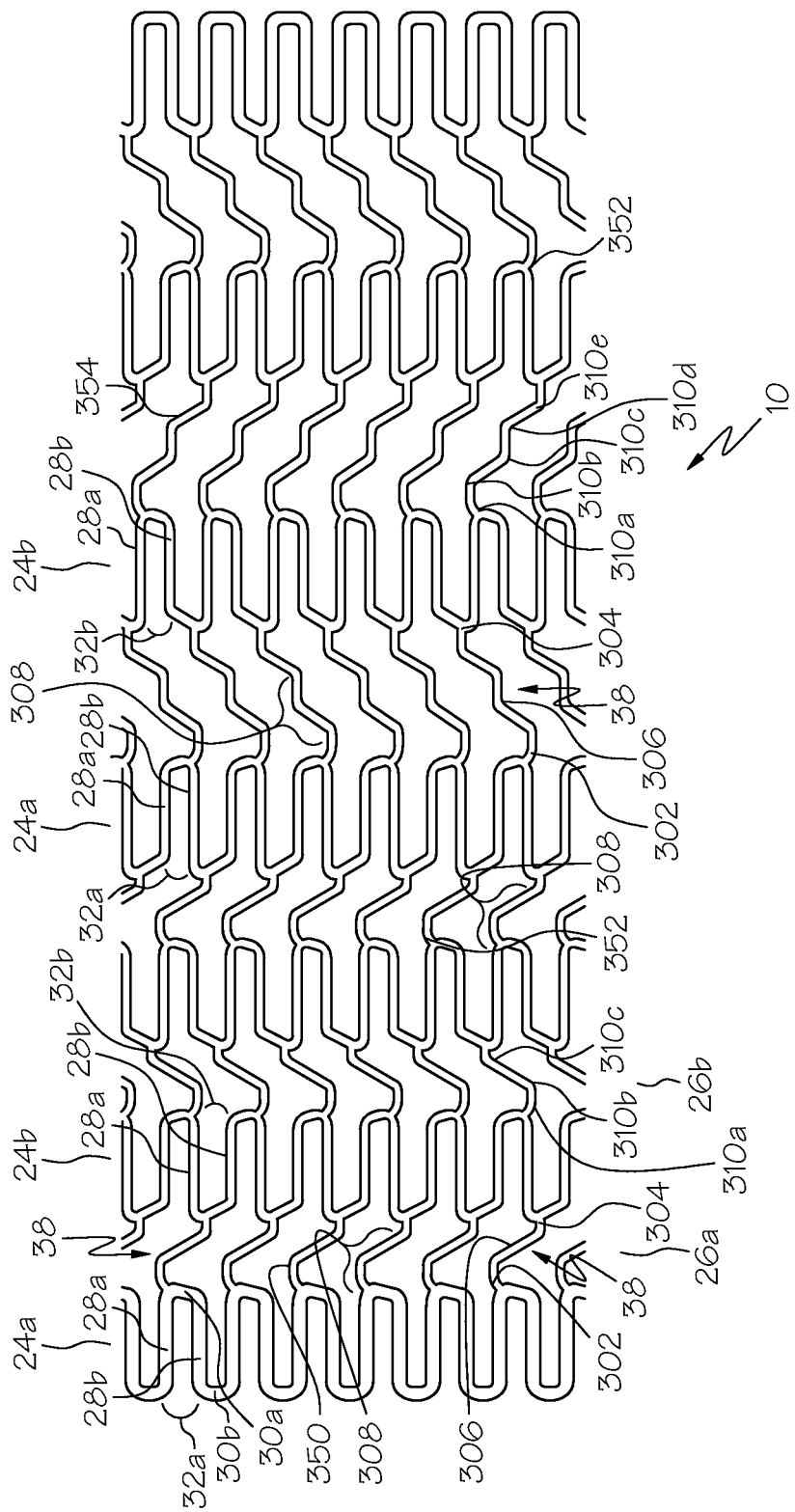
FIG. 12 is a partial side view of an embodiment of the invention.

In the embodiments shown in FIGS. 12-67 the intermediate region 306 further comprises at least two bend portions 310a and 310b.

In some embodiments, such as those illustrated in FIGS. 16-18 and 21-67 the connecting struts 38 each have a connecting strut width 66. The wrap portion 308 of one or more of the connecting struts 38 and at least one first joining portion of either or both of the first expansion strut column 24a and the second expansion strut column 24b define a slot region 320, wherein the slot region 320 defines a slot region width 322, the slot region width 322 being no greater than the connecting strut width 66. In some embodiments the slot region width 22 is the point at which the connecting strut 38 and the first or second joining portion 30a or 30b respectively are at their closest proximity but not touching.

In some embodiments such as are depicted in FIGS. 34-65 the wrap portion 308 of at least one of the connecting struts 38 is characterized as an extension 314 of one or both of the first expansion strut 28a and the second expansion strut 28b of either or both the first expansion strut column 24a and the second expansion strut column 24b. At least a portion of the extension 314 runs parallel to at least a portion of the first joining portion 30a of at least one of the first expansion strut column 24a and second expansion strut column 24b.

In various embodiments of the invention depicted in FIGS. 12-67 the stent 10 is provided with expansion strut columns 24 that may be characterized as substantially serpentine bands wherein the first expansion strut column 24a is a first substantially serpentine band and the second expansion strut column is a second substantially serpentine band. The first substantially serpentine band 24a and the second substantially serpentine band 24b are connected by at least one connecting member 38. The at least one connecting member has a connecting member width 66. The first substantially serpentine band 24a has a plurality of first end portions 30a and a plurality of second end portions 30b. The second substantially serpentine band 24b has a plurality of first end portions 30a and a plurality of second end portions 30b. The at least one connection member 38 and at least one first end portion 30a of at least one of the first substantially serpentine band 24a and the second serpentine band 24b forming a slot region 320, the slot region having a slot region width 322, the slot region width 322 is no greater than the connection member width 66.

In some embodiments the at least one connection member 38 comprises the at least one wrap portion 308. The at least one wrap portion extends away from at least one of the plurality first end portions 326 and wraps around at least a portion of the first end portion 326 from which it extends.

In some embodiments, such as for example those depicted in FIGS. 12, 22, 35, 36, 57, 58, 64 and 65, the stent 10 is provided with at least two distinctly different configurations of connecting struts or members 38. Connectors 38 of different configurations may be utilized in the same connecting strut column or different connecting strut columns 26a and 26b respectively, as is shown. Connectors 38 of different configurations may have different shapes, lengths, components, widths, angular orientations, compositions, etc., from one another.

A first connector configuration 350 of FIG. 12 has an intermediate region 306 having three bend portions indicated at: 310a, 310b, and 310c. While the intermediate region 306 of a second connector configuration 354 comprises five bend portions indicated at: 310a, 310b, 310c, 310d and 310e.

In the embodiment of FIG. 12, the various configurations 350 and 354 of connecting struts or connectors 38 includes a wrap portion 308 that extends longitudinally and circumferentially away from the strut pair 32a of the first expansion strut column 24a to engage a strut pair 32b of the second expansion strut column 24b. As is shown, in some embodiments the first end region 302 of the connector 38 is engaged to the strut pair 32a at an intersection 352 of the first expansion strut 28a and a first joining strut or portion 30a, while the second end region 304 of the connector is engaged to the strut pair 32b at a point on a first joining strut 30a of the second expansion strut column. It must be noted however, that different engagement configurations between the strut pairs 32a and 32b and the first end region 302 and the second end region 304, respectively, may be utilized.

Figure 13:
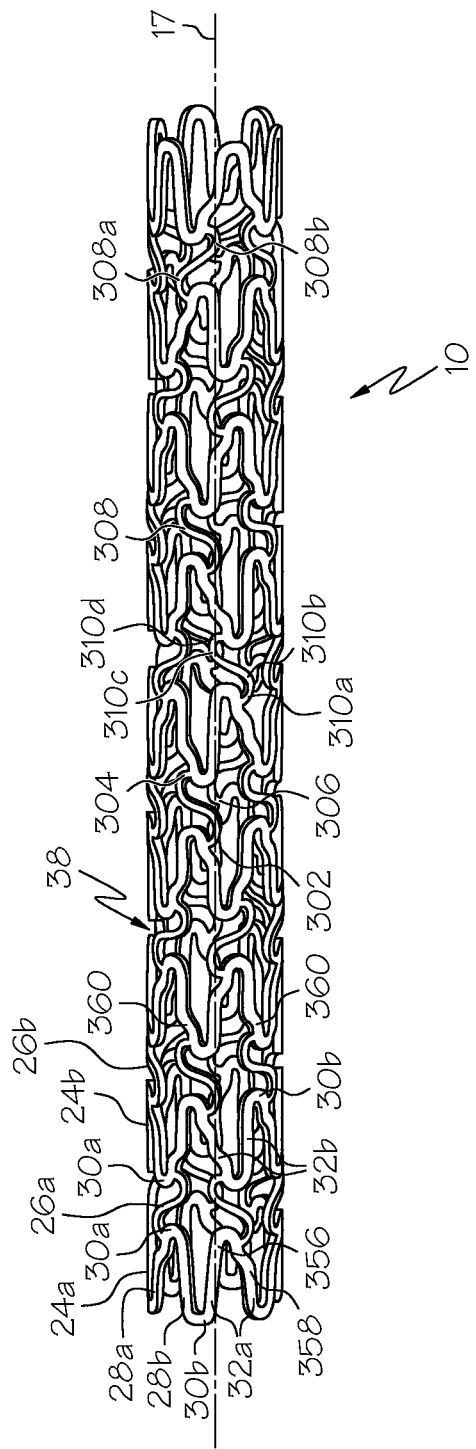
FIG. 13 is a perspective view of an embodiment of the invention.
Figure 14:
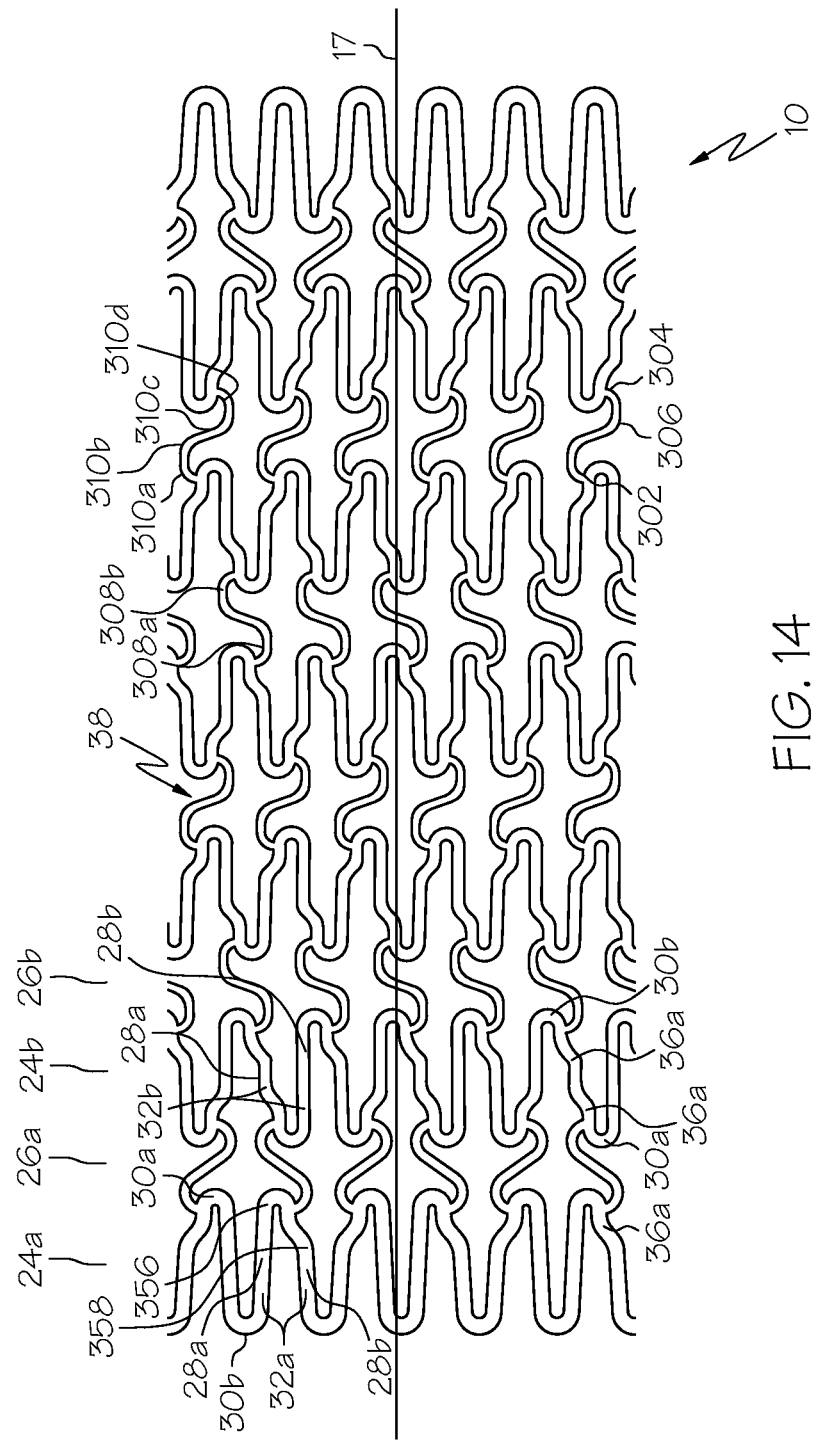
FIG. 14 is a side view of the embodiment shown in FIG. 13.
Figure 15:
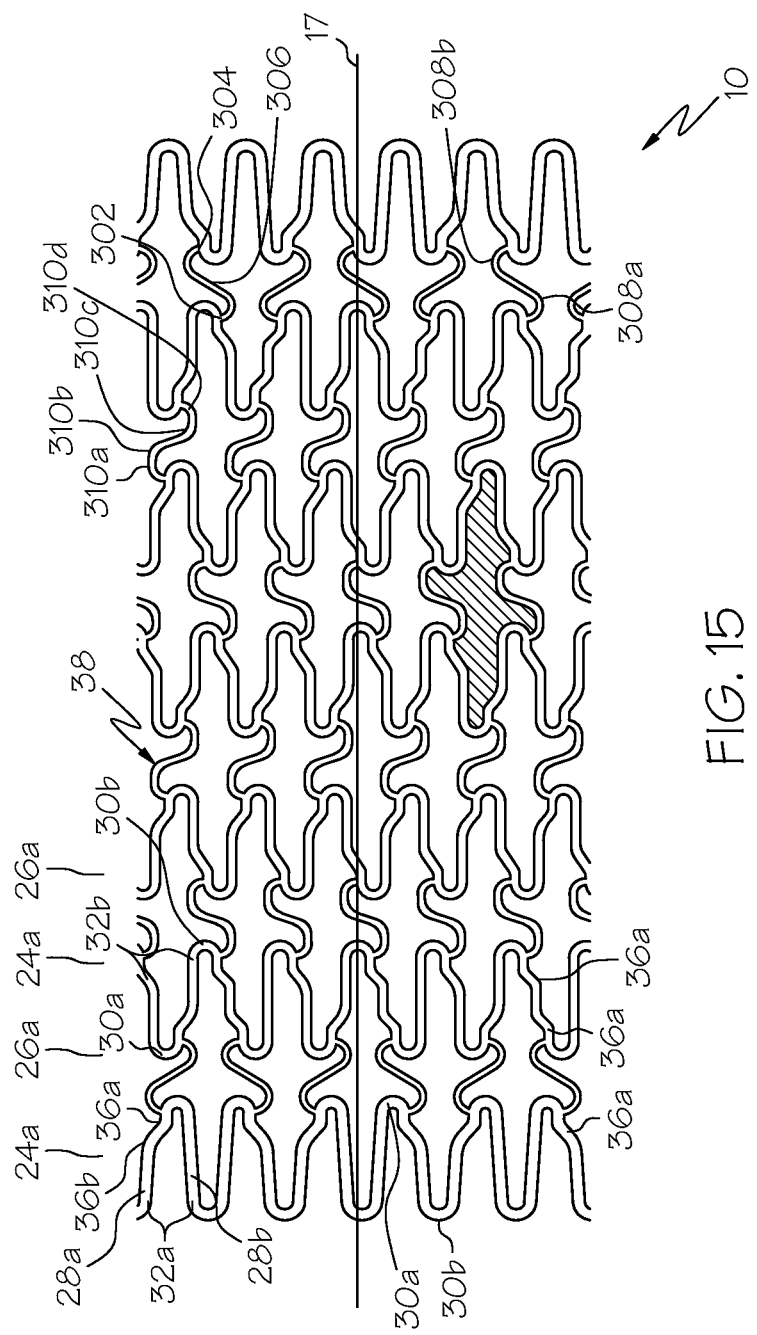
FIG. 15 is a side view of the embodiment shown in FIG. 13.

In the embodiments shown in FIGS. 13-15, the first expansion strut column 24a of the stent 10 is made of a plurality of adjacent first expansion struts 28a and second expansion struts 28b connected by a plurality of first joining struts 30a to form adjacent first strut pairs 32a. A joining strut 30a forms a first intersection 356 where the first joining strut 30a joins a first expansion strut 28a and a second intersection 358 is formed where the first joining strut 30a joins a second expansion strut 28b of the first expansion strut pair 32a.

The first and second expansion struts 28a and 28b in a first expansion strut column 24a are aligned so that at least a portion of the first and second expansion struts 28a and 28b are parallel to each other. However, one or more portions of either or both of the first and second expansion struts 28a and 28b may not be parallel to the longitudinal axis 17 of the stent 10 and/or to the adjacent companion first or second expansion strut 28a and 28b.

In some embodiments, the one or both of the first expansion strut 28a and the second expansion strut 28b of a given expansion strut pair 32a and/or 32b may include a stepped notch 360 on a distal or proximal end of the respective first or second expansion strut 28a and/or 28b. At least a portion of the stepped notch 360 is an engagement site where the first end region 302 or second end region 304 of a connector 38 is engaged to the given strut pair 32a and/or 32b.

The connector 38 extends between the stepped notch 360 of a first strut pair 32a of a first expansion strut column 24a to a stepped notch 360 of a longitudinally adjacent second strut pair 32b of a second expansion strut column 24b. In the embodiment shown in FIGS. 13-15 the notch 360 of the first strut pair 32a has a contra-lateral position relative to the notch 360 of the second strut pair 32b to which a given connector 38 is in communication therebetween.

In at least one embodiment, as best shown in FIG. 13, some first and/or second expansion struts 28a and/or 28b are provided with no stepped notches 360. While other struts 28a and/or 28b are provided with at least two stepped notches 360, indicated and 360a and 360b. While connectors 38 are depicted as extending from either or both of the proximal most notch and/or distal most notch, it should be recognized that a connector 38 may engage a given first or second strut pair at any point desired.

The connectors 38 shown in FIGS. 13-15 are provided with four bend portions 310a, 310b, 310c and 310d.

As a result of the unique shape of the connectors 38 and the longitudinally offset arrangement of adjacent first expansion strut pairs 32a and second expansion strut pairs 32b, as the wrap portion 308 of each connector 38 wraps about the first joining strut 30a of the first expansion strut pair 24a it also wraps about the first joining strut 30a of the second expansion strut pair 24b.

A pair of circumferentially adjacent connectors 38 and longitudinally adjacent first expansion strut pair 32a and second expansion strut pair 32b form an asymmetrical cell space 40 as described above. In at least one embodiment, an example of which is shown in FIG. 15 the connectors 38 and the expansion strut pairs 32a and 32b which define the cell space 40 have a cell perimeter of at least 5 mm, and may be at least 7 mm or more. In at least one embodiment the perimeter of the cell space 40 is about 8.19 mm.

Figure 16:
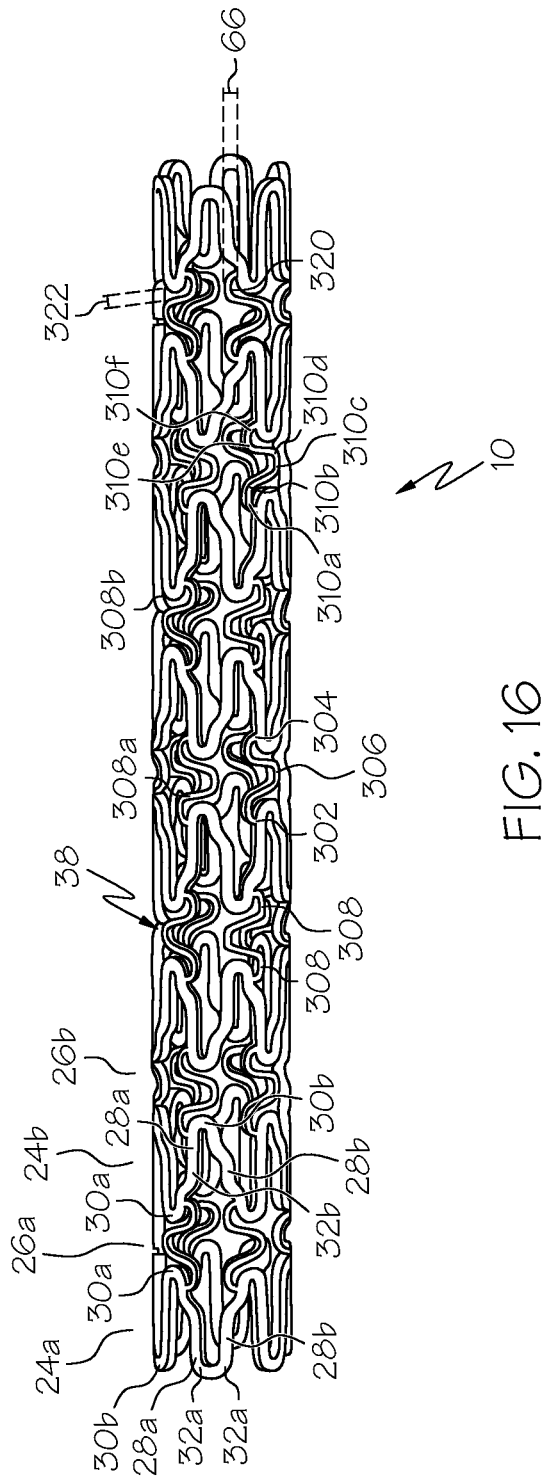
FIG. 16 is a perspective view of an embodiment of the invention.
Figure 17:
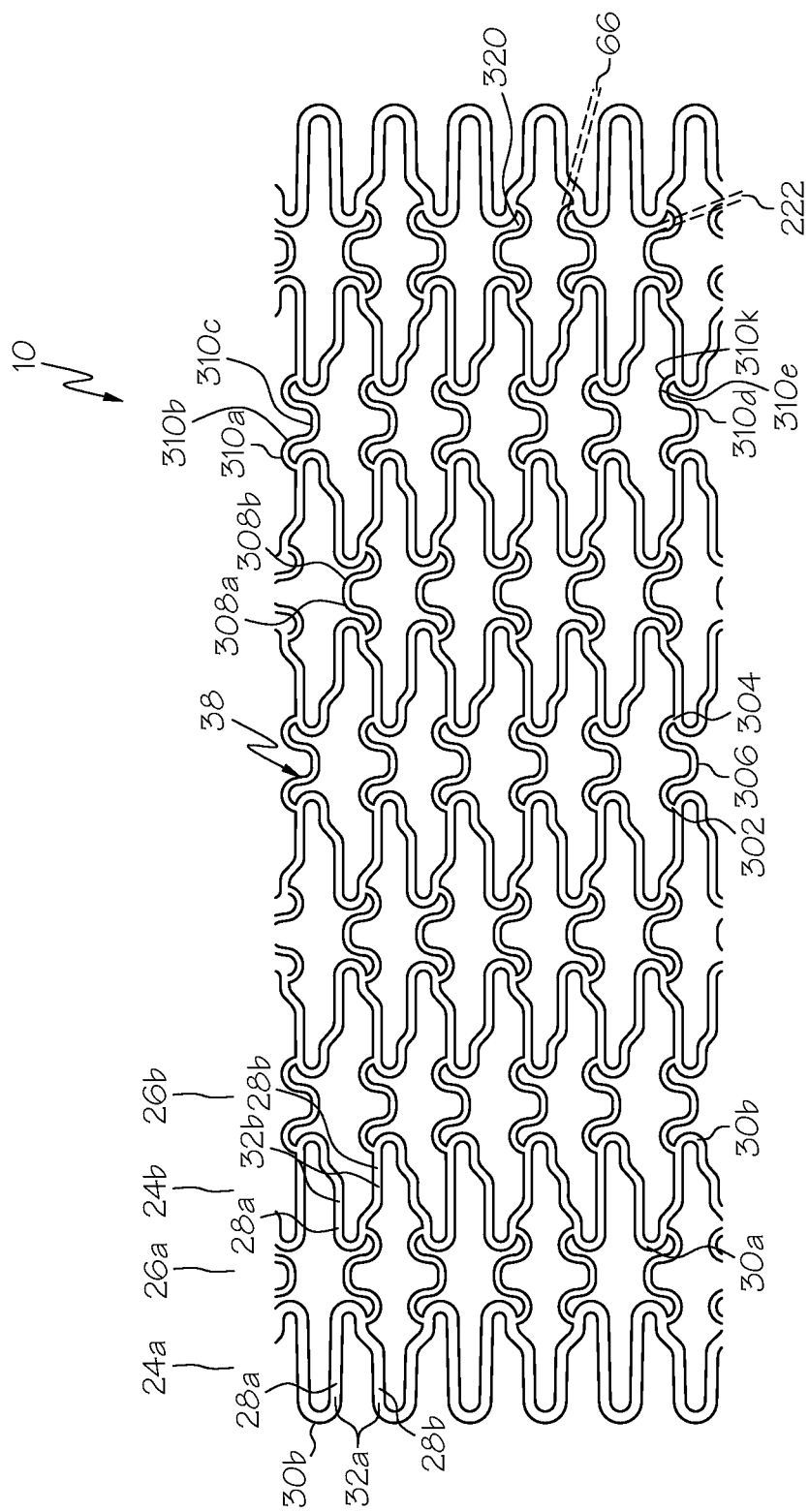
FIG. 17 is a side view of the embodiment shown in FIG. 16.
Figure 18:
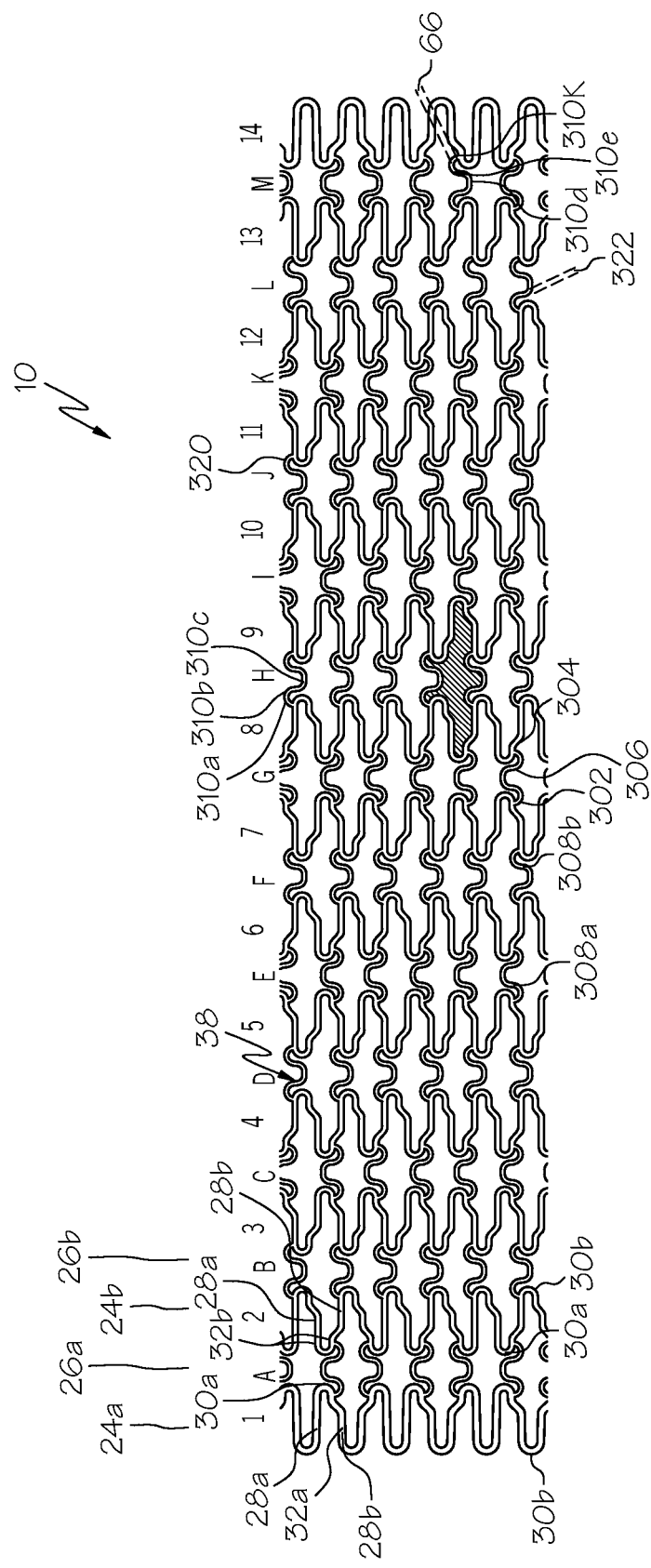
FIG. 18 is a side view of the embodiment shown in FIGS. 16 and 17.

Turning to the embodiments depicted in FIGS. 16-18 the first and second expansion struts 28a and 28b may be configured in any of the variety of manners describe in relation to the embodiments of FIGS. 13-15.

As to the connectors 38 however, in the embodiments depicted in FIGS. 16-18 the connectors 38 of the present embodiments are provided with at least 6 bend portions 310a, 310b, 310c, 310d, 310e and 310f.

Each bend portion, like all bend portions described herein may act as a pivot point about which the connector may bend and or flex as the stent 10 is expanded or reduced in diameter.

The first end region 302 of the connector 38 is engaged to the first expansion strut pair 32a and the second end region 304 of the connector 38 is engaged to an adjacent second expansion strut pair 32b in an ipsilateral arrangement as best shown in FIGS. 17 and 18.

Like the embodiments shown in FIGS. 13-18 the embodiments shown in FIGS. 19 and 20 are also provided with stepped notches 360 in one or more first expansion strut 28a and/or second expansion strut 28b. Furthermore, in the embodiments depicted in FIGS. 19 and 20 one or more of the first expansion struts 28a and/or second expansion struts 28b are provided with one or more expansion strut bend portions 312. As is shown, each first expansion strut pair 32a and second expansion strut pair 32b is provided with a first expansion strut 28a having at least one bend portion 312 and a second expansion strut 28b having at least one stepped notch 360. This arrangement of alternating struts having at least one bend portion 312 and struts having at least one stepped notch 360, results in a stent 10 having first and second struts 28a and 28b with no portion thereof being parallel to the longitudinal axis 17 of the stent 10. However, in the embodiments shown in FIGS. 19 and 20, the distal most expansion strut column and the proximal most expansion strut column of the stent 10 may be provided with expansion strut pairs wherein at least a portion of one or more expansion struts 28a and/or 28b is parallel to the longitudinal axis 17.

The wrap portion 308 of each connector 38 wraps about both the first joining strut 30a of the first expansion strut pair 32a as well as the first joining strut 30a of the second expansion strut pair 32b as it extends between the first expansion strut pair 32a and the second expansion strut pair 32b.

The first end region 302 of the connector 38 is engaged to one of the first expansion struts 28a or second expansion struts 28b of the first expansion strut column 24a. The second end region 304 of the connector 38 is engaged to one of the first expansion struts 28a or second expansion struts 28b of the second expansion strut column 24b. The connectors 38 have end regions 302 and 304 that are contralaterally engaged to opposing first expansion strut pairs 32a and second expansion strut pairs 32b.

In the embodiment shown in FIG. 19 the intermediate region 306 of each connector comprises at least four bend portions 310a, 310b, 310c and 310d. In the embodiment shown in FIG. 20, at least some of the connectors 38 are provided with intermediate regions having at least 5 bend portions 310a, 310b, 310c, 310d and 310e.

As indicated above, any of the stent 10 described herein may be provided with one or more radiopaque markers, coatings or other mechanisms or devices for improving the radiopacity of at least a portion of the stent. In FIG. 20 one or more of a first expansion strut 28a or second expansion strut 28b defines a radiopaque marker housing 362. A radiopaque marker housing 362 may be positioned anywhere on the stent including but not limited to a mid portion of the stent, one or more areas of the stent adjacent thereto, on or both end regions of the stent, etc. For example, in the embodiment shown, a pair of housings are provided with each housing 362 positioned near the proximal end 12 and the distal end 14 of the stent 10. A radiopaque marker 363 of any type known in the art, including rivets, bands, etc may be positioned at least partially within, on, and/or about the housing 362.

Turning now to the embodiment of FIG. 21, in the embodiment shown, each first expansion strut column 24a comprises first expansion strut pairs 32a which are comprised of a first expansion strut 28a and a second expansion strut 28b, wherein one of the first expansion strut 28a or the second expansion strut 28b is parallel to the longitudinal axis 17 of the stent 10. Similarly each second expansion strut column 24b comprises second expansion strut pairs 32b which are comprised of a first expansion strut 28a and a second expansion strut 28b, wherein one of the first expansion strut 28a or the second expansion strut 28b is parallel to the longitudinal axis 17 of the stent 10. Each first expansion strut 28a and each second expansion strut 28b of a first and second expansion strut pair 32a and 32b is respectively joined by a first joining strut.

Where the first expansion strut 28a of a given first or second expansion strut column is parallel to the longitudinal axis 17 of the stent 10, each first expansion strut 28a is also parallel to every other first expansion strut 28a of the first or second expansion strut column of which it is a member. Similarly, where the second expansion strut 28b of a given first or second expansion strut column is parallel to the longitudinal axis 17 of the stent 10, each second expansion strut 28b is also parallel to every other second expansion strut 28b of the first or second expansion strut column of which it is a member.

In the embodiment shown in FIG. 21 at least a portion of each first expansion strut 28a of each expansion strut pair 32a and 32b forms an acute angle with the second expansion strut 28b. One of the first expansion strut 28a or second expansion strut 28b of each expansion strut pair 32a and 32b has at least one expansion strut bend 312.

Connectors 38 extend between a first expansion strut pair 32a and an adjacent second expansion strut pair 32b, wherein the first end region 302 of the connector 38 is engaged to the at least one expansion strut bend of the first expansion strut pair 32a and the second end region 304 of the connector 38 is engaged to the at least one expansion strut bend of the second expansion strut pair 32b in an ipsilateral configuration.

The wrap portion 308 of each connector 38 wraps about only one of either the first joining strut 30a of the respective first expansion strut pair 32a and the second expansion strut pair 32b to which an individual connector 38 is engaged.

As is shown in the embodiment depicted in FIG. 21 the wrap portion 308 and the joining strut 30a or 30b form the slot region 320 as previously described. The slot region width 322, is no greater than the connection member width 66.

In the embodiment shown in FIG. 21 the intermediate region 306 of each connector 308 comprises at least three bend portions 310a, 310b and 310c.

In the embodiment shown in FIG. 22, a first connecting strut column 26a is comprised of connectors 38 of a substantially similar configuration to those described in the embodiments shown in FIGS. 13-15. The connectors 28 of the first connecting strut column 26a join longitudinally adjacent first expansion strut pairs 32a and second expansion strut pairs 32b in the contra-lateral orientation shown.

In addition to the connectors 38 of the first connecting strut column 26a, the stent 10 is also provided with a second connecting strut column 26b wherein each connector 38 of the second connecting strut column 26b join circumferentially and longitudinally offset second expansion strut pairs 32a and third expansion strut pairs 32c in the ipsilateral orientation shown. The connectors 38 of the second connecting strut column 26b are substantially similar in configuration to the connectors described in relation to the embodiments depicted in FIG. 21.

In other embodiments of the invention shown in FIGS. 23 and 24 the stent is provided with connectors 38, wherein each connector 38 comprises a first wrap portion 308a and a second wrap portion 308b. The first wrap portion 308a of the connector 38 wraps at least partially about the first joining strut 30a of the first strut pair 32a to which the first end region 302 of the connector is engaged.

The second wrap portion 308b of the connector 38 wraps at least partially about the first joining strut 30a of the second strut pair 32b to which the second end region 304 of the connector 38 is engaged.

The first end region 302 of each connector 38 is engaged to one of the first expansion strut 28a or the second expansion strut 28b of a first expansion strut pair 32a and the second end region 304 of each connector 38 is engaged to one of the first expansion strut or the second expansion strut of a second expansion strut pair 32b in a contra-lateral orientation.

Each connector 38 in the embodiments shown in FIGS. 23 and 24 comprise at least four bend portions 310a, 310b, 310c and 310d.

In the embodiment shown in FIG. 23 the connectors 38 have a more elongated configuration when compared to those shown in the embodiment of FIG. 24. In FIG. 24 at least a portion of the intermediate region 306 of each connector 38 is substantially parallel to the longitudinal axis 17 of the stent 10, whereas in the embodiment of FIG. 23 each connectors 38 is provided with an intermediate portion 306 of which at least a portion forms an acute angle 370 with the longitudinal axis 17 of the stent 10 as well as an obtuse angle 372 with the longitudinal axis 17 of the stent 10.

In the various embodiments shown in FIGS. 25-33, the stent 10 is comprised of alternating first and second expansion strut columns 24a and 24b, with the first and second expansion strut columns being in communication with one another via a connecting strut column 26a. The first expansion strut column 24a includes first expansion strut pairs 32a wherein at least one or both of the first expansion strut 28a and the second expansion strut 28b have one or more stepped notches 360 as previously described.

In the various embodiments shown in FIGS. 25-33 each of the connectors 38 include a first end region 302 which is engaged to and extends from the stepped notch 360 of the first expansion strut pair 24*a* and a second end region 304 which is engaged to and extends from a stepped notch 360 of the second expansion strut pair.

In some embodiments, such as for example those shown in FIGS. 25, 26, 30-31, the first end region 302 and the second end region 304 are engaged respectively to a first expansion strut pair 32*a* and a second expansion strut pair 32*b* in a contra-lateral configuration. In other embodiments, for example those shown in FIGS. 27-29 and 32-33, the first end region 302 and the second end region 304 are engaged respectively to a first expansion strut pair 32*a* and a second expansion strut pair 32*b* in an ipsilateral configuration.

In the various embodiments shown in FIGS. 25-33, the connectors 38 are provided with a connector width 66 and the first and second expansion struts 28*a* and 28*b* which comprise the first and second expansion strut pairs 32*a* and 32*b* are provided with an expansion strut width 62. In many of the embodiments described herein, including those depicted in FIGS. 25-33, the expansion strut width 62 is greater than the connector width 66. It is noted however that in some embodiments the stent 10 may be provided with connectors 38 wherein at least a portion of a connector width 66 is equal to or greater than at least a portion of the expansion strut width 62.

In some embodiments such as those depicted in FIGS. 42, 49 and 53 within a given expansion strut column there may be differences in the width of the expansion struts relative to one another. Similarly within a given connecting strut column the width of the connectors may vary from one another.

In the embodiments shown in FIGS. 25-31 the connectors 38 share the common featured of having one or both of first end region 302 and second end region 304 of each connector extend in a substantially linear manner from the stepped notch 360 of either the first expansion strut 28*a* or the second expansion strut 28*b* of a respective first expansion strut pair 32*a* or second expansion strut pair 32*b*. In some embodiments a portion of the connector 38 adjacent to one or both of the end regions 302 and 304 may be substantially parallel to the expansion strut to which it is respectively engaged. In other embodiments one or more portions of the connector 38 adjacent to the end regions 302 and 304 may define an angle of about 180 degrees to about 135 degrees with the respective expansion strut 28*a* or 28*b* to which they are each respectively engaged. In some embodiment the angle thusly defined is about 135 degrees or greater.

As is clear from the various embodiments shown, the intermediate region 306 of the connectors 38 depicted in the embodiments of FIGS. 25-33 may be provided with a diverse number of bend portions. For example in the embodiment shown in FIGS. 25-29 the intermediate portion 306 comprises two bend portions 310*a* and 310*b*. In the embodiments shown in FIGS. 30 and 31 the intermediate portion comprises at least four bend portions 310*a*, 310*b*, 310*c* and 310*d*.

In the embodiments shown in FIGS. 32 and 33 the connectors 38 differ from those shown in FIGS. 25-31 in that one or both of the first end region 302 and the second end region 304 of each connector 38 extends laterally away from the stepped notch 360 of either the first expansion strut 28*a* or the second expansion strut 28*b* of a respective first expansion strut pair 32*a* or second expansion strut pair 32*b* to which they are engaged.

In the embodiments shown in FIGS. 25-33 one or both of the end regions 302 and 304 may be substantially linear as previously described above. However, in some of the embodiments shown such as including the embodiments of FIGS. 28-33 a connector 38 may initially extend longitudinally and/or circumferentially away from the expansion strut pair to which it is engaged and then change course back toward the strut pair before engaging the adjacent strut pair of the adjacent strut pair column. The combination of an end region 302 and/or 304 which extend away from the expansion strut pair to which it or they are engaged and an intermediate region 306 of which at least a portion returns back toward the expansion strut pair to which the connector is engaged forms a distinctive wrap portion 308 of the connector 38 which wraps about the first joining strut 30*a* of at least one of the first expansion strut pair 32*a* and second expansion strut pair 32*b* respectively.

In some embodiments described herein the intermediate section 306 of a given connector 38 may be further comprised of one or more substantially linear sections, such as for example: a first substantially linear section 382, a second substantially linear section 384 and/or a third substantially linear section 386 depicted in FIGS. 26 and 27. A given connector may have only a single substantially linear section or any plurality of substantially linear sections. More typically however a connector may have between two and eight substantially linear sections. Some example embodiments having one or more substantially linear sections are shown in FIGS. 25-33. Other embodiments described herein may also include one or more substantially linear sections.

As is shown in various embodiments, and most clearly depicted in FIGS. 26 and 31, where a connector 38 has intersecting substantially linear sections, such as for example a first and a second substantially linear sections 382 and 384, the intersection of the substantially linear sections is comprised of at least one bend or curved portion 310*a-f*. The intersection of the substantially linear sections may define a slant angle 58 as previously described. In some embodiments the intersections of the substantially linear sections may define a radius of curvature, which may vary between different intersections of different sections of the connector.

In some embodiments, some examples of which are shown in the embodiments of FIGS. 26 and 31, at least two substantially linear sections, such as the first and third substantially linear sections 382 and 386, respectively, are substantially parallel to one another. In some embodiments, an example of which is shown in FIG. 29, the first substantially linear section 382 and the second substantially linear section 384 define a slant angle 58 which is obtuse, and the second substantially linear section 384 and the third substantially linear section 386 define a slant angle 58 that is also obtuse.

Where a connector is comprised of one or more substantially linear sections as described, the individual sections may be substantially the same or different from one another in their various physical characteristics, such as length, width, thickness, cross-sectional shape, composition, angular orientation to one another, etc. For example in the embodiment shown in FIG. 27, each of the first, second and third substantially linear sections 382, 384 and 386 respectively, have a different length.

While in many of the embodiments described thus far, the end regions 302 and 304 are often respectively engaged to expansion strut pairs wherein the engagement of the end region is closer in proximity to one expansion strut verses the other of the given expansion strut pair, in some embodiments, such as for example the embodiment shown in FIG. 34, at least one of the end regions, in this example the second end region 304 is engaged to a second expansion strut pair 32*b* at a location substantially equivalent in proximity to the first expansion strut 28*a* and the second expansion strut 28*b*. As a result of this connector configuration, the wrap portion 308 of the connector wraps only the first joining strut 30*a* of the first strut pair 32*a*.

In some embodiments of the invention, some examples of which are depicted in the embodiments of FIGS. 35A-65, the connectors 38 may be characterized as comprising a first wrap portion 308*a*, a second wrap portion 308*b*, and at least one substantially linear section 382 therebetween.

In the various embodiments shown in FIGS. 35A-65, the first end region 302 of a connector 38 is engaged to one of the first expansion strut 28*a* or the second expansion strut 28*b*, at or adjacent to a stepped notch 360, of a first strut pair 32*a*. The second end region 302 of a connector 38 is engaged to one of the first expansion strut 28*a* or the second expansion strut 28*b*, at or adjacent to a stepped notch 360, of a second expansion strut pair 32*b*.

The first wrap portion 308*a* extends from the first end region 302 and wraps at least partially around the first joining strut 28*a* of the first expansion strut pair 32*a*. The wrap portion is substantially parallel to the first joining strut 28*a*. The first wrap portion 308*a* and the first joining strut 28*a* define a slot region 320, wherein the slot region 320 defines a slot region width 322, the slot region width 322 is no greater than the connecting strut width 66.

The second wrap portion 308*b* extends from the second end region 304 and wraps at least partially around the first joining strut 28*a* of the second expansion strut pair 32*b*. The wrap portion is substantially parallel to the first joining strut 28*a*. The second wrap portion 308*b* and the first joining strut 28*a* define a slot region 320, wherein the slot region 320 defines a slot region width 322, the slot region width 322 is no greater than the connecting strut width 66.

In at least one embodiment, such as for example in the embodiment shown in FIG. 36A, the slot region width 322 may be about 0.0025 inch while the connecting strut width is about 0.0030 inch.

As shown in the embodiments of FIGS. 35A-40 and 48-65, the wrap portions 308*a* and 308*b* are each in communication with a common substantially liner section 382. At the intersection of the substantially linear section 382 and the respective wrap portions 308*a* and 308*b* is a bend portion 310*a* and 310*b* respectively present. Depending on the type of connector 38 the bend portions 310*a* and 310*b* may define a range of angles or radii of curvature.

In some embodiments, including those depicted in FIGS. 35A, 36A, and 41-47, the connectors comprise a plurality of interconnected substantially linear sections 382, 384 and 386 respectively. At a first bend portion 310*a*, the first wrap portion 308*a* is in communication with a first substantially linear section 382. At a second bend portion 310*b*, the first substantially linear section 382 is in communication with the second substantially linear section 384. At a third bend portion 310*c* the second substantially linear section is in communication with the third substantially linear section 386. At a fourth bend portion 310*d*, the third substantially linear section 386 is in communication with the second wrap portion 308*b*.

In the embodiments shown in FIGS. 35A-65, the various wrap portions 308*a* and 308*b*, and the various substantially linear sections 382, 384 and 386 may be substantially the same or different from one another in their various physical characteristics, such as length, width, thickness, cross-sectional shape, composition, angular orientation relative to one another, etc.

The various embodiments of the stents described herein may include one or more coatings and/or other delivery mechanisms which comprise one or more therapeutic agents, cellular materials, polymeric agents, drugs, etc.

The therapeutic agent may be non-genetic or genetic. Suitable non-genetic therapeutic agents include anti-thrombogenic agents such as heparin, heparin derivatives, urokinase, and PPack (dextrophenylalanine proline arginine chloromethylketone), anti-proliferative agents such as enoxaprin, angiopeptin, or monoclonal antibodies capable of blocking smooth muscle cell proliferation, hirudin, and acetylsalicylic acid, anti-inflammatory agents such as dexamethasone, prednisolone, corticosterone, budesonide, estrogen, sulfasalazine, and mesalamine, antineoplastic/antiproliferative/anti-miotic agents such as paclitaxel, 5-fluorouracil, cisplatin, vinblastine, vincristine, epothilones, endostatin, angiostatin and thymidine kinase inhibitors, anesthetic agents such as lidocaine, bupivacaine, and ropivacaine, anti-coagulants such as D-Phe-Pro-Arg chloromethyl keton, an RGD peptide-containing compound, heparin, antithrombin compounds, platelet receptor antagonists, anti-thrombin antibodies, anti-platelet receptor antibodies, aspirin, prostaglandin inhibitors, platelet inhibitors and tick antiplatelet peptides, vascular cell growth promoters such as growth factor inhibitors, growth factor receptor antagonists, transcriptional activators, and translational promoters, vascular cell growth inhibitors such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin, cholesterol-lowering agents; vasodilating agents; and agents which interfere with endogenous vasoactive mechanisms.

Suitable genetic materials include anti-sense DNA and RNA, DNA coding for anti-sense RNA, tRNA or rRNA to replace defective or deficient endogenous molecules, angiogenic factors including growth factors such as acidic and basic fibroblast growth factors, vascular endothelial growth factor, epidermal growth factor, transforming growth factor α and β, platelet-derived endothelial growth factor, platelet-derived growth factor, tumor necrosis factor α, hepatocyte growth factor and insulin like growth factor, cell cycle inhibitors including CD inhibitors, thymidine kinase ("TK") and other agents useful for interfering with cell proliferation, the family of bone morphogenic proteins ("BMP's"), BMP-2, BMP-3, BMP-4, BMP-5, BMP-6 (Vgr-1), BMP-7 (OP-1), BMP-8, BMP-9, BMP-10, BMP-11, BMP-12, BMP-13, BMP-14, BMP-15, and BMP-16. Any of BMP-2, BMP-3, BMP-4, BMP-5, BMP-6 and BMP-7 are particularly desirable. These dimeric proteins can be provided as homodimers, heterodimers, or combinations thereof, alone or together with other molecules. Alternatively or, in addition, molecules capable of inducing an upstream or downstream effect of a BMP can be provided. Such molecules include any of the "hedgehog" proteins, or the DNA's encoding them.

Suitable cellular materials include cells of human origin (autologous or allogeneic) or from an animal source (xenogeneic), genetically engineered if desired to deliver proteins of interest at the transplant site. The delivery media can be formulated as needed to maintain cell function and viability.

Suitable polymer coating materials include polycarboxylic acids, cellulosic polymers, including cellulose acetate and cellulose nitrate, gelatin, polyvinylpyrrolidone, cross-linked polyvinylpyrrolidone, polyanhydrides including maleic anhydride polymers, polyamides, polyvinyl alcohols, copolymers of vinyl monomers such as EVA, polyvinyl ethers, polyvinyl aromatics, polyethylene oxides, glycosaminoglycans, polysaccharides, polyesters including polyethylene terephthalate, polyacrylamides, polyethers, polyether sulfone, polycarbonate, polyalkylenes including polypropylene, polyethylene and high molecular weight polyethylene, halogenated polyalkylenes including polytetrafluoroethylene, polyurethanes, polyorthoesters, proteins, polypeptides, silicones, siloxane polymers, polylactic acid, polyglycolic acid, polycaprolactone, polyhydroxybutyrate valerate and blends and copolymers thereof, coatings from polymer dispersions such as polyurethane dispersions (BAYHDROL®, etc.), fibrin, collagen and derivatives thereof, polysaccharides such as celluloses, starches, dextrans, alginates and derivatives, hyaluronic acid, squalene emulsions. Desirably, polyacrylic acid, available as HYDROPLUS® (Boston Scientific Corporation, Natick, Mass.), and described in U.S. Pat. No. 5,091,205, the disclosure of which is hereby incorporated herein by reference, may be used. Also desirably, the polymer may be a copolymer of polylactic acid and polycaprolactone. Other materials include selected medical-grade biodegradable materials such as PGA-TMC, Tyrosine-Derived Polycarbonates and arylates, polycaprolactone co butyl acrylate and other co polymers, Poly-L-lactic acid blends with DL-Lactic Acid, Poly(lactic acid-co-glycolic acid), polycaprolactone co PLA, poly-caprolactone co butyl acrylate and other copolymers, Tyrosine-Derived Polycarbonates and arylate, poly amino acid, polyphosphazenes, polyiminocarbonates, polydimethyltrimethylcarbonates, biodegradable CA/PO$_4$'s, cyanoacrylate, 50/50 DLPLG, polydioxanone, polypropylene fumarate, or polydepsipeptides.

Other suitable coatings include macromolecules such as chitosan and Hydroxylpropylmethylcellulose. Surface erodible materials may also be used. Coatings may also comprise maleic anhydride copolymers, zinc-calcium phosphate and amorphous polyanhydrides.

The inventive medical devices may also be provided with a sugar or more generally a carbohydrate and/or a gelatin to maintain the inventive medical devices on a balloon during delivery of the medical device to a desired bodily location. Other suitable compounds for treating the inventive medical devices include biodegradable polymers and polymers which are dissolvable in bodily fluids. Portions of the interior and/or exterior of the inventive medical devices may be coated or impregnated with the compound. Mechanical retention devices may also be used to maintain the inventive medical devices on the balloon during delivery.

The inventive medical devices may also be provided in whole or in part with one or more of the above therapeutic agents, polymeric coatings or the like. Where multiple therapeutic agents are provided, different coatings and/or mechanisms may release the drugs at different rates. For example, one therapeutic agent may be released at a fast rate and another therapeutic agent may be released at a slow rate. Where multiple polymeric coatings are provided, the coatings may degrade or erode at different rates.

In order to facilitate the retention and delivery of one or more therapeutic agents any of the stent embodiments described herein may be provided with a plurality of cavities or micro holes or slits 27 other surface features, such as depicted in the examples illustrated in FIGS. 66 and 67. The cavities 27 increase or otherwise alter the surface area of the stent to provide the stent 10 with a more optimum agent delivery mechanism. The cavities 27 may extend partially or entirely through the width of a given stent component. Any of the components of the stent 10, including the connectors 38, first and second expansion struts 28a and 28b, first and second joining struts 30a and 30b, etc., may be provided with one or more cavities 27.

The above disclosure is intended to be illustrative and not exhaustive. This description will suggest many variations and alternatives to one of ordinary skill in this art. All these alternatives and variations are intended to be included within the scope of the claims where the term "comprising" means "including, but not limited to". Those familiar with the art may recognize other equivalents to the specific embodiments described herein which equivalents are also intended to be encompassed by the claims.

Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below.

This completes the description of the preferred and alternate embodiments of the invention. Those skilled in the art may recognize other equivalents to the specific embodiment described herein which equivalents are intended to be encompassed by the claims attached hereto.

What is claimed is:

1. A stent comprising:
   A proximal end and a distal end,
   a plurality of serpentine bands including a first substantially serpentine band and a second substantially serpentine band, the serpentine bands formed of interconnected expansion struts, each two interconnected circumferentially adjacent expansion struts forming an expansion strut pair having a closed end and an open end, the expansion struts of the first substantially serpentine band and the expansion struts of the second substantially serpentine band forming stepped notches along their lengths,
   the first substantially serpentine band and the second substantially serpentine band connected by at least one connection member,
   the connection member having a first end and a second end, the connection member extending from and connecting one expansion strut of an expansion strut pair of the first serpentine band to one expansion strut of an expansion strut pair of the second serpentine band,
   wherein
      the first end of the connection member forms a linear extension of the one expansion strut in the first serpentine band and extends adjacent to a closed end in the same direction as the one expansion strut in the first serpentine band, the first end extending further toward the proximal end of the stent than the closed end adjacent thereto, and
      the second end of the connection member forms a linear extension of the one expansion strut in the second serpentine band and extends adjacent to a closed end in the same direction as one expansion strut in the second serpentine band, the second end extending further toward the distal end of the stent than the closed end adjacent thereto.

2. The stent of claim 1 wherein the connection member has a contralateral orientation.

3. The stent of claim 1 wherein the connection member has an intermediate section extending between the first and second ends, the intermediate section including a linear section.

4. The stent of claim 1 wherein the connection member has an intermediate section extending between the first and second ends of the connection member, a first end of the intermediate section curving away from the first end of the connection member, a second end of the intermediate section curving away from the second end of the connection member.

5. The stent of claim 1 comprising a plurality of cavities in the first serpentine band and a plurality of cavities in the second serpentine band.

6. A stent comprising:

A proximal end and a distal end, a plurality of serpentine bands, the serpentine bands formed of interconnected expansion struts, a plurality of the expansion struts having stepped notches along the length of the respective expansion struts, each two interconnected circumferentially adjacent expansion struts forming an expansion strut pair having a closed end and an open end, a plurality of connection members extending between the serpentine bands, each connection member having a first end and a second end and extending from and connecting one expansion strut of an expansion strut pair of one serpentine band to one expansion strut of an expansion strut pair of another serpentine band, wherein the first end of each connection member forms a linear extension of one expansion strut in one serpentine band and extends adjacent to a closed end in the same direction as the one expansion strut in the one serpentine band, a channel formed between the first end of the one connection member and the closed end adjacent thereto, and the second end of the connection member forms a linear extension of the one expansion strut in the another serpentine band and extends adjacent to a closed end in the same direction as the one expansion strut in the another serpentine band, a channel formed between the second end of the one connection member and the closed end adjacent thereto.

7. The stent of claim 6 wherein the connection members have a contralateral orientation.

8. The stent of claim 6 wherein the connection members have an intermediate section extending between the first and second ends, the intermediate section including a linear section.

9. The stent of claim 6 wherein the connection members have an intermediate section extending between the first and second ends of the connection member, a first end of the intermediate section curving away from the first end of the connection member, a second end of the intermediate section curving away from the second end of the connection member.

10. The stent of claim 6 comprising a plurality of cavities in the serpentine bands.

11. A stent comprising:

a plurality of expansion struts having stepped notches along their lengths, expansion struts adjacent one another connected to one another to form loops, the plurality of expansion struts including longer expansion struts and shorter expansion struts, and connection members, each connection member having a first end extending from one expansion strut, a second end extending from another expansion strut and connecting two loops, wherein the first and second ends are circumferentially and longitudinally offset from one another.

12. The stent of claim 11 wherein the connection member have a contralateral orientation.

13. The stent of claim 11 wherein the connection members have an intermediate section extending between the first and second ends, the intermediate section including a linear section.

14. The stent of claim 11 wherein the connection members have an intermediate section extending between the first and second ends of the connection member, a first end of the intermediate section curving away from the first end of the connection member, a second end of the intermediate section curving away from the second end of the connection member.

15. The stent of claim 11 comprising a plurality of cavities in the expansion struts.

16. The stent of claim 1, wherein the at least one connection member is connected to the stepped notch.

17. The stent of claim 6, wherein the connection members are connected to the stepped notches.

18. The stent of claim 11, wherein the connection members are connected to the stepped notches.

* * * * *